US008853146B2

(12) United States Patent
Owens et al.

(10) Patent No.: US 8,853,146 B2
(45) Date of Patent: Oct. 7, 2014

(54) HAPTEN COMPOUNDS AND COMPOSITIONS AND USES THEREOF

(75) Inventors: S. Michael Owens, Little Rock, AR (US); Melinda Gunnell, Conway, AR (US); F. Ivy Carroll, Durham, NC (US)

(73) Assignee: The Board of Trustees of the University of Arkansas, Little Rock, AK (US)

( * ) Notice: Subject to any disclaimer, the term of this patent is extended or adjusted under 35 U.S.C. 154(b) by 870 days.

(21) Appl. No.: 12/596,765

(22) PCT Filed: Apr. 18, 2008

(86) PCT No.: PCT/US2008/060815
§ 371 (c)(1),
(2), (4) Date: Feb. 17, 2010

(87) PCT Pub. No.: WO2008/131216
PCT Pub. Date: Oct. 30, 2008

(65) Prior Publication Data
US 2010/0143391 A1      Jun. 10, 2010

Related U.S. Application Data

(60) Provisional application No. 60/913,124, filed on Apr. 20, 2007.

(51) Int. Cl.
*A61K 38/38*     (2006.01)
*C07C 323/29*    (2006.01)
*C07K 16/44*     (2006.01)
*A61K 39/385*    (2006.01)
*C07C 217/60*    (2006.01)
*C07C 229/34*    (2006.01)
*C07C 323/12*    (2006.01)

(52) U.S. Cl.
CPC ............ *C07K 16/44* (2013.01); *A61K 39/385* (2013.01); *C07C 217/60* (2013.01); *C07C 229/34* (2013.01); *C07C 323/12* (2013.01); *C07C 323/29* (2013.01); *C07K 2317/56* (2013.01); *C07K 2319/40* (2013.01)
USPC ........................................... 514/1.1; 564/340

(58) Field of Classification Search
CPC ........................... C07C 323/29; A61K 39/385
See application file for complete search history.

(56) References Cited

U.S. PATENT DOCUMENTS

| | | |
|---|---|---|
| 4,041,076 A | 8/1977 | Avenia et al. |
| 4,329,281 A | 5/1982 | Christenson et al. |
| 4,341,758 A | 7/1982 | Sakakibara et al. |
| 4,517,290 A | 5/1985 | Wasa |
| 4,816,567 A | 3/1989 | Cabilly et al. |
| 5,041,076 A | 8/1991 | Kantor |
| 5,135,863 A * | 8/1992 | Hu et al. ............... 435/7.9 |
| 5,141,850 A | 8/1992 | Cole et al. |
| 5,160,701 A | 11/1992 | Brown, III et al. |
| 5,238,652 A | 8/1993 | Sun et al. |
| 5,328,828 A * | 7/1994 | Hu et al. ............... 435/7.9 |
| 5,415,994 A | 5/1995 | Imrich et al. |
| 5,451,504 A | 9/1995 | Fitzpatrick et al. |
| 5,492,841 A | 2/1996 | Craig |
| 5,501,987 A | 3/1996 | Ordonez et al. |
| 5,545,806 A | 8/1996 | Lonberg et al. |
| 5,545,807 A | 8/1996 | Surani et al. |
| 5,559,041 A | 9/1996 | Kang et al. |
| 5,569,825 A | 10/1996 | Lonberg et al. |
| 5,620,890 A | 4/1997 | Kamps-Holtzapple et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,690,942 A | 11/1997 | Hjorth |
| 5,976,812 A | 11/1999 | Huber et al. |
| 6,087,184 A | 7/2000 | Magginetti et al. |
| 6,306,616 B1 | 10/2001 | Shindelman |
| 6,358,710 B1 | 3/2002 | Graves et al. |
| 6,669,937 B2 * | 12/2003 | Owens et al. ............ 424/142.1 |
| 7,037,669 B2 | 5/2006 | Zheng et al. |
| 7,202,348 B2 * | 4/2007 | Owens et al. ............ 530/388.9 |
| 7,371,829 B2 | 5/2008 | McConnell et al. |
| 7,632,929 B2 | 12/2009 | Owens |
| 7,858,756 B2 * | 12/2010 | Owens et al. ............ 530/388.1 |
| 2001/0051158 A1 | 12/2001 | Owens et al. |
| 2003/0119083 A1 | 6/2003 | Owens et al. |
| 2003/0171435 A1 | 9/2003 | Pouletty et al. |
| 2004/0242848 A1 | 12/2004 | Owens et al. |
| 2006/0134711 A1 | 6/2006 | Hui |
| 2007/0207145 A1 | 9/2007 | Owens et al. |
| 2007/0238653 A1 | 10/2007 | Owens |
| 2010/0055126 A1 | 3/2010 | Owens et al. |

FOREIGN PATENT DOCUMENTS

| | | |
|---|---|---|
| EP | 0239400 A2 | 9/1987 |
| EP | 0343346 A1 | 11/1989 |
| EP | 0375422 A2 | 6/1990 |

(Continued)

OTHER PUBLICATIONS

Kimura et al, Immunology, Location of Membrane-Bound Hapten with Different Length Spacers, 1990, 69, pp. 323-328.*
Schmitt et al, Chim. Ther., Synthesis of Anorexigenic Compounds from Pervitin, 1967, 2(4), pp. 260-267, English abstract.*
International Search Report dated Jul. 22, 2008 from related PCT application No. PCT/US2008/060815, 8 pgs.
Supplementary European Search Report from related EP Application No. EP 08 74 6264 dated Oct. 19, 2010, 8 pages.
Byrnes-Blake, "Generation of anti-(+) methamphetamine antibodies is not impeded by (+) methamphetamine administration during active immunication of rats", International Immunopharmacology, 2001, pp. 329-338, Elsevier.

(Continued)

Primary Examiner — Paul A Zucker
(74) Attorney, Agent, or Firm — Polsinelli PC

(57) ABSTRACT

The invention generally relates to hapten compounds comprising either (+)methamphetamine or (+)amphetamine conjugated to a linker. Generally speaking, hapten compounds of the invention may be used to elicit an immune response to one or more of (+)methamphetamine, (+)amphetamine, or (+)MDMA.

20 Claims, 15 Drawing Sheets

(56) References Cited

FOREIGN PATENT DOCUMENTS

| EP | 0574782 A2 | 12/1993 |
|---|---|---|
| EP | 1331219 A1 | 7/2003 |
| FR | EP 1331219 A1 * | 7/2003 |
| WO | 86/01533 A1 | 3/1986 |
| WO | 92/03163 A1 | 3/1992 |
| WO | 97/49732 A1 | 12/1997 |
| WO | 01/81424 A1 | 11/2001 |
| WO | 03/061595 A2 | 7/2003 |
| WO | 2004/050032 A2 | 6/2004 |
| WO | 2005/093417 A1 | 10/2005 |
| WO | 2007/147122 A2 | 12/2007 |
| WO | 2008/131216 A1 | 10/2008 |

OTHER PUBLICATIONS

Peterson, "Using Hapten Design to Discover Therapeutic Monoclonal Antibodies for Treating Methamphetamine Abuse", The Journal of Pharmacology and Experimental Therapeutics, 2007, pp. 30-39, vol. 322, No. 1.

Kosten, "Immunotherapy for the treatment of drug abuse", Pharmacology & Therapeutics, 2005, pp. 76-85, vol. 108, Elsevier.

Office Action dated Feb. 13, 2007 from related U.S. Appl. No. 10/828,782, 5 pages.

Office Action dated May 12, 2008 from related U.S. Appl. No. 11/738,789, 12 pages.

Office Action dated Jun. 11, 2008 from related U.S. Appl. No. 11/733,085, 15 pages.

Office Action dated Dec. 15, 2008 from related U.S. Appl. No. 11/733,085, 16 pages.

Office Action dated Dec. 15, 2008 from related U.S. Appl. No. 11/738,789, 12 pages.

Office Action dated May 21, 2009 from related U.S. Appl. No. 11/738,789, 8 pages.

Office Action dated Sep. 25, 2009 from related U.S. Appl. No. 11/763,948, 11 pages.

Office Action dated Dec. 3, 2009 from related U.S. Appl. No. 11/738,789, 7 pages.

Office Action dated Mar. 24, 2010 from related U.S. Appl. No. 11/763,948, 10 pages.

Office Action dated Oct. 26, 2011 from related European Patent Application No. 07798645.3, 4 pages.

Office Action dated Nov. 8, 2011 from related U.S. Appl. No. 12/611,708, 15 pages.

Owens, S. et al., "Antibodies Against Arylcyclohexylamines and Their Similarities in Binding Specificity with the Phencyclidine Receptor," J. Pharmacol. Exp. Therapeutics, 1998, pp. 472-478, vol. 246, No. 2.

Owens, S. et al., "Anti-Phencyclidine Fab as a Tool for Studying the Toxic Effects Phencyclidine," NIH Immunotoxicology Workshop, Oct. 17-18, 1983, Session B—Poster 27, 3 pages.

Owens, S. et al., "New Generation of Medications for Drug Abuse," Pharmaceutical News, 1998, pp. 44-58, vol. 5, No. 6.

Owens, S. et al., "Phencyclidine-Specific Fab Fragments Alter Phencyclidine Disposition in Dogs," Drug Metabolism and Disposition, 1986, pp. 52-58, vol. 14, No. 1.

Peakman, T. et al., "Comparison of expression of a humanized monoclonal antibody in mouse NSO myeloma cells and Chinese Hamster Ovary cells," Hum. Antibod. Hybridomas, 1994, pp. 65-74, vol. 5, Nos. 1 and 2.

Peterson, E. et al., "Monoclonal Antibody Form and Function: Manufacturing the Right Antibodies for Treating Drug Abuse", The AAPS Journal, 2006, pp. E383-E390, vol. 8, No. 2, Article 43.

Pitas, G. et al., "Anti-Phencyclidine Monoclonal Antibody Binding Capacity is not the Only Determinant of Effectiveness, Disproving the Concept That Antibody Capacity is Easily Surmounted," American Society for Pharmacology and Experimental Therapeutics, 2006, pp. 906-912, vol. 34, No. 6.

Proksch, J. et al., "Anti-Phencyclidine Monoclonal Antibodies Provide Long-Term Reductions in Brain Phencyclidine Concentrations during Chronic Phencyclidine Administration in Rats," J. Pharmacol. Exp. Therapeutics, 2000, pp. 831-837, vol. 292, No. 3.

Proksch, J. et al., "The Effect of Rate of Drug Administration on the Extend and Time Course of Phencyclidine Distribution in Rat Brain, Testis, and Serum," Drug Metabolism and Disposition, 2000, pp. 742-747, vol. 28, No. 7.

Proksch, J. et al., "Pharmacokinetic Mechanisms for Obtaining High Renal Coelimination of Phencyclidine and a Monoclonal Antiphencyclidine Antigen-Binding Fragment of Immunoglobulin G in the Rat," J. Pharmacol. Exp. Therapeutics, 1998, pp. 616-624, vol. 287, No. 2.

Reichert, J. et al., "Monoclonal antibodies in the clinic," Nature Biotechnology, Sep. 2001, pp. 819-822, vol. 19.

Richards, J. et al., "Methamphetamine Abuse and Emergency Department Utilization," West J. Med., 1999, pp. 198-202, vol. 170, No. 4.

Riviere, G. et al., "Disposition of Methamphetamine and Its Metabolite Amphetamine in Brain and Other Tissues in Rats after Intravenous Administration," J. Pharmacol. Exp. Therapeutics, 2000, pp. 1042-1047, vol. 292, No. 3.

Riviere, G. et al., "Spontaneous Locomotor Activity and Pharmacokinetics of Intravenous Methamphetamine and Its Metabolite Amphetamine in the Rat," J. Pharmacol. Exp. Therapeutics, 1999, pp. 1220-1226, vol. 291, No. 3.

Sato, M. et al., "Relapse of Paranoid Psychotic State in Methamphetamine Model of Schizophrenia," Schizophrenia Bulletin, 1992, pp. 115-122, vol. 18, No. 1.

Simmons, L., et al., "Expression of full-length immunoglobulins in *Escherichia coli*: rapid and efficient production of aglycosylated antibodies," J. Immunol. Methods, 2002, pp. 133-147, vol. 263.

Sinacore, M. et al., "Adaptation of Mammalian Cells to Growth in Serum-Free Media," Molecular Biotechnology, 2000, pp. 249-257, vol. 15.

Smith, T. et al., "Immunogenicity and kinetics of distribution and elimination of sheep digoxin-specific IgG and Fab fragments in the rabbit and baboon," Clin. Exp. Immunol., 1979, pp. 384-396, vol. 36.

Smith, T. et al., "Treatment of Life-Threatening Digitalis Intoxication With Digoxin-Specific Fab Antibody Fragments," The New England Journal of Medicine, 1982, pp. 1357-1362, vol. 307, No. 22.

Spector, S., "Antibodies As Pharmacological Agents," Biochemical Pharmacology, 1976, pp. 2427-2428, vol. 25.

Extended European Search Report mailed Jun. 14, 2010 from related European Patent Application No. 07798645.3, 7 pages.

Suttijitpaisal, P. et al., "Immunoassays of Amphetamines: Immunogen Structure vs Antibody Specificity," Asian Pacific Journal of Allergy and Immunology, 1992, pp. 159-164, vol. 10.

Tempest, P. et al. "Reshaping a Human Monoclonal Antibody to Inhibit Human Respiratory Syncytial Virus Infection in Vivo," Biotechnology, 1991, pp. 266-271, vol. 9.

Terazawa, K. et al., "Development of Monoclonal Antibodies Reactive With Methamphetamine Raised Against a New Antigen," Journal of Immunoassay, 1991, pp. 277-292, vol. 12, No. 2.

Tokura, S. et al., "Induction of Methamphetamine-Specific Antibody Using Biodegradable Carboxymethyl-chitin," Analytical Biochemistry, 1987, pp. 117-122, vol. 161.

Usagawa, T. et al. "Preparation of monoclonal antibodies against methamphetamine," J. Immunology Methods, 1989, pp. 111-115, vol. 119.

Valentine, J. et al., "Anti-phencyclidine Monoclonal Fab Fragments Markedly Alter Phencyclidine Pharmacokinetics in Rats," J. Pharmacol. Exp. Therapeutics, 1994, pp. 1079-1085, vol. 269, No. 3.

Valentine, J. et al., "Antiphencyclidine Monoclonal Antibody Therapy Significantly Changes Phencyclidine Concentrations in Brain and Other Tissues in Rats," J. Pharmacol. Exp. Therapeutics, 1996, pp. 717-724, vol. 278, No. 2.

Valentine, J. et al., "Antiphencyclidine Monoclonal Fab Fragments Reverse Phencyclidine-Induced Behavioral Effects and Ataxia in Rats," J. Pharmacol. Exp. Therapeutics, 1996, pp. 709-716, vol. 278, No. 2.

Ward, C. et al., "Radioimmunoassay for the Dual Detection of Amphetamine and Methamphetamine," Journal of Forensic Science, 1994, pp. 1486-1496, vol. 39, No. 6.

(56) References Cited

OTHER PUBLICATIONS

Whitelegg, N. et al., "WAM: an improved algorithm for modelling antibodies on the WEB," Protein Engineering, 2000, pp. 819-824, vol. 13, No. 12.
Notice of Allowance dated Jun. 4, 2012 for related U.S. Appl. No. 12/611,708; 8 pages.
International Preliminary Examination Report dated Jul. 29, 2004 from International Patent Application No. PCT/US2003/38384, 3 pages.
Interview Summary dated Jan. 31, 2012 from related U.S. Appl. No. 12/611,708, 3 pages.
Office Action dated Jun. 14, 2005 from related U.S. Appl. No. 10/255,462, 9 pages.
Supplementary European Search Report mailed Nov. 3, 2010 from related European Patent Application No. 08746264.4, 8 pages.
Albertson, T. et al, "Methamphetamine and the Expanding Complications of Amphetamines", West J. Med., 1999, pp. 214-219, vol. 170, No. 4.
Alt, F. et al., "Selective Multiplication of Dihydrofolate Reductase Genes Methotrexate-resistant Variants of Cultured Murine Cells," J. Biological Chemistry, 1978, pp. 1357-1370, vol. 253, No. 5.
Aoki, K. et al., "Immunoassay for Methamphetamine With a New Antibody", Forensic Science International, 1990, pp. 245-255, vol. 44.
Byrnes-Blake, K. et al., "Monoclonal IgG affinity and treatment time alters antagonism of (+)-methamphetamine effects in rats," European J. Pharmacol., 2005, pp. 86-94, vol. 521.
Byrnes-Blake, K. et al., "Pharmacodynamic mechanisms of monoclonal antibody-based antagonism of (+)- methamphetamine in rats", European J. Pharmacol., 2003, pp. 119-128, vol. 461.
Choi, M. et al., "Localization of the epitope in methamphetamine and its antibody use for the detection of methamphetamine and benzphetamine by polarization fluoroimmunoassay," J. Immunoassay, 1995, pp. 263-278, vol. 16, No. 3.
Cho, A., et al., "Relevance of Pharmacokinetic Parameters in Animal Models of Methamphetamine Abuse," Synapse, 2001, pp. 161-166, vol. 39.
Clark, M., "Antibody Humanization: a case of the 'Emperor's new clothes'?," Rev. Immunology Today, 2000, pp. 397-402, vol. 21, No. 8.
Cody, J. et al., "Detection of D,L-Amphetamine, D,L-Methamphetamine, and Illicit Amphetamine Analogs Using Diagnostic Products Corporation's Amphetamine and Methamphetamine Radioimmunoassay", Journal of Analytical Toxicology, Sep./Oct. 1990, pp. 321-324, vol. 14, No. 5.
Colbert, D. et al., "Single-Reagent Polarization Fluoroimmunoassay for Amphetamine in Urine," Clin. Chem., 1985, pp. 1193-1195, vol. 31, No. 7.
Colburn, W., "Specific Antibodies and Fab Fragments to Alter the Pharmacokinetics and Reverse the Pharmacologic/Toxicologic Effects of Drugs," Drug Metab. Rev., 1980, pp. 223-262, vol. 11, No. 2.
Coloma, M., et al., "Novel vectors for the expression of antibody molecules using variable regions generated by polymerase chain reaction," J. Immunological Methods, 1992, pp. 89-104, vol. 152.
Cook, C. et al., "Pharmacokinetic of methamphetamine self-administered to human subjects by smoking S-(+)- methamphetamine hydrochloride," Drug Metabolism and Dispositions, 1993, pp. 717-723, vol. 21, No. 4.
Danger, Y. et al., "Development of murine monoclonal antibodies to methamphetamine and methamphetamine analogues," J. Immunological Methods, 2006, pp. 1-10, vol. 309.
Daniels, J. et al., "Effects of anti-phencyclidine and anti-(+)-methamphetamine monoclonal antibodies alone and in combination on the discrimination of phencyclidine and (+)-methamphetamine by pigeons," Psychopharmacology, 2006, pp. 36-44, vol. 185.
Faraj, B. et al., "Specificity of an Antibody Directed against d-Methamphetamine. Studies with Rigid and Nonrigid Analogs," J. Medicinal Chemistry, 1976, pp. 20-25, vol. 19, No. 1.
Farre, M. et al., "Repeated doses administration of MDMA in humans: pharmacological effects and pharmacokinetics," Psychopharmacology, 2004, pp. 364-375, vol. 173.
Geisse, S., et al., "Protein Expression in Mammalian and Insect Cell Systems," Methods in Enzymology, 1999, pp. 19-42, vol. 306.
Gentry, W. et al., "Safety and efficiency of an anti-(+)-methamphetamine monoclonal antibody in the protection against cardiovascular and central nervous system effects of (+)-methamphetamine in rats," International Immunopharmacology, 2006, pp. 968-977, vol. 6.
Giudicelli, V., et al., "IMGT/V-Quest, an integrated software program for immunoglobulin and T cell receptor V—J and V—D—J rearrangement analysis," Nucleic Acid Res., 2004, pp. W435-W440, vol. 32.
Hardin, J. et al., "Pharmacodynamics of a Monoclonal Antiphencyclidine Fab with Broad Selectivity for Phencyclidine Like Drugs," J. Pharmacol. Exp. Therapeutics, 1998, pp. 1113-1122, vol. 285, No. 3.
Hardin, J. et al., "A Single Dose of Monoclonal Anti-phencyclidine IgG Offers Long-Term Reductions in Phencyclidine Behavioral Effects in Rats," J. Pharmacol. Exp. Therapeutics, 2002, pp. 119-126, vol. 302, No. 1.
International Search Report dated Jul. 2, 2004 for International Patent Application No. PCT/US2003/38384, 1 page.
International Search Report and Written Opinion dated Mar. 10, 2008 for related International Patent Application No. PCT/US07/071354, 17 pages.
International Search Report dated Oct. 10, 2001 for International Patent Application No. PCT/US01/12899, 4 pages.
Interview Summary dated Sep. 16, 2009 for related U.S. Appl. No. 11/738,789, 2 pages.
Kipriyanov, S. et al., "Generation of recombinant antibodies," Molecular Biotechnology, 1999, p. 173-201, vol. 12, No. 2.
Kunert, R., et al., "Stable Recombinant Expression of the Anti HIV-1 Monoclonal Antibody 2F5 After IgG3/IgG1 Subclass Switch in CHO Cells," Biotechnol. Bioeng., 2000, pp. 97-103, vol. 67, No. 1.
International Preliminary Examination Report dated Dec. 10, 2004 from International Patent Application No. PCT/US01/12899; 6 pages.
Kuus-Reichel, K. et al., "Will Immunogenicity Limit the Use, Efficacy, and Future Development of Therapeutic Monoclonal Antibodies?," Clinical and Diagnostic Laboratory Immunology, 1994, pp. 365-372, vol. 1, No. 4.
Lacy, J. et al., "Engineering and Characterization of a Mouse/Human Chimeric Anti-Phencyclidine Monoclonal Antibody," Int. Immunopharmacol., Jan. 2008, pp. 1-11, vol. 8, No. 1.
Laurenzana, E. et al., "Use of Anti-(+)-Methamphetamine Monoclonal Antibody to Significantly Alter (+)-Methamphetamine and (+)-Amphetamine Disposition in Rats," Drug Metabolism and Disposition, 2003, pp. 1320-1326, vol. 31, No. 11.
Laurenzana, E. et al., "Treatment of Adverse Effects of Excessive Phencyclidine Exposure in Rats with a Minimal Dose of Monoclonal Antibody," J. Pharmacol. and Exp. Therap., 2003, pp. 1092-1098, vol. 306, No. 3.
Li, M. et al., "Four-choice drug discrimination in pigeons," Behavioral Pharmacology, 2001, pp. 621-628, vol. 12.
Lim, K. et al., "Crystal Structure of Monoclonal 6B5 Fab Complexed with Phencyclidine," J. Bio. Chem., Oct. 30, 1998, pp. 28576-28582, vol. 273, No. 44.
McClurkan, M., et al., "Disposition of a Monoclonal Anti-phencyclidine Fab Fragment of Immunoglobulin G in Rats," J. Pharmacology and Exp. Therap., 1993, pp. 1439-1445, vol. 266, No. 3.
McMillan, D. et al., "Schedule control of quantal and graded dose-effect curves in a drug-drug-saline discrimination," Pharmacology, Biochemistry and Behavior, 2001, pp. 395-402, vol. 68.
McMillian, D. et al., "Discrimination of pentobarbital doses and drug mixtures under fixed-ratio and fixed-interval reinforcement schedules," Behavioral Pharmacology, 2001, pp. 195-208, vol. 12.
McMillian, D. et al., "Effects of Murine-Derived Anti-Methamphetamine Monoclonal Antibodies on (+)-Methamphetamine Self-Administration in the Rat," J. Pharmacol. Exp. Therapeutics, 2004, pp. 1248-1255, vol. 309, No. 3.

(56) References Cited

OTHER PUBLICATIONS

McMillian, D. et al., "Pharmacokinetic antagonism of (+)methamphetamine discrimination by low-affinity monoclonal anti-methamphetamine antibody," Behavioral Pharmacology, 2002, pp. 465-473, vol. 13.

Nam, K. et al., "Production and Characterization of Monoclonal Antibody That Simultaneously Recognizes Methamphetamine and Its Major Metabolite," Biol. Pharm. Bull., 1993, pp. 490-492, vol. 16, No. 5.

Niwaguchi, T. et al., "Determination of d-Methamphetamine in Urine After Administration of d- or dl-Methamphetamine to Rats by Radioimmunoassay Using Optically Sensitive Antiserum," Journal of Forensic Sciences, 1982, pp. 592-597, vol. 27, No. 3.

Notice of Allowance dated Aug. 19, 2010 from U.S. Appl. No. 11/763,948, 7 pages.

Notice of Allowance dated Aug. 3, 2009 from related U.S. Appl. No. 11/733,085, 7 pages.

Notice of Allowance mailed Jul. 11, 2003 from related U.S. Appl. No. 09/839,549, 6 pages.

Office Action dated Nov. 26, 2001 from related U.S. Appl. No. 09/839,549, 12 pages.

Office Action dated Nov. 16, 2005 from related U.S. Appl. No. 10/255,462, 8 pages.

Office Action dated Feb. 22, 2006 from related U.S. Appl. No. 10/828,782, 8 pages.

Office Action dated Jul. 31, 2006 from related U.S. Appl. No. 10/255,462, 4 pages.

Office Action dated Oct. 24, 2006 from related U.S. Appl. No. 10/828,782, 8 pages.

* cited by examiner

| mAb Name | CDR Regions and RMSD (Å) from mAb6H4 | | | | | |
|---|---|---|---|---|---|---|
| | L1 | L2 | L3 | H1 | H2 | H3 |
| mAb6H8 | 2.27 | 0.84 | 0.67 | 1.85 | 3.36 | 6.67 |
| mAb4G9 | 2.44 | 0.88 | 3.72 | 1.39 | 3.59 | 7.22 | mAb6H4 mAb4G9

SEQUENCE LISTING

<160> NUMBER OF SEQ ID NOS: 18

<210> SEQ ID NO 1
<211> LENGTH: 36
<212> TYPE: DNA
<213> ORGANISM: Mus musculus

<400> SEQUENCE: 1
ggggcggccg cgcgtctcag gacctttgtc tctaac      36

<210> SEQ ID NO 2
<211> LENGTH: 39
<212> TYPE: DNA
<213> ORGANISM: Mus musculus
<220> FEATURE:
<221> NAME/KEY: misc_feature
<222> LOCATION: (11)..(11)
<223> OTHER INFORMATION: N = T or C

<400> SEQUENCE: 2
atggcctgga nttcacttat actctctctc ctggctctc       39

<210> SEQ ID NO 3
<211> LENGTH: 38
<212> TYPE: DNA
<213> ORGANISM: Mus musculus

<400> SEQUENCE: 3
ggggcggccg cagggctcca aggacactgg gatcattt        38

<210> SEQ ID NO 4
<211> LENGTH: 22
<212> TYPE: DNA
<213> ORGANISM: Mus musculus

<400> SEQUENCE: 4
ctcccggtct ccgggtaaat ga                         22

<210> SEQ ID NO 5
<211> LENGTH: 29
<212> TYPE: DNA
<213> ORGANISM: Mus musculus

<400> SEQUENCE: 5
gagtgcagct tcaggagtca ggacctagc                  29

<210> SEQ ID NO 6
<211> LENGTH: 50
<212> TYPE: DNA
<213> ORGANISM: Mus musculus

<400> SEQUENCE: 6
gatgtaaaac ttcaggagtc aggacctggc ctcgtgaaac cttctcagtc    50

<210> SEQ ID NO 7
<211> LENGTH: 30
<212> TYPE: DNA
<213> ORGANISM: Mus musculus

<400> SEQUENCE: 7
gaggtgcagc ttccggagtc aggacctagc                 30

<210> SEQ ID NO 8
<211> LENGTH: 26
<212> TYPE: DNA
<213> ORGANISM: Mus musculus

<400> SEQUENCE: 8
gagtaccagc tccagcagtc tgggac                     26

<210> SEQ ID NO 9
<211> LENGTH: 123
<212> TYPE: PRT
<213> ORGANISM: Mus musculus

<400> SEQUENCE: 9

Gln Val Gln Leu Gln Gln Pro Gly Ala Glu Leu Val Lys Pro Gly Ala
1               5                   10                  15

Ser Met Lys Leu Ser Cys Lys Ala Ser Gly Tyr Thr Phe Thr Ser Phe

```
                20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Asn Lys Tyr Asn Glu Lys Phe
        50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asp Ser Phe Gly Gly Ser Tyr Asp Gly Phe Tyr Ser Met Asp
            100                 105                 110

Tyr Trp Gly Gln Gly Thr Ser Val Thr Val Ser
        115                 120
```

<210> SEQ ID NO 10
<211> LENGTH: 117
<212> TYPE: PRT
<213> ORGANISM: Mus musculus

<400> SEQUENCE: 10

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Val Thr Ser Gly
            20                  25                  30

Tyr Trp Ser Trp Ile Arg Gln Phe Pro Gly Asn Lys Leu Asp Tyr Met
        35                  40                  45

Gly Tyr Ile Ser Tyr Arg Gly Ser Thr Tyr Tyr Asn Pro Ser Leu Lys
    50                  55                  60

Ser Arg Ile Ser Ile Thr Arg Asp Thr Ser Lys Asn Gln Val Tyr Leu
65                  70                  75                  80

Gln Leu Lys Ser Val Ser Ser Glu Asp Thr Ala Thr Tyr Tyr Cys Ser
                85                  90                  95

Tyr Phe Asp Ser Asp Asp Tyr Ala Met Glu Tyr Trp Gly Gln Gly Thr
            100                 105                 110

Ser Val Thr Val Ser
        115
```

<210> SEQ ID NO 11
<211> LENGTH: 115
<212> TYPE: PRT
<213> ORGANISM: Mus musculus

<400> SEQUENCE: 11

```
Asp Val Lys Leu Gln Glu Ser Gly Pro Gly Leu Val Lys Pro Ser Gln
1               5                   10                  15

Ser Leu Ser Leu Thr Cys Ser Val Thr Gly Ser Ser Ile Thr Ser Ala
            20                  25                  30

Tyr Tyr Trp Asn Trp Asn Arg Gln Phe Pro Gly Asn Lys Leu Glu Trp
        35                  40                  45

Met Gly Tyr Ile Arg Tyr Asp Gly Tyr Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Asp Asp Tyr Asp Glu Ala Tyr Trp Gly Gln Gly Thr Leu Val
```

```
                     100                 105                 110
Thr Val Ser
        115

<210> SEQ ID NO 12
<211> LENGTH: 118
<212> TYPE: PRT
<213> ORGANISM: Mus musculus

<400> SEQUENCE: 12

Glu Val Gln Leu Pro Glu Ser Gly Pro Gly Leu Val Ala Pro Ser Gln
1               5                   10                  15

Ser Leu Ser Ile Thr Cys Thr Val Ser Gly Phe Ser Leu Thr Asp Gly
            20                  25                  30

Tyr Gly Val Asn Trp Val Arg Gln Pro Pro Gly Lys Gly Leu Glu Trp
        35                  40                  45

Leu Gly Met Ile Trp Asp Asp Gly Asp Thr Asp Tyr Ser Ser Val Leu
    50                  55                  60

Lys Ser Arg Leu Ser Ile Thr Lys Asp Asn Ser Lys Gln Val Phe Leu
65                  70                  75                  80

Lys Met Asn Arg Leu Gln Thr Asp Asp Thr Ala Arg Tyr Phe Cys Ala
                85                  90                  95

Arg Asp Thr Leu Tyr Thr Ser Tyr Ala Met Asp Tyr Trp Gly Gln Gly
            100                 105                 110

Thr Ser Val Thr Val Ser
        115

<210> SEQ ID NO 13
<211> LENGTH: 114
<212> TYPE: PRT
<213> ORGANISM: Mus musculus

<400> SEQUENCE: 13

Glu Tyr Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Gly Ile Tyr Pro Gly Asn Ser Asp Thr Thr Tyr Asn Gln Lys Phe
    50                  55                  60

Lys Gly Lys Ala Lys Leu Thr Ala Val Thr Ser Thr Ser Thr Ala Tyr
65                  70                  75                  80

Met Glu Leu Ser Ser Leu Thr Asn Glu Asp Ser Ala Val Tyr Tyr Cys
                85                  90                  95

Leu Tyr Gly Asn Tyr Asp Phe Asp Tyr Trp Gly Gln Gly Thr Leu Thr
            100                 105                 110

Val Ser

<210> SEQ ID NO 14
<211> LENGTH: 108
<212> TYPE: PRT
<213> ORGANISM: Mus musculus

<400> SEQUENCE: 14

Gln Ile Val Leu Thr Gln Ser Pro Ala Ile Met Ser Ala Ser Pro Gly
1               5                   10                  15
```

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Ile Leu Ala Ser Gly Val Pro Ala Arg Phe Ser Gly Ser
    50                  55                  60

Gly Ser Gly Thr Ser Tyr Ser Leu Thr Ile Ile Asn Met Glu Ala Glu
65                  70                  75                  80

Asp Ala Ala Thr Tyr Tyr Cys Gln His Tyr His Ser Tyr Pro Leu Thr
                85                  90                  95

Phe Gly Ala Gly Thr Lys Leu Glu Leu Lys Arg Ala
            100                 105

<210> SEQ ID NO 15
<211> LENGTH: 110
<212> TYPE: PRT
<213> ORGANISM: Mus musculus

<400> SEQUENCE: 15

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

His Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Phe Pro
                85                  90                  95

Phe Thr Phe Gly Ser Gly Thr Lys Leu Glu Ile Lys Arg Ala
            100                 105                 110

<210> SEQ ID NO 16
<211> LENGTH: 110
<212> TYPE: PRT
<213> ORGANISM: Mus musculus

<400> SEQUENCE: 16

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Arg Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Phe Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Tyr Thr Phe Gly Gly Gly Thr Lys Leu Glu Ile Lys Arg Ala
            100                 105                 110

<210> SEQ ID NO 17
<211> LENGTH: 111

```
<212> TYPE: PRT
<213> ORGANISM: Mus musculus

<400> SEQUENCE: 17

Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Ala Ser
                20                  25                  30

Asn Tyr Ala Asn Trp Val Gln Glu Lys Pro Asp His Leu Phe Thr Gly
            35                  40                  45

Leu Ile Gly Gly Thr Asn Ile Arg Ala Pro Gly Ile Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Phe Ser Asn
                85                  90                  95

His Ser Val Phe Gly Gly Gly Thr Lys Leu Thr Val Leu Gly Leu
            100                 105                 110

<210> SEQ ID NO 18
<211> LENGTH: 110
<212> TYPE: PRT
<213> ORGANISM: Mus musculus

<400> SEQUENCE: 18

Asp Val Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Ala Asn Leu Leu Pro
                85                  90                  95

Trp Thr Phe Gly Gly Gly Thr Lys Leu Glu Ile Lys Arg Ala
            100                 105                 110
```

HAPTEN COMPOUNDS AND COMPOSITIONS AND USES THEREOF

GOVERNMENTAL RIGHTS

This invention was made with government support under the National Institute on Drug Abuse grant Nos. DA11560, DA14361, and DA05477. The government has certain rights in the invention.

FIELD OF INVENTION

The invention generally relates to hapten compounds comprising either (+) or (−)methamphetamine or (+) or (−)amphetamine conjugated to a linker. Generally speaking, hapten compounds of the invention may be used to elicit an immune response to one or more of (+)methamphetamine, (+)amphetamine, or (+)3,4-methylenedioxymethamphetamine ((+)MDMA).

BACKGROUND OF THE INVENTION (+)-Methamphetamine ((+)METH) abuse has become America's number one drug threat (NACO, 2005) and effective treatment strategies for abuse of (+)METH and related stimulants are greatly needed. Current pharmacotherapies for managing the acute cardiovascular system, central nervous system and toxic effects are mostly supportive (Sato, 1992; Albertson et al., 1999; Richards et al., 1999); and do nothing to remove the drug from its sites of action in the brain. Also lacking are medications that can reduce or treat the medically crippling effects of (+)METH addiction. Antibodies provide an attractive potential medication that can target the drug instead of the site of action (Kosten and Owens, 2005). These high affinity protein-based medications act as so-called pharmacokinetic antagonists, sequestering the drug in the bloodstream away from medically vulnerable tissues like the brain and heart.

Unlike nicotine and cocaine where the effects are caused by a single, specific compound, drugs like opiates (e.g., morphine), arylcyclohexylamines (e.g., phencyclidine) and amphetamines (e.g., (+)METH) are starting structures from which many pharmacologically similar compounds can be synthesized. These so-called "designer drugs" can be chemically modified to alter their effects. Thus, for an antibody to have the broadest medical applicability, it should have high affinity and specificity for other medically important members of this drug class (i.e., (+)METH, (+)AMP and (+)MDMA).

There are other medication design issues that further complicate the development of effective treatments for (+)METH-like stimulants. First, (+)METH is one of several stimulant drugs of abuse with similar or overlapping effects. In particular, (+)AMP is both a pharmacologically active metabolite of (+)METH and a frequently used drug of abuse that could be substituted for (+)METH. Second, (+/−)-3,4-methylenedioxymethamphetamine is the racemic mixture commonly referred to as MDMA or ecstasy. The plus isomer ((+)MDMA) has predominately dopaminergic, stimulant-like activity with overlapping effects with (+)METH, while (−)MDMA has predominately serotonergic effects (Cho and Segal, 1994). (+)METH, (+)AMP, and (+)MDMA can produce life threatening effects at high doses (Cho and Segal, 1994; Farre et al., 2004). Additionally, all of these drugs are plus stereoisomers, with the minus isomers having a significantly different pharmacological profile of effects. For example, (−)-methamphetamine is commonly used as a bronchodilator in over the counter medications. The minus isomers of these drugs could potentially be purposely taken by drug abusers to neutralize mAb medications with high affinity binding for both plus and minus stereoisomers. In a related way, there are many structurally similar compounds like ephedrine and pseudoephedrine that could be used to lessen the efficacy of antibodies if the antibody is not highly specific for (+)METH-like structures.

Hence, there is a need in the art for haptens designed to elicit an immune response that may generate specific antibodies that recognize at least one or more of (+)methamphetamine, (+)amphetamine, or (+)MDMA, and that do not substantially cross-react with (−)methamphetamine, (−)amphetamine, or (−)MDMA, or over the counter medications.

SUMMARY OF THE INVENTION

Accordingly, one aspect of the invention encompasses a hapten compound comprising formula (I):

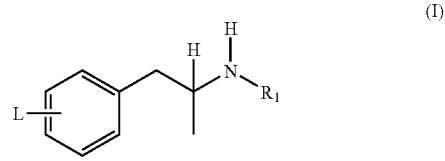

wherein:
$R_1$ is selected from the group consisting of hydrogen and methyl; and
L comprises a linker of at least 8 contiguous atoms, the atoms being selected from the group consisting of hydrogen, hydrocarbyl, and substituted hydrocarbyl; provided, when L is less than 13 contiguous atoms, then the last atom of the linker opposite its point of attachment to the benzene ring does not form a carboxylic acid.

Another aspect of the invention encompasses a hapten compound comprising formula (II):

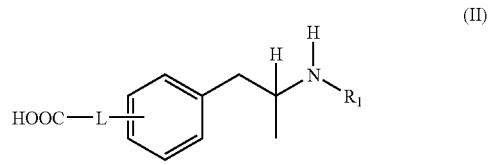

wherein:
$R_1$ is selected from the group consisting of hydrogen and methyl; and
L comprises a linker of at least 11 contiguous atoms, the atoms being selected from the group consisting of hydrogen, hydrocarbyl, and substituted hydrocarbyl.

Yet another aspect of the invention encompasses a hapten compound comprising formula (IV):

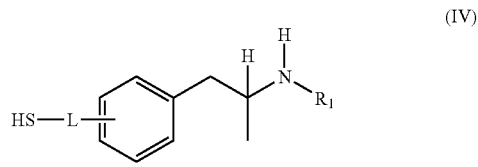

wherein:
$R_1$ is selected from the group consisting of hydrogen and methyl; and L comprises a linker of at least 7 contiguous atoms, the atoms being selected from the group consisting of hydrogen, hydrocarbyl, and substituted hydrocarbyl.

Still another aspect of the invention encompasses a composition comprising a compound selected from the group consisting of a compound of formula (I), a compound of formula (II), a compound of formula (III), a compound of formula (IV), a compound of formula (V), a compound of formula (VI), a compound of formula (VII), a compound of formula (VIII), a compound of formula (IX), and a compound of formula (X).

A further aspect of the invention encompasses a method for eliciting an immune response in a subject. The method comprises administering a composition comprising a compound selected from the group consisting of a compound of formula (I), a compound of formula (II), a compound of formula (III), a compound of formula (IV), a compound of formula (V), a compound of formula (VI), a compound of formula (VII), a compound of formula (VIII), a compound of formula (IX), and a compound of formula (X) to the subject.

Yet another further aspect of the invention encompasses a method for generating specific antibodies for a compound selected from the group consisting of compound of formula (I), a compound of formula (II), a compound of formula (III), a compound of formula (IV), a compound of formula (V), a compound of formula (VI), a compound of formula (VII), a compound of formula (VIII), a compound of formula (IX), and a compound of formula (X). The method comprises administering the compound to a subject.

Still a further aspect of the invention encompasses a method of treating drug use. The method comprises eliciting an immune response in a drug-using subject by administering a composition comprising a compound selected from the group consisting of a compound of formula (I), a compound of formula (II), a compound of formula (III), a compound of formula (IV), a compound of formula (V), a compound of formula (VI), a compound of formula (VII), a compound of formula (VIII), a compound of formula (IX), and a compound of formula (X) to the subject. The immune response decreases the concentration of (+)methamphetamine, (+)amphetamine, or (+)MDMA in the brain of the subject.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 1 presents amino acid sequence alignments of the variable regions of five moderate to high affinity anti-(+)METH and anti-(+)METH/(+)AMP, and anti-(+)METH/(+)AMP/(+)MDMA mAb (herein, mAb refers to monoclonal antibodies, both singular and plural). Panel A presents the amino acid sequences of the heavy chains. Panel B present the amino acid sequences of the light chains. The sequences are presented in single letter amino acid notation and numbered according to Kabat and Wu (1991 J Immunol 147:1709-1719). Location of the framework (FR) and CDR residues are indicated for the heavy chains and light chains.

DETAILED DESCRIPTION OF THE INVENTION

Figure 2:
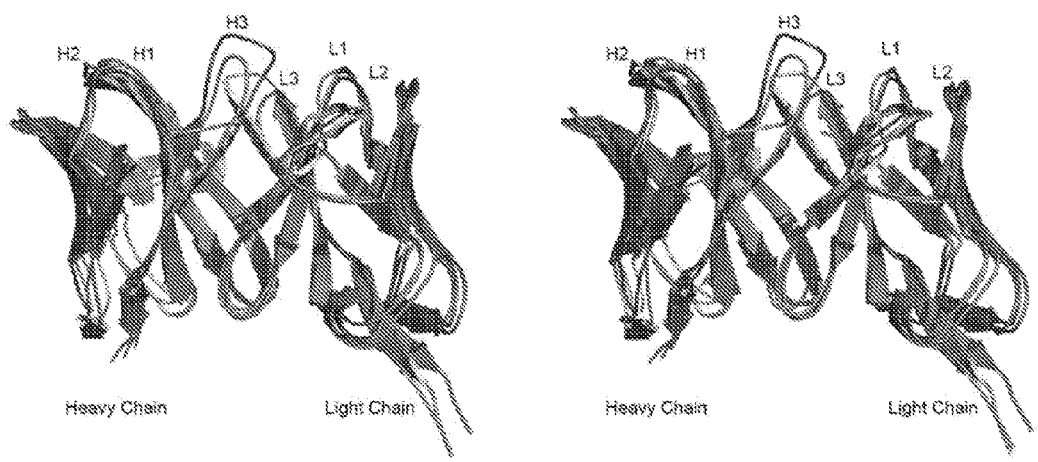
FIG. 2 presents molecular models of three anti-(+)METH mAb. Upper panel: Stereo view of superimposed molecular models of anti-(+)METH mAb. The variable regions of the three mAb were modeled, structurally aligned and represented in cartoon format. The framework residues are represented in blue. The CDR regions are colored according to mAb: mAb6H4, blue; mAb6H8, red; mAb4G9, green. The heavy chain, light chain, and CDR regions are labeled. Lower panel: RMSD (Å) of CDRs from the main chain conformation of mAb6H4.

The present invention provides hapten compounds that may be used to elicit an immune response to one or more of (+)methamphetamine, (+)amphetamine, or (+)MDMA. In particular, the present invention provides compounds that may be used to generate antibodies that recognize one or more of (+)methamphetamine, (+)amphetamine, or (+)MDMA. Advantageously, the compounds of the present invention may be used to generate antibodies that recognize at least one or more of (+)methamphetamine, (+)amphetamine, or (+)MDMA, and that do not substantially cross-react with (−)methamphetamine, (−)amphetamine, or (−)MDMA, or over the counter medications I. Hapten Compounds One aspect of the invention encompasses a hapten compound that comprises either (+) or (−)methamphetamine or (+) or (−)amphetamine conjugated to a linker. Generally speaking, the hapten compound is designed to elicit an immune response in a subject that generates antibodies that recognize one or more of (+)methamphetamine, (+)amphetamine, or (+)3,4-methylenedioxymethamphetamine ((+)MDMA). In a certain embodiments, the hapten compound is designed to generate antibodies that recognize at least two compounds from the group consisting of (+)methamphetamine, (+)amphetamine, and (+)MDMA. In an exemplary embodiment, the compound is designed to generate antibodies that recognize all three compounds of the group consisting of (+)methamphetamine, (+)amphetamine, and (+)MDMA.

In one embodiment, the hapten compound has the (+) or (−) isomer of formula (I):

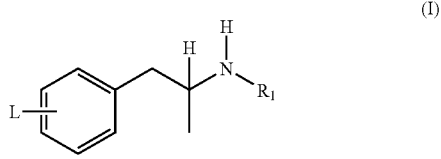

wherein:
$R_1$ is hydrogen or a methyl; and
L is a linker.

In some embodiments, $R_1$ is hydrogen (i.e., forming (+) or (−) amphetamine). In other embodiments, $R_1$ is a methyl group (i.e., forming (+) or (−) methamphetamine). In one embodiment, the compound comprises (+)amphetamine. In another embodiment, the compound comprises (−)amphetamine. In an alternative embodiment, the compound comprises (+)methamphetamine. In another alternative, the compound comprises (−)methamphetamine.

In general, L is comprised of atoms and is of a sufficient length so that L is flexible enough to facilitate an orientation of the (+) or (−)methamphetamine or the (+) or (−)amphetamine sufficient to generate desired antibodies. In this context, "desired" antibodies include antibodies that recognize (+)methamphetamine, (+)amphetamine, or (+)MDMA. L is also typically not strongly immunogenic. In other words, L may be designed so that antibodies generated against a compound of the invention recognize the compound and not merely L.

The exact length of L can and will vary. Typically, L is at least 10 angstroms long. In other embodiment, L may be from about 10 angstroms to about 27 or more angstroms long. In another embodiment, L is at least 11 angstroms, at least 12 angstroms, at least 13 angstroms, at least 14 angstroms, at least 15 angstroms, at least 16 angstroms, at least 17 angstroms, at least 18 angstroms, at least 19 angstroms, at least 20 angstroms, at least 21 angstroms, at least 22 angstroms, at least 23 angstroms, at least 24 angstroms, at least 25 angstroms, at least 26 angstroms, or at least 27 angstroms. The length of the linker when expressed in angstroms may be determined by performing a modeling study, using, for instance, the MM94 force field. Stated another way, the length of L may be expressed as the number of contiguous atoms forming the shortest path from one substructure that L connects to the other substructure. In one embodiment, L is at least 8 contiguous atoms in length. In another embodiment, L may be from about 8 to about 100 or more atoms in length. In an additional embodiment, L is 8, 9, 10, 11, 12, 13, 14, 15, 16, 17, 18, 19, 20, 21, 22, 23, 24, 25, 26, 27, 28, 29, or 30 or more contiguous atoms in length. In certain embodiments, if L is comprised of less than 13 contiguous atoms, then the last atom of the linker opposite its point of attachment to the benzene ring of the compound does not form a carboxylic acid.

As will be appreciated by a skilled artisan, the atoms comprising L may vary widely. Typically, the atoms impart the appropriate degree of flexibility, as detailed above. Suitable atoms forming L may be selected from the group comprising hydrogen, hydrocarbyl, substituted hydrocarbyls, and heteroatoms. In some embodiments, L may be comprised of amino acids, such as glycine or proline. For instance, L may be a peptide. In other embodiments, L may be comprised of nucleotides. In further embodiments, L may be linear, branched, or may comprise ring structures.

It is also envisioned that L may be attached to the benzene ring of (+) or (−)methamphetamine or (+) or (−)amphetamine at a variety of positions without departing from the scope of the invention. For example, in one embodiment, L may be attached at the meta position of the benzene ring as shown in formula (XI):

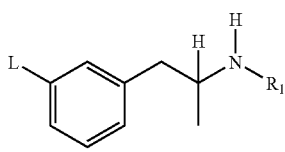

(XI)

wherein:

L and $R_1$ have the same substituents as detailed for compounds corresponding to formula (I).

In another embodiment, L may be attached at the ortho position as shown in formula (XII):

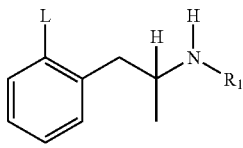

(XII)

wherein:

L and $R_1$ have the same substituents as detailed for compounds corresponding to formula (I).

In yet another embodiment, L may be attached at the para position as shown in formula (XIII):

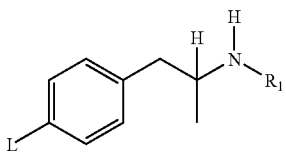

(XIII)

wherein:

L and $R_1$ have the same substituents as detailed for compounds corresponding to formula (I).

Exemplary embodiments of L may be comprised of

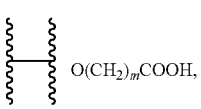

$(CH_2)_m COOH$, wherein m is an integer between about 11 and about 30;

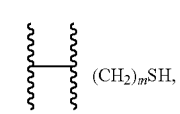

$O(CH_2)_m COOH$, wherein m is an integer between about 10 and about 30;

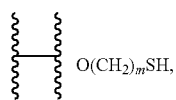

$(CH_2)_m SH$, wherein m is an integer between about 7 and about 30;

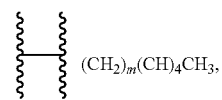

$O(CH_2)_m SH$, wherein m is an integer between about 6 and about 30;

$(CH_2)_m (CH)_4 CH_3$, wherein m is an integer between about 3 and about 30;

$O(CH_2)_m (CH)_4 CH_3$, wherein m is an integer between about 2 and about 30. In an alternative embodiment, L may be comprised of a group listed in Table A.

TABLE A

| L Group | Position on Benzene Ring |
|---|---|
| —$(CH_2)_7 NH_2$ | Para |
| —$(CH_2)_7 NH_2$ | Meta |
| —$(CH_2)_7 NH_2$ | Ortho |
| —$(CH_2)_8 NH_2$ | Para |
| —$(CH_2)_8 NH_2$ | Meta |
| —$(CH_2)_8 NH_2$ | Ortho |
| —$(CH_2)_9 NH_2$ | Para |
| —$(CH_2)_9 NH_2$ | Meta |
| —$(CH_2)_9 NH_2$ | Ortho |
| —$(CH_2)_{10} NH_2$ | Para |
| —$(CH_2)_{10} NH_2$ | Meta |
| —$(CH_2)_{10} NH_2$ | Ortho |
| —$(CH_2)_{11} NH_2$ | Para |
| —$(CH_2)_{11} NH_2$ | Meta |
| —$(CH_2)_{11} NH_2$ | Ortho |
| —$(CH_2)_{12} NH_2$ | Para |
| —$(CH_2)_{12} NH_2$ | Meta |
| —$(CH_2)_{12} NH_2$ | Ortho |
| —$(CH_2)_{13} NH_2$ | Para |
| —$(CH_2)_{13} NH_2$ | Meta |
| —$(CH_2)_{13} NH_2$ | Ortho |
| —$(CH_2)_{14} NH_2$ | Para |
| —$(CH_2)_{14} NH_2$ | Meta |
| —$(CH_2)_{14} NH_2$ | Ortho |
| —$(CH_2)_{15} NH_2$ | Para |
| —$(CH_2)_{15} NH_2$ | Meta |
| —$(CH_2)_{15} NH_2$ | Ortho |
| —$(CH_2)_{16} NH_2$ | Para |
| —$(CH_2)_{16} NH_2$ | Meta |
| —$(CH_2)_{16} NH_2$ | Ortho |
| —$(CH_2)_{17} NH_2$ | Para |
| —$(CH_2)_{17} NH_2$ | Meta |
| —$(CH_2)_{17} NH_2$ | Ortho |
| —$(CH_2)_{18} NH_2$ | Para |
| —$(CH_2)_{18} NH_2$ | Meta |
| —$(CH_2)_{18} NH_2$ | Ortho |
| —$(CH_2)_{19} NH_2$ | Para |
| —$(CH_2)_{19} NH_2$ | Meta |
| —$(CH_2)_{19} NH_2$ | Ortho |
| —$(CH_2)_{20} NH_2$ | Para |
| —$(CH_2)_{20} NH_2$ | Meta |
| —$(CH_2)_{20} NH_2$ | Ortho |
| —$(CH_2)_{21} NH_2$ | Para |
| —$(CH_2)_{21} NH_2$ | Meta |
| —$(CH_2)_{21} NH_2$ | Ortho |
| —$(CH_2)_{22} NH_2$ | Para |

TABLE A-continued

| L Group | Position on Benzene Ring |
|---|---|
| —(CH$_2$)$_{22}$NH$_2$ | Meta |
| —(CH$_2$)$_{22}$NH$_2$ | Ortho |
| —(CH$_2$)$_{23}$NH$_2$ | Para |
| —(CH$_2$)$_{23}$NH$_2$ | Meta |
| —(CH$_2$)$_{23}$NH$_2$ | Ortho |
| —(CH$_2$)$_{24}$NH$_2$ | Para |
| —(CH$_2$)$_{24}$NH$_2$ | Meta |
| —(CH$_2$)$_{24}$NH$_2$ | Ortho |
| —(CH$_2$)$_{25}$NH$_2$ | Para |
| —(CH$_2$)$_{25}$NH$_2$ | Meta |
| —(CH$_2$)$_{25}$NH$_2$ | Ortho |
| —(CH$_2$)$_{26}$NH$_2$ | Para |
| —(CH$_2$)$_{26}$NH$_2$ | Meta |
| —(CH$_2$)$_{26}$NH$_2$ | Ortho |
| —(CH$_2$)$_{27}$NH$_2$ | Para |
| —(CH$_2$)$_{27}$NH$_2$ | Meta |
| —(CH$_2$)$_{27}$NH$_2$ | Ortho |
| —(CH$_2$)$_{28}$NH$_2$ | Para |
| —(CH$_2$)$_{28}$NH$_2$ | Meta |
| —(CH$_2$)$_{28}$NH$_2$ | Ortho |
| —(CH$_2$)$_{29}$NH$_2$ | Para |
| —(CH$_2$)$_{29}$NH$_2$ | Meta |
| —(CH$_2$)$_{29}$NH$_2$ | Ortho |
| —(CH$_2$)$_{30}$NH$_2$ | Para |
| —(CH$_2$)$_{30}$NH$_2$ | Meta |
| —(CH$_2$)$_{30}$NH$_2$ | Ortho |
| —(CH$_2$)$_7$OH | Para |
| —(CH$_2$)$_7$OH | Meta |
| —(CH$_2$)$_7$OH | Ortho |
| —(CH$_2$)$_8$OH | Para |
| —(CH$_2$)$_8$OH | Meta |
| —(CH$_2$)$_8$OH | Ortho |
| —(CH$_2$)$_9$OH | Para |
| —(CH$_2$)$_9$OH | Meta |
| —(CH$_2$)$_9$OH | Ortho |
| —(CH$_2$)$_{10}$OH | Para |
| —(CH$_2$)$_{10}$OH | Meta |
| —(CH$_2$)$_{10}$OH | Ortho |
| —(CH$_2$)$_{11}$OH | Para |
| —(CH$_2$)$_{11}$OH | Meta |
| —(CH$_2$)$_{11}$OH | Ortho |
| —(CH$_2$)$_{12}$OH | Para |
| —(CH$_2$)$_{12}$OH | Meta |
| —(CH$_2$)$_{12}$OH | Ortho |
| —(CH$_2$)$_{13}$OH | Para |
| —(CH$_2$)$_{13}$OH | Meta |
| —(CH$_2$)$_{13}$OH | Ortho |
| —(CH$_2$)$_{14}$OH | Para |
| —(CH$_2$)$_{14}$OH | Meta |
| —(CH$_2$)$_{14}$OH | Ortho |
| —(CH$_2$)$_{15}$OH | Para |
| —(CH$_2$)$_{15}$OH | Meta |
| —(CH$_2$)$_{15}$OH | Ortho |
| —(CH$_2$)$_{16}$OH | Para |
| —(CH$_2$)$_{16}$OH | Meta |
| —(CH$_2$)$_{16}$OH | Ortho |
| —(CH$_2$)$_{17}$OH | Para |
| —(CH$_2$)$_{17}$OH | Meta |
| —(CH$_2$)$_{17}$OH | Ortho |
| —(CH$_2$)$_{18}$OH | Para |
| —(CH$_2$)$_{18}$OH | Meta |
| —(CH$_2$)$_{18}$OH | Ortho |
| —(CH$_2$)$_{19}$OH | Para |
| —(CH$_2$)$_{19}$OH | Meta |
| —(CH$_2$)$_{19}$OH | Ortho |
| —(CH$_2$)$_{20}$OH | Para |
| —(CH$_2$)$_{20}$OH | Meta |
| —(CH$_2$)$_{20}$OH | Ortho |
| —(CH$_2$)$_{21}$OH | Para |
| —(CH$_2$)$_{21}$OH | Meta |
| —(CH$_2$)$_{21}$OH | Ortho |
| —(CH$_2$)$_{22}$OH | Para |
| —(CH$_2$)$_{22}$OH | Meta |
| —(CH$_2$)$_{22}$OH | Ortho |
| —(CH$_2$)$_{23}$OH | Para |
| —(CH$_2$)$_{23}$OH | Meta |
| —(CH$_2$)$_{23}$OH | Ortho |
| —(CH$_2$)$_{24}$OH | Para |
| —(CH$_2$)$_{24}$OH | Meta |
| —(CH$_2$)$_{24}$OH | Ortho |
| —(CH$_2$)$_{25}$OH | Para |
| —(CH$_2$)$_{25}$OH | Meta |
| —(CH$_2$)$_{25}$OH | Ortho |
| —(CH$_2$)$_{26}$OH | Para |
| —(CH$_2$)$_{26}$OH | Meta |
| —(CH$_2$)$_{26}$OH | Ortho |
| —(CH$_2$)$_{27}$OH | Para |
| —(CH$_2$)$_{27}$OH | Meta |
| —(CH$_2$)$_{27}$OH | Ortho |
| —(CH$_2$)$_{28}$OH | Para |
| —(CH$_2$)$_{28}$OH | Meta |
| —(CH$_2$)$_{28}$OH | Ortho |
| —(CH$_2$)$_{29}$OH | Para |
| —(CH$_2$)$_{29}$OH | Meta |
| —(CH$_2$)$_{29}$OH | Ortho |
| —(CH$_2$)$_{30}$OH | Para |
| —(CH$_2$)$_{30}$OH | Meta |
| —(CH$_2$)$_{30}$OH | Ortho |
| —(CH$_2$)$_7$SH | Para |
| —(CH$_2$)$_7$SH | Meta |
| —(CH$_2$)$_7$SH | Ortho |
| —(CH$_2$)$_8$SH | Para |
| —(CH$_2$)$_8$SH | Meta |
| —(CH$_2$)$_8$SH | Ortho |
| —(CH$_2$)$_9$SH | Para |
| —(CH$_2$)$_9$SH | Meta |
| —(CH$_2$)$_9$SH | Ortho |
| —(CH$_2$)$_{10}$SH | Para |
| —(CH$_2$)$_{10}$SH | Meta |
| —(CH$_2$)$_{10}$SH | Ortho |
| —(CH$_2$)$_{11}$SH | Para |
| —(CH$_2$)$_{11}$SH | Meta |
| —(CH$_2$)$_{11}$SH | Ortho |
| —(CH$_2$)$_{12}$SH | Para |
| —(CH$_2$)$_{12}$SH | Meta |
| —(CH$_2$)$_{12}$SH | Ortho |
| —(CH$_2$)$_{13}$SH | Para |
| —(CH$_2$)$_{13}$SH | Meta |
| —(CH$_2$)$_{13}$SH | Ortho |
| —(CH$_2$)$_{14}$SH | Para |
| —(CH$_2$)$_{14}$SH | Meta |
| —(CH$_2$)$_{14}$SH | Ortho |
| —(CH$_2$)$_{15}$SH | Para |
| —(CH$_2$)$_{15}$SH | Meta |
| —(CH$_2$)$_{15}$SH | Ortho |
| —(CH$_2$)$_{16}$SH | Para |
| —(CH$_2$)$_{16}$SH | Meta |
| —(CH$_2$)$_{16}$SH | Ortho |
| —(CH$_2$)$_{17}$SH | Para |
| —(CH$_2$)$_{17}$SH | Meta |
| —(CH$_2$)$_{17}$SH | Ortho |
| —(CH$_2$)$_{18}$SH | Para |
| —(CH$_2$)$_{18}$SH | Meta |
| —(CH$_2$)$_{18}$SH | Ortho |
| —(CH$_2$)$_{19}$SH | Para |
| —(CH$_2$)$_{19}$SH | Meta |
| —(CH$_2$)$_{19}$SH | Ortho |
| —(CH$_2$)$_{20}$SH | Para |
| —(CH$_2$)$_{20}$SH | Meta |
| —(CH$_2$)$_{20}$SH | Ortho |
| —(CH$_2$)$_{21}$SH | Para |
| —(CH$_2$)$_{21}$SH | Meta |
| —(CH$_2$)$_{21}$SH | Ortho |
| —(CH$_2$)$_{22}$SH | Para |
| —(CH$_2$)$_{22}$SH | Meta |
| —(CH$_2$)$_{22}$SH | Ortho |
| —(CH$_2$)$_{23}$SH | Para |
| —(CH$_2$)$_{23}$SH | Meta |
| —(CH$_2$)$_{23}$SH | Ortho |
| —(CH$_2$)$_{24}$SH | Para |
| —(CH$_2$)$_{24}$SH | Meta |
| —(CH$_2$)$_{24}$SH | Ortho |
| —(CH$_2$)$_{25}$SH | Para |
| —(CH$_2$)$_{25}$SH | Meta |
| —(CH$_2$)$_{25}$SH | Ortho |
| —(CH$_2$)$_{26}$SH | Para |

TABLE A-continued

| L Group | Position on Benzene Ring |
|---|---|
| —(CH$_2$)$_{26}$SH | Meta |
| —(CH$_2$)$_{26}$SH | Ortho |
| —(CH$_2$)$_{27}$SH | Para |
| —(CH$_2$)$_{27}$SH | Meta |
| —(CH$_2$)$_{27}$SH | Ortho |
| —(CH$_2$)$_{28}$SH | Para |
| —(CH$_2$)$_{28}$SH | Meta |
| —(CH$_2$)$_{28}$SH | Ortho |
| —(CH$_2$)$_{29}$SH | Para |
| —(CH$_2$)$_{29}$SH | Meta |
| —(CH$_2$)$_{29}$SH | Ortho |
| —(CH$_2$)$_{30}$SH | Para |
| —(CH$_2$)$_{30}$SH | Meta |
| —(CH$_2$)$_{30}$SH | Ortho |
| —(CH$_2$)$_{11}$COOH | Para |
| —(CH$_2$)$_{11}$COOH | Meta |
| —(CH$_2$)$_{11}$COOH | Ortho |
| —(CH$_2$)$_{12}$COOH | Para |
| —(CH$_2$)$_{12}$COOH | Meta |
| —(CH$_2$)$_{12}$COOH | Ortho |
| —(CH$_2$)$_{13}$COOH | Para |
| —(CH$_2$)$_{13}$COOH | Meta |
| —(CH$_2$)$_{13}$COOH | Ortho |
| —(CH$_2$)$_{14}$COOH | Para |
| —(CH$_2$)$_{14}$COOH | Meta |
| —(CH$_2$)$_{14}$COOH | Ortho |
| —(CH$_2$)$_{15}$COOH | Para |
| —(CH$_2$)$_{15}$COOH | Meta |
| —(CH$_2$)$_{15}$COOH | Ortho |
| —(CH$_2$)$_{16}$COOH | Para |
| —(CH$_2$)$_{16}$COOH | Meta |
| —(CH$_2$)$_{16}$COOH | Ortho |
| —(CH$_2$)$_{17}$COOH | Para |
| —(CH$_2$)$_{17}$COOH | Meta |
| —(CH$_2$)$_{17}$COOH | Ortho |
| —(CH$_2$)$_{18}$COOH | Para |
| —(CH$_2$)$_{18}$COOH | Meta |
| —(CH$_2$)$_{18}$COOH | Ortho |
| —(CH$_2$)$_{19}$COOH | Para |
| —(CH$_2$)$_{19}$COOH | Meta |
| —(CH$_2$)$_{19}$COOH | Ortho |
| —(CH$_2$)$_{20}$COOH | Para |
| —(CH$_2$)$_{20}$COOH | Meta |
| —(CH$_2$)$_{20}$COOH | Ortho |
| —(CH$_2$)$_{21}$COOH | Para |
| —(CH$_2$)$_{21}$COOH | Meta |
| —(CH$_2$)$_{21}$COOH | Ortho |
| —(CH$_2$)$_{22}$COOH | Para |
| —(CH$_2$)$_{22}$COOH | Meta |
| —(CH$_2$)$_{22}$COOH | Ortho |
| —(CH$_2$)$_{23}$COOH | Para |
| —(CH$_2$)$_{23}$COOH | Meta |
| —(CH$_2$)$_{23}$COOH | Ortho |
| —(CH$_2$)$_{24}$COOH | Para |
| —(CH$_2$)$_{24}$COOH | Meta |
| —(CH$_2$)$_{24}$COOH | Ortho |
| —(CH$_2$)$_{25}$COOH | Para |
| —(CH$_2$)$_{25}$COOH | Meta |
| —(CH$_2$)$_{25}$COOH | Ortho |
| —(CH$_2$)$_{26}$COOH | Para |
| —(CH$_2$)$_{26}$COOH | Meta |
| —(CH$_2$)$_{26}$COOH | Ortho |
| —(CH$_2$)$_{27}$COOH | Para |
| —(CH$_2$)$_{27}$COOH | Meta |
| —(CH$_2$)$_{27}$COOH | Ortho |
| —(CH$_2$)$_{28}$COOH | Para |
| —(CH$_2$)$_{28}$COOH | Meta |
| —(CH$_2$)$_{28}$COOH | Ortho |
| —(CH$_2$)$_{29}$COOH | Para |
| —(CH$_2$)$_{29}$COOH | Meta |
| —(CH$_2$)$_{29}$COOH | Ortho |
| —(CH$_2$)$_{30}$COOH | Para |
| —(CH$_2$)$_{30}$COOH | Meta |
| —(CH$_2$)$_{30}$COOH | Ortho |
| —O(CH$_2$)$_6$NH$_2$ | Para |
| —O(CH$_2$)$_6$NH$_2$ | Meta |
| —O(CH$_2$)$_6$NH$_2$ | Ortho |
| —O(CH$_2$)$_7$NH$_2$ | Para |
| —O(CH$_2$)$_7$NH$_2$ | Meta |
| —O(CH$_2$)$_7$NH$_2$ | Ortho |
| —O(CH$_2$)$_8$NH$_2$ | Para |
| —O(CH$_2$)$_8$NH$_2$ | Meta |
| —O(CH$_2$)$_8$NH$_2$ | Ortho |
| —O(CH$_2$)$_9$NH$_2$ | Para |
| —O(CH$_2$)$_9$NH$_2$ | Meta |
| —O(CH$_2$)$_9$NH$_2$ | Ortho |
| —O(CH$_2$)$_{10}$NH$_2$ | Para |
| —O(CH$_2$)$_{10}$NH$_2$ | Meta |
| —O(CH$_2$)$_{10}$NH$_2$ | Ortho |
| —O(CH$_2$)$_{11}$NH$_2$ | Para |
| —O(CH$_2$)$_{11}$NH$_2$ | Meta |
| —O(CH$_2$)$_{11}$NH$_2$ | Ortho |
| —O(CH$_2$)$_{12}$NH$_2$ | Para |
| —O(CH$_2$)$_{12}$NH$_2$ | Meta |
| —O(CH$_2$)$_{12}$NH$_2$ | Ortho |
| —O(CH$_2$)$_{13}$NH$_2$ | Para |
| —O(CH$_2$)$_{13}$NH$_2$ | Meta |
| —O(CH$_2$)$_{13}$NH$_2$ | Ortho |
| —O(CH$_2$)$_{14}$NH$_2$ | Para |
| —O(CH$_2$)$_{14}$NH$_2$ | Meta |
| —O(CH$_2$)$_{14}$NH$_2$ | Ortho |
| —O(CH$_2$)$_{15}$NH$_2$ | Para |
| —O(CH$_2$)$_{15}$NH$_2$ | Meta |
| —O(CH$_2$)$_{15}$NH$_2$ | Ortho |
| —O(CH$_2$)$_{16}$NH$_2$ | Para |
| —O(CH$_2$)$_{16}$NH$_2$ | Meta |
| —O(CH$_2$)$_{16}$NH$_2$ | Ortho |
| —O(CH$_2$)$_{17}$NH$_2$ | Para |
| —O(CH$_2$)$_{17}$NH$_2$ | Meta |
| —O(CH$_2$)$_{17}$NH$_2$ | Ortho |
| —O(CH$_2$)$_{18}$NH$_2$ | Para |
| —O(CH$_2$)$_{18}$NH$_2$ | Meta |
| —O(CH$_2$)$_{18}$NH$_2$ | Ortho |
| —O(CH$_2$)$_{19}$NH$_2$ | Para |
| —O(CH$_2$)$_{19}$NH$_2$ | Meta |
| —O(CH$_2$)$_{19}$NH$_2$ | Ortho |
| —O(CH$_2$)$_{20}$NH$_2$ | Para |
| —O(CH$_2$)$_{20}$NH$_2$ | Meta |
| —O(CH$_2$)$_{20}$NH$_2$ | Ortho |
| —O(CH$_2$)$_{21}$NH$_2$ | Para |
| —O(CH$_2$)$_{21}$NH$_2$ | Meta |
| —O(CH$_2$)$_{21}$NH$_2$ | Ortho |
| —O(CH$_2$)$_{22}$NH$_2$ | Para |
| —O(CH$_2$)$_{22}$NH$_2$ | Meta |
| —O(CH$_2$)$_{22}$NH$_2$ | Ortho |
| —O(CH$_2$)$_{23}$NH$_2$ | Para |
| —O(CH$_2$)$_{23}$NH$_2$ | Meta |
| —O(CH$_2$)$_{23}$NH$_2$ | Ortho |
| —O(CH$_2$)$_{24}$NH$_2$ | Para |
| —O(CH$_2$)$_{24}$NH$_2$ | Meta |
| —O(CH$_2$)$_{24}$NH$_2$ | Ortho |
| —O(CH$_2$)$_{25}$NH$_2$ | Para |
| —O(CH$_2$)$_{25}$NH$_2$ | Meta |
| —O(CH$_2$)$_{25}$NH$_2$ | Ortho |
| —O(CH$_2$)$_{26}$NH$_2$ | Para |
| —O(CH$_2$)$_{26}$NH$_2$ | Meta |
| —O(CH$_2$)$_{26}$NH$_2$ | Ortho |
| —O(CH$_2$)$_{27}$NH$_2$ | Para |
| —O(CH$_2$)$_{27}$NH$_2$ | Meta |
| —O(CH$_2$)$_{27}$NH$_2$ | Ortho |
| —O(CH$_2$)$_{28}$NH$_2$ | Para |
| —O(CH$_2$)$_{28}$NH$_2$ | Meta |
| —O(CH$_2$)$_{28}$NH$_2$ | Ortho |
| —O(CH$_2$)$_{29}$NH$_2$ | Para |
| —O(CH$_2$)$_{29}$NH$_2$ | Meta |
| —O(CH$_2$)$_{29}$NH$_2$ | Ortho |
| —O(CH$_2$)$_{30}$NH$_2$ | Para |
| —O(CH$_2$)$_{30}$NH$_2$ | Meta |
| —O(CH$_2$)$_{30}$NH$_2$ | Ortho |
| —O(CH$_2$)$_6$OH | Para |
| —O(CH$_2$)$_6$OH | Meta |
| —O(CH$_2$)$_6$OH | Ortho |
| —O(CH$_2$)$_7$OH | Para |
| —O(CH$_2$)$_7$OH | Meta |
| —O(CH$_2$)$_7$OH | Ortho |
| —O(CH$_2$)$_8$OH | Para |

TABLE A-continued

| L Group | Position on Benzene Ring |
|---|---|
| —O(CH$_2$)$_8$OH | Meta |
| —O(CH$_2$)$_8$OH | Ortho |
| —O(CH$_2$)$_9$OH | Para |
| —O(CH$_2$)$_9$OH | Meta |
| —O(CH$_2$)$_9$OH | Ortho |
| —O(CH$_2$)$_{10}$OH | Para |
| —O(CH$_2$)$_{10}$OH | Meta |
| —O(CH$_2$)$_{10}$OH | Ortho |
| —O(CH$_2$)$_{10}$OH | Para |
| —O(CH$_2$)$_{11}$OH | Meta |
| —O(CH$_2$)$_{11}$OH | Ortho |
| —O(CH$_2$)$_{12}$OH | Para |
| —O(CH$_2$)$_{12}$OH | Meta |
| —O(CH$_2$)$_{12}$OH | Ortho |
| —O(CH$_2$)$_{13}$OH | Para |
| —O(CH$_2$)$_{13}$OH | Meta |
| —O(CH$_2$)$_{13}$OH | Ortho |
| —O(CH$_2$)$_{14}$OH | Para |
| —O(CH$_2$)$_{14}$OH | Meta |
| —O(CH$_2$)$_{14}$OH | Ortho |
| —O(CH$_2$)$_{15}$OH | Para |
| —O(CH$_2$)$_{15}$OH | Meta |
| —O(CH$_2$)$_{15}$OH | Ortho |
| —O(CH$_2$)$_{16}$OH | Para |
| —O(CH$_2$)$_{16}$OH | Meta |
| —O(CH$_2$)$_{16}$OH | Ortho |
| —O(CH$_2$)$_{17}$OH | Para |
| —O(CH$_2$)$_{17}$OH | Meta |
| —O(CH$_2$)$_{17}$OH | Ortho |
| —O(CH$_2$)$_{18}$OH | Para |
| —O(CH$_2$)$_{18}$OH | Meta |
| —O(CH$_2$)$_{18}$OH | Ortho |
| —O(CH$_2$)$_{19}$OH | Para |
| —O(CH$_2$)$_{19}$OH | Meta |
| —O(CH$_2$)$_{19}$OH | Ortho |
| —O(CH$_2$)$_{20}$OH | Para |
| —O(CH$_2$)$_{20}$OH | Meta |
| —O(CH$_2$)$_{20}$OH | Ortho |
| —O(CH$_2$)$_{21}$OH | Para |
| —O(CH$_2$)$_{21}$OH | Meta |
| —O(CH$_2$)$_{21}$OH | Ortho |
| —O(CH$_2$)$_{22}$OH | Para |
| —O(CH$_2$)$_{22}$OH | Meta |
| —O(CH$_2$)$_{22}$OH | Ortho |
| —O(CH$_2$)$_{23}$OH | Para |
| —O(CH$_2$)$_{23}$OH | Meta |
| —O(CH$_2$)$_{23}$OH | Ortho |
| —O(CH$_2$)$_{24}$OH | Para |
| —O(CH$_2$)$_{24}$OH | Meta |
| —O(CH$_2$)$_{24}$OH | Ortho |
| —O(CH$_2$)$_{25}$OH | Para |
| —O(CH$_2$)$_{25}$OH | Meta |
| —O(CH$_2$)$_{25}$OH | Ortho |
| —O(CH$_2$)$_{26}$OH | Para |
| —O(CH$_2$)$_{26}$OH | Meta |
| —O(CH$_2$)$_{26}$OH | Ortho |
| —O(CH$_2$)$_{27}$OH | Para |
| —O(CH$_2$)$_{27}$OH | Meta |
| —O(CH$_2$)$_{27}$OH | Ortho |
| —O(CH$_2$)$_{28}$OH | Para |
| —O(CH$_2$)$_{28}$OH | Meta |
| —O(CH$_2$)$_{28}$OH | Ortho |
| —O(CH$_2$)$_{29}$OH | Para |
| —O(CH$_2$)$_{29}$OH | Meta |
| —O(CH$_2$)$_{29}$OH | Ortho |
| —O(CH$_2$)$_{30}$OH | Para |
| —O(CH$_2$)$_{30}$OH | Meta |
| —O(CH$_2$)$_{30}$OH | Ortho |
| —O(CH$_2$)$_6$SH | Para |
| —O(CH$_2$)$_6$SH | Meta |
| —O(CH$_2$)$_6$SH | Ortho |
| —O(CH$_2$)$_7$SH | Para |
| —O(CH$_2$)$_7$SH | Meta |
| —O(CH$_2$)$_7$SH | Ortho |
| —O(CH$_2$)$_8$SH | Para |
| —O(CH$_2$)$_8$SH | Meta |
| —O(CH$_2$)$_8$SH | Ortho |
| —O(CH$_2$)$_9$SH | Para |
| —O(CH$_2$)$_9$SH | Meta |
| —O(CH$_2$)$_9$SH | Ortho |
| —O(CH$_2$)$_{10}$SH | Para |
| —O(CH$_2$)$_{10}$SH | Meta |
| —O(CH$_2$)$_{10}$SH | Ortho |
| —O(CH$_2$)$_{11}$SH | Para |
| —O(CH$_2$)$_{11}$SH | Meta |
| —O(CH$_2$)$_{11}$SH | Ortho |
| —O(CH$_2$)$_{12}$SH | Para |
| —O(CH$_2$)$_{12}$SH | Meta |
| —O(CH$_2$)$_{12}$SH | Ortho |
| —O(CH$_2$)$_{13}$SH | Para |
| —O(CH$_2$)$_{13}$SH | Meta |
| —O(CH$_2$)$_{13}$SH | Ortho |
| —O(CH$_2$)$_{14}$SH | Para |
| —O(CH$_2$)$_{14}$SH | Meta |
| —O(CH$_2$)$_{14}$SH | Ortho |
| —O(CH$_2$)$_{15}$SH | Para |
| —O(CH$_2$)$_{15}$SH | Meta |
| —O(CH$_2$)$_{15}$SH | Ortho |
| —O(CH$_2$)$_{16}$SH | Para |
| —O(CH$_2$)$_{16}$SH | Meta |
| —O(CH$_2$)$_{16}$SH | Ortho |
| —O(CH$_2$)$_{17}$SH | Para |
| —O(CH$_2$)$_{17}$SH | Meta |
| —O(CH$_2$)$_{17}$SH | Ortho |
| —O(CH$_2$)$_{18}$SH | Para |
| —O(CH$_2$)$_{18}$SH | Meta |
| —O(CH$_2$)$_{18}$SH | Ortho |
| —O(CH$_2$)$_{19}$SH | Para |
| —O(CH$_2$)$_{19}$SH | Meta |
| —O(CH$_2$)$_{19}$SH | Ortho |
| —O(CH$_2$)$_{20}$SH | Para |
| —O(CH$_2$)$_{20}$SH | Meta |
| —O(CH$_2$)$_{20}$SH | Ortho |
| —O(CH$_2$)$_{21}$SH | Para |
| —O(CH$_2$)$_{21}$SH | Meta |
| —O(CH$_2$)$_{21}$SH | Ortho |
| —O(CH$_2$)$_{22}$SH | Para |
| —O(CH$_2$)$_{22}$SH | Meta |
| —O(CH$_2$)$_{22}$SH | Ortho |
| —O(CH$_2$)$_{23}$SH | Para |
| —O(CH$_2$)$_{23}$SH | Meta |
| —O(CH$_2$)$_{23}$SH | Ortho |
| —O(CH$_2$)$_{24}$SH | Para |
| —O(CH$_2$)$_{24}$SH | Meta |
| —O(CH$_2$)$_{24}$SH | Ortho |
| —O(CH$_2$)$_{25}$SH | Para |
| —O(CH$_2$)$_{25}$SH | Meta |
| —O(CH$_2$)$_{25}$SH | Ortho |
| —O(CH$_2$)$_{26}$SH | Para |
| —O(CH$_2$)$_{26}$SH | Meta |
| —O(CH$_2$)$_{26}$SH | Ortho |
| —O(CH$_2$)$_{27}$SH | Para |
| —O(CH$_2$)$_{27}$SH | Meta |
| —O(CH$_2$)$_{27}$SH | Ortho |
| —O(CH$_2$)$_{28}$SH | Para |
| —O(CH$_2$)$_{28}$SH | Meta |
| —O(CH$_2$)$_{28}$SH | Ortho |
| —O(CH$_2$)$_{29}$SH | Para |
| —O(CH$_2$)$_{29}$SH | Meta |
| —O(CH$_2$)$_{29}$SH | Ortho |
| —O(CH$_2$)$_{30}$SH | Para |
| —O(CH$_2$)$_{30}$SH | Meta |
| —O(CH$_2$)$_{30}$SH | Ortho |
| —O(CH$_2$)$_{10}$COOH | Para |
| —O(CH$_2$)$_{10}$COOH | Meta |
| —O(CH$_2$)$_{10}$COOH | Ortho |
| —O(CH$_2$)$_{11}$COOH | Para |
| —O(CH$_2$)$_{11}$COOH | Meta |
| —O(CH$_2$)$_{11}$COOH | Ortho |
| —O(CH$_2$)$_{12}$COOH | Para |
| —O(CH$_2$)$_{12}$COOH | Meta |
| —O(CH$_2$)$_{12}$COOH | Ortho |
| —O(CH$_2$)$_{13}$COOH | Para |
| —O(CH$_2$)$_{13}$COOH | Meta |
| —O(CH$_2$)$_{13}$COOH | Ortho |
| —O(CH$_2$)$_{14}$COOH | Para |

TABLE A-continued

| L Group | Position on Benzene Ring |
|---|---|
| —O(CH$_2$)$_{14}$COOH | Meta |
| —O(CH$_2$)$_{14}$COOH | Ortho |
| —O(CH$_2$)$_{15}$COOH | Para |
| —O(CH$_2$)$_{15}$COOH | Meta |
| —O(CH$_2$)$_{15}$COOH | Ortho |
| —O(CH$_2$)$_{16}$COOH | Para |
| —O(CH$_2$)$_{16}$COOH | Meta |
| —O(CH$_2$)$_{16}$COOH | Ortho |
| —O(CH$_2$)$_{17}$COOH | Para |
| —O(CH$_2$)$_{17}$COOH | Meta |
| —O(CH$_2$)$_{17}$COOH | Ortho |
| —O(CH$_2$)$_{18}$COOH | Para |
| —O(CH$_2$)$_{18}$COOH | Meta |
| —O(CH$_2$)$_{18}$COOH | Ortho |
| —O(CH$_2$)$_{19}$COOH | Para |
| —O(CH$_2$)$_{19}$COOH | Meta |
| —O(CH$_2$)$_{19}$COOH | Ortho |
| —O(CH$_2$)$_{20}$COOH | Para |
| —O(CH$_2$)$_{20}$COOH | Meta |
| —O(CH$_2$)$_{20}$COOH | Ortho |
| —O(CH$_2$)$_{21}$COOH | Para |
| —O(CH$_2$)$_{21}$COOH | Meta |
| —O(CH$_2$)$_{21}$COOH | Ortho |
| —O(CH$_2$)$_{22}$COOH | Para |
| —O(CH$_2$)$_{22}$COOH | Meta |
| —O(CH$_2$)$_{22}$COOH | Ortho |
| —O(CH$_2$)$_{23}$COOH | Para |
| —O(CH$_2$)$_{23}$COOH | Meta |
| —O(CH$_2$)$_{23}$COOH | Ortho |
| —O(CH$_2$)$_{24}$COOH | Para |
| —O(CH$_2$)$_{24}$COOH | Meta |
| —O(CH$_2$)$_{24}$COOH | Ortho |
| —O(CH$_2$)$_{25}$COOH | Para |
| —O(CH$_2$)$_{25}$COOH | Meta |
| —O(CH$_2$)$_{25}$COOH | Ortho |
| —O(CH$_2$)$_{26}$COOH | Para |
| —O(CH$_2$)$_{26}$COOH | Meta |
| —O(CH$_2$)$_{26}$COOH | Ortho |
| —O(CH$_2$)$_{27}$COOH | Para |
| —O(CH$_2$)$_{27}$COOH | Meta |
| —O(CH$_2$)$_{27}$COOH | Ortho |
| —O(CH$_2$)$_{28}$COOH | Para |
| —O(CH$_2$)$_{28}$COOH | Meta |
| —O(CH$_2$)$_{28}$COOH | Ortho |
| —O(CH$_2$)$_{29}$COOH | Para |
| —O(CH$_2$)$_{29}$COOH | Meta |
| —O(CH$_2$)$_{29}$COOH | Ortho |
| —O(CH$_2$)$_{30}$COOH | Para |
| —O(CH$_2$)$_{30}$COOH | Meta |
| —O(CH$_2$)$_{30}$COOH | Ortho |
| ‡—X$_7$NH$_2$ | Para |
| ‡—X$_7$NH$_2$ | Meta |
| ‡—X$_7$NH$_2$ | Ortho |
| ‡—X$_8$NH$_2$ | Para |
| ‡—X$_8$NH$_2$ | Meta |
| ‡—X$_8$NH$_2$ | Ortho |
| ‡—X$_9$NH$_2$ | Para |
| ‡—X$_9$NH$_2$ | Meta |
| ‡—X$_9$NH$_2$ | Ortho |
| ‡—X$_{10}$NH$_2$ | Para |
| ‡—X$_{10}$NH$_2$ | Meta |
| ‡—X$_{10}$NH$_2$ | Ortho |
| ‡—X$_{11}$NH$_2$ | Para |
| ‡—X$_{11}$NH$_2$ | Meta |
| ‡—X$_{11}$NH$_2$ | Ortho |
| ‡—X$_{12}$NH$_2$ | Para |
| ‡—X$_{12}$NH$_2$ | Meta |
| ‡—X$_{12}$NH$_2$ | Ortho |
| ‡—X$_{13}$NH$_2$ | Para |
| ‡—X$_{13}$NH$_2$ | Meta |
| ‡—X$_{13}$NH$_2$ | Ortho |
| ‡—X$_{14}$NH$_2$ | Para |
| ‡—X$_{14}$NH$_2$ | Meta |
| ‡—X$_{14}$NH$_2$ | Ortho |
| ‡—X$_{15}$NH$_2$ | Para |
| ‡—X$_{15}$NH$_2$ | Meta |
| ‡—X$_{15}$NH$_2$ | Ortho |
| ‡—X$_{16}$NH$_2$ | Para |
| ‡—X$_{16}$NH$_2$ | Meta |
| ‡—X$_{16}$NH$_2$ | Ortho |
| ‡—X$_{17}$NH$_2$ | Para |
| ‡—X$_{17}$NH$_2$ | Meta |
| ‡—X$_{17}$NH$_2$ | Ortho |
| ‡—X$_{18}$NH$_2$ | Para |
| ‡—X$_{18}$NH$_2$ | Meta |
| ‡—X$_{18}$NH$_2$ | Ortho |
| ‡—X$_{19}$NH$_2$ | Para |
| ‡—X$_{19}$NH$_2$ | Meta |
| ‡—X$_{19}$NH$_2$ | Ortho |
| ‡—X$_{20}$NH$_2$ | Para |
| ‡—X$_{20}$NH$_2$ | Meta |
| ‡—X$_{20}$NH$_2$ | Ortho |
| ‡—X$_{21}$NH$_2$ | Para |
| ‡—X$_{21}$NH$_2$ | Meta |
| ‡—X$_{21}$NH$_2$ | Ortho |
| ‡—X$_{22}$NH$_2$ | Para |
| ‡—X$_{22}$NH$_2$ | Meta |
| ‡—X$_{22}$NH$_2$ | Ortho |
| ‡—X$_{23}$NH$_2$ | Para |
| ‡—X$_{23}$NH$_2$ | Meta |
| ‡—X$_{23}$NH$_2$ | Ortho |
| ‡—X$_{24}$NH$_2$ | Para |
| ‡—X$_{24}$NH$_2$ | Meta |
| ‡—X$_{24}$NH$_2$ | Ortho |
| ‡—X$_{25}$NH$_2$ | Para |
| ‡—X$_{25}$NH$_2$ | Meta |
| ‡—X$_{25}$NH$_2$ | Ortho |
| ‡—X$_{26}$NH$_2$ | Para |
| ‡—X$_{26}$NH$_2$ | Meta |
| ‡—X$_{26}$NH$_2$ | Ortho |
| ‡—X$_{27}$NH$_2$ | Para |
| ‡—X$_{27}$NH$_2$ | Meta |
| ‡—X$_{27}$NH$_2$ | Ortho |
| ‡—X$_{28}$NH$_2$ | Para |
| ‡—X$_{28}$NH$_2$ | Meta |
| ‡—X$_{28}$NH$_2$ | Ortho |
| ‡—X$_{29}$NH$_2$ | Para |
| ‡—X$_{29}$NH$_2$ | Meta |
| ‡—X$_{29}$NH$_2$ | Ortho |
| ‡—X$_{30}$NH$_2$ | Para |
| ‡—X$_{30}$NH$_2$ | Meta |
| ‡—X$_{30}$NH$_2$ | Ortho |
| ‡—X$_7$OH | Para |
| ‡—X$_7$OH | Meta |
| ‡—X$_7$OH | Ortho |
| ‡—X$_8$OH | Para |
| ‡—X$_8$OH | Meta |
| ‡—X$_8$OH | Ortho |
| ‡—X$_9$OH | Para |
| ‡—X$_9$OH | Meta |
| ‡—X$_9$OH | Ortho |
| ‡—X$_{10}$OH | Para |
| ‡—X$_{10}$OH | Meta |
| ‡—X$_{10}$OH | Ortho |
| ‡—X$_{11}$OH | Para |
| ‡—X$_{11}$OH | Meta |
| ‡—X$_{11}$OH | Ortho |
| ‡—X$_{12}$OH | Para |
| ‡—X$_{12}$OH | Meta |
| ‡—X$_{12}$OH | Ortho |
| ‡—X$_{13}$OH | Para |
| ‡—X$_{13}$OH | Meta |
| ‡—X$_{13}$OH | Ortho |
| ‡—X$_{14}$OH | Para |
| ‡—X$_{14}$OH | Meta |
| ‡—X$_{14}$OH | Ortho |
| ‡—X$_{15}$OH | Para |
| ‡—X$_{15}$OH | Meta |
| ‡—X$_{15}$OH | Ortho |
| ‡—X$_{16}$OH | Para |
| ‡—X$_{16}$OH | Meta |
| ‡—X$_{16}$OH | Ortho |
| ‡—X$_{17}$OH | Para |
| ‡—X$_{17}$OH | Meta |
| ‡—X$_{17}$OH | Ortho |
| ‡—X$_{18}$OH | Para |

TABLE A-continued

| L Group | Position on Benzene Ring |
|---|---|
| ‡—$X_{18}$OH | Meta |
| ‡—$X_{18}$OH | Ortho |
| ‡—$X_{19}$OH | Para |
| ‡—$X_{19}$OH | Meta |
| ‡—$X_{19}$OH | Ortho |
| ‡—$X_{20}$OH | Para |
| ‡—$X_{20}$OH | Meta |
| ‡—$X_{20}$OH | Ortho |
| ‡—$X_{21}$OH | Para |
| ‡—$X_{21}$OH | Meta |
| ‡—$X_{21}$OH | Ortho |
| ‡—$X_{22}$OH | Para |
| ‡—$X_{22}$OH | Meta |
| ‡—$X_{22}$OH | Ortho |
| ‡—$X_{23}$OH | Para |
| ‡—$X_{23}$OH | Meta |
| ‡—$X_{23}$OH | Ortho |
| ‡—$X_{24}$OH | Para |
| ‡—$X_{24}$OH | Meta |
| ‡—$X_{24}$OH | Ortho |
| ‡—$X_{25}$OH | Para |
| ‡—$X_{25}$OH | Meta |
| ‡—$X_{25}$OH | Ortho |
| ‡—$X_{26}$OH | Para |
| ‡—$X_{26}$OH | Meta |
| ‡—$X_{26}$OH | Ortho |
| ‡—$X_{27}$OH | Para |
| ‡—$X_{27}$OH | Meta |
| ‡—$X_{27}$OH | Ortho |
| ‡—$X_{28}$OH | Para |
| ‡—$X_{28}$OH | Meta |
| ‡—$X_{28}$OH | Ortho |
| ‡—$X_{29}$OH | Para |
| ‡—$X_{29}$OH | Meta |
| ‡—$X_{29}$OH | Ortho |
| ‡—$X_{30}$OH | Para |
| ‡—$X_{30}$OH | Meta |
| ‡—$X_{30}$OH | Ortho |
| ‡—$X_{7}$SH | Para |
| ‡—$X_{7}$SH | Meta |
| ‡—$X_{7}$SH | Ortho |
| ‡—$X_{8}$SH | Para |
| ‡—$X_{8}$SH | Meta |
| ‡—$X_{8}$SH | Ortho |
| ‡—$X_{9}$SH | Para |
| ‡—$X_{9}$SH | Meta |
| ‡—$X_{9}$SH | Ortho |
| ‡—$X_{10}$SH | Para |
| ‡—$X_{10}$SH | Meta |
| ‡—$X_{10}$SH | Ortho |
| ‡—$X_{11}$SH | Para |
| ‡—$X_{11}$SH | Meta |
| ‡—$X_{11}$SH | Ortho |
| ‡—$X_{12}$SH | Para |
| ‡—$X_{12}$SH | Meta |
| ‡—$X_{12}$SH | Ortho |
| ‡—$X_{13}$SH | Para |
| ‡—$X_{13}$SH | Meta |
| ‡—$X_{13}$SH | Ortho |
| ‡—$X_{14}$SH | Para |
| ‡—$X_{14}$SH | Meta |
| ‡—$X_{14}$SH | Ortho |
| ‡—$X_{15}$SH | Para |
| ‡—$X_{15}$SH | Meta |
| ‡—$X_{15}$SH | Ortho |
| ‡—$X_{16}$SH | Para |
| ‡—$X_{16}$SH | Meta |
| ‡—$X_{16}$SH | Ortho |
| ‡—$X_{17}$SH | Para |
| ‡—$X_{17}$SH | Meta |
| ‡—$X_{17}$SH | Ortho |
| ‡—$X_{18}$SH | Para |
| ‡—$X_{18}$SH | Meta |
| ‡—$X_{18}$SH | Ortho |
| ‡—$X_{19}$SH | Para |
| ‡—$X_{19}$SH | Meta |
| ‡—$X_{19}$SH | Ortho |
| ‡—$X_{20}$SH | Para |
| ‡—$X_{20}$SH | Meta |
| ‡—$X_{20}$SH | Ortho |
| ‡—$X_{21}$SH | Para |
| ‡—$X_{21}$SH | Meta |
| ‡—$X_{21}$SH | Ortho |
| ‡—$X_{22}$SH | Para |
| ‡—$X_{22}$SH | Meta |
| ‡—$X_{22}$SH | Ortho |
| ‡—$X_{23}$SH | Para |
| ‡—$X_{23}$SH | Meta |
| ‡—$X_{23}$SH | Ortho |
| ‡—$X_{24}$SH | Para |
| ‡—$X_{24}$SH | Meta |
| ‡—$X_{24}$SH | Ortho |
| ‡—$X_{25}$SH | Para |
| ‡—$X_{25}$SH | Meta |
| ‡—$X_{25}$SH | Ortho |
| ‡—$X_{26}$SH | Para |
| ‡—$X_{26}$SH | Meta |
| ‡—$X_{26}$SH | Ortho |
| ‡—$X_{27}$SH | Para |
| ‡—$X_{27}$SH | Meta |
| ‡—$X_{27}$SH | Ortho |
| ‡—$X_{28}$SH | Para |
| ‡—$X_{28}$SH | Meta |
| ‡—$X_{28}$SH | Ortho |
| ‡—$X_{29}$SH | Para |
| ‡—$X_{29}$SH | Meta |
| ‡—$X_{29}$SH | Ortho |
| ‡—$X_{30}$SH | Para |
| ‡—$X_{30}$SH | Meta |
| ‡—$X_{30}$SH | Ortho |
| ‡—$X_{11}$COOH | Para |
| ‡—$X_{11}$COOH | Meta |
| ‡—$X_{11}$COOH | Ortho |
| ‡—$X_{12}$COOH | Para |
| ‡—$X_{12}$COOH | Meta |
| ‡—$X_{12}$COOH | Ortho |
| ‡—$X_{13}$COOH | Para |
| ‡—$X_{13}$COOH | Meta |
| ‡—$X_{13}$COOH | Ortho |
| ‡—$X_{14}$COOH | Para |
| ‡—$X_{14}$COOH | Meta |
| ‡—$X_{14}$COOH | Ortho |
| ‡—$X_{15}$COOH | Para |
| ‡—$X_{15}$COOH | Meta |
| ‡—$X_{15}$COOH | Ortho |
| ‡—$X_{16}$COOH | Para |
| ‡—$X_{16}$COOH | Meta |
| ‡—$X_{16}$COOH | Ortho |
| ‡—$X_{17}$COOH | Para |
| ‡—$X_{17}$COOH | Meta |
| ‡—$X_{17}$COOH | Ortho |
| ‡—$X_{18}$COOH | Para |
| ‡—$X_{18}$COOH | Meta |
| ‡—$X_{18}$COOH | Ortho |
| ‡—$X_{19}$COOH | Para |
| ‡—$X_{19}$COOH | Meta |
| ‡—$X_{19}$COOH | Ortho |
| ‡—$X_{20}$COOH | Para |
| ‡—$X_{20}$COOH | Meta |
| ‡—$X_{20}$COOH | Ortho |
| ‡—$X_{21}$COOH | Para |
| ‡—$X_{21}$COOH | Meta |
| ‡—$X_{21}$COOH | Ortho |
| ‡—$X_{22}$COOH | Para |
| ‡—$X_{22}$COOH | Meta |
| ‡—$X_{22}$COOH | Ortho |
| ‡—$X_{23}$COOH | Para |
| ‡—$X_{23}$COOH | Meta |
| ‡—$X_{23}$COOH | Ortho |
| ‡—$X_{24}$COOH | Para |
| ‡—$X_{24}$COOH | Meta |
| ‡—$X_{24}$COOH | Ortho |
| ‡—$X_{25}$COOH | Para |
| ‡—$X_{25}$COOH | Meta |
| ‡—$X_{25}$COOH | Ortho |
| ‡—$X_{26}$COOH | Para |

TABLE A-continued

| L Group | Position on Benzene Ring |
| --- | --- |
| ‡—$X_{26}$COOH | Meta |
| ‡—$X_{26}$COOH | Ortho |
| ‡—$X_{27}$COOH | Para |
| ‡—$X_{27}$COOH | Meta |
| ‡—$X_{27}$COOH | Ortho |
| ‡—$X_{28}$COOH | Para |
| ‡—$X_{28}$COOH | Meta |
| ‡—$X_{28}$COOH | Ortho |
| ‡—$X_{29}$COOH | Para |
| ‡—$X_{29}$COOH | Meta |
| ‡—$X_{29}$COOH | Ortho |
| ‡—$X_{30}$COOH | Para |
| ‡—$X_{30}$COOH | Meta |
| ‡—$X_{30}$COOH | Ortho |

‡wherein X may be any atom selected from the group comprising C, O, N, P and S; including the appropriate number of hydrogens to balance charge.

Methods of making hapten compounds of formula (I) are known in the art or are otherwise described herein. For instance, see Byrnes-Blake et al., 2001.

In another embodiment, the hapten compound may have the formula (II):

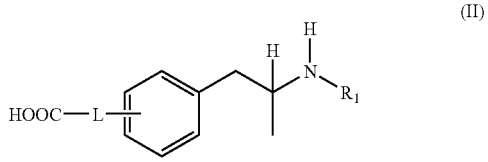

(II)

wherein:

$R_1$ and L are as described for hapten compounds corresponding to formula (I).

In some embodiments for hapten compounds having formula (II), L be comprised of

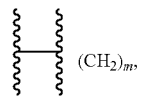

wherein m is an integer between about 11 and about 30. In another alternative of this embodiment, L may be comprised of

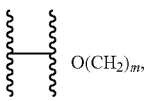

wherein m is an integer between about 10 and about 30.

Figure 11:
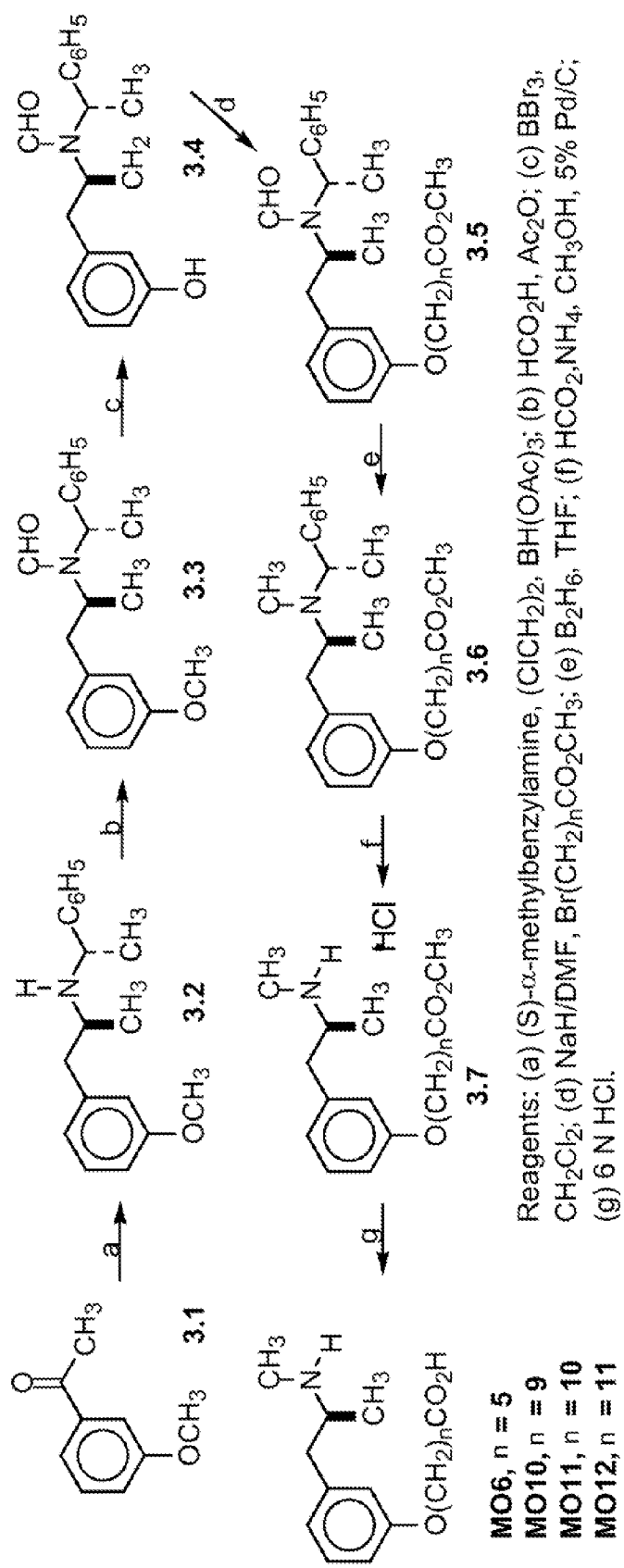
FIG. 11 presents a diagram illustrating the preparation of hapten compounds with carboxylic acid-ending groups.

Methods of making compounds of formula (II) are known in the art. For instance, see FIG. 11 depicting a scheme illustrating the preparation of compounds of the invention with carboxylic acid-ending groups.

In another embodiment, the compound may have formula (III):

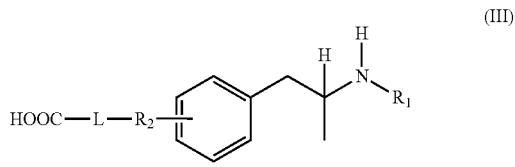

(III)

wherein:

$R_1$ and L are as described for hapten compounds corresponding to formula (I); and $R_2$ may be a heteroatom.

In certain embodiments for compounds corresponding to formula (III), $R_2$ may be a carbon atom, an oxygen atom, a nitrogen atom, a sulfur atom, or a phosphorous atom. In one alternative embodiment, $R_2$ may be a carbon atom. In another alternative embodiment, $R_2$ may be an oxygen atom. In yet another alternative embodiment, $R_2$ may be a nitrogen atom. In still yet another alternative embodiment, $R_2$ may be a phosphorous atom. In an additional alternative embodiment, $R_2$ may be a sulfur atom.

In yet another embodiment, the hapten compound may have the formula (IV):

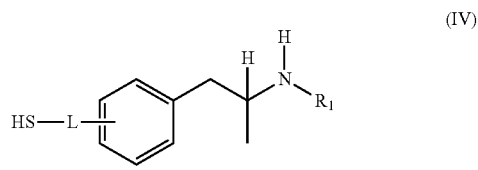

(IV)

wherein:

$R_1$ and L are as described for hapten compounds corresponding to formula (I).

In other embodiments for hapten compounds having formula (IV), L be comprised of

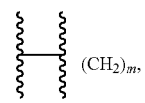

wherein m is an integer between about 7 and about 30. In still other embodiments, L of formula (IV) may be comprised of

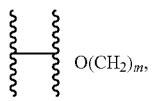

wherein m is an integer between about 6 and about 30.

Figure 12:
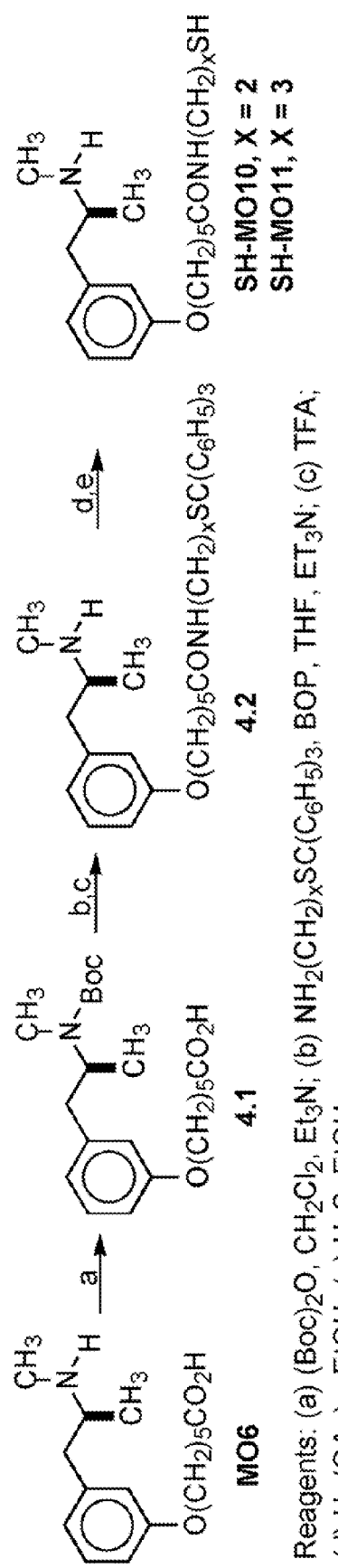
FIG. 12 presents a diagram illustrating the preparation of hapten compounds with mercaptan-ending groups.

Methods of making compounds of formula (IV) are known in the art. For instance, see FIG. 12 depicting a scheme illustrating the preparation of compounds of the invention with mercaptan-ending groups.

In a further embodiment, the hapten compound may have formula (V):

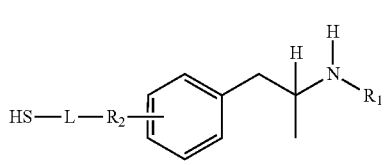

wherein:
R₁ and L are as described for hapten compounds corresponding to formula (I); and
R₂ may be a heteroatom as described above for compounds corresponding to formula (III).

Exemplary hapten compounds having formula (I), (II), (III), (IV), or (V) are shown in Table A.

II. Hapten Compounds Conjugated to Carrier Molecules

In another aspect of the invention, any of the hapten compounds having formulas (I), (II), (III), (IV) or (V) may be conjugated, via a linker, L, to a carrier molecule X. Generally speaking, the carrier molecule is selected so that it enhances the immunogenicity of the hapten compound. For instance, the carrier molecule may provide a T-cell epitope to enhance the immunogenicity of the hapten compound. These compounds may be utilized for a variety of suitable uses including, as a therapeutic immunogenic compound (described in more detail herein), and to elicit the generation of antibodies that may be utilized in passive therapies or in methods of purification or detection.

In one embodiment, a hapten compound corresponding to formula (I) is conjugated via L to a carrier molecule, X, to form a compound having formula (VI):

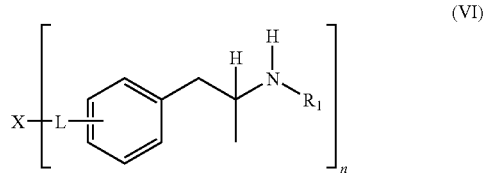

wherein:
R₁ and L are as described for hapten compounds corresponding to formula (I);
X is a carrier molecule that is capable of eliciting an immune response; and
n is an integer greater than or equal to 3.

Typically, X may be a protein, lipid, carbohydrate, or any combination thereof that is capable of eliciting an immune response. For instance, in one embodiment, X may be a polysaccharide, such as mannan. In another embodiment, X may be a lipopolysaccharide, such as a lipopolysaccharide derived from *Salmonella typhosa*.

In exemplary embodiments, X is a protein. In a particular embodiment X may be selected from the group of proteins comprising keyhole limpet hemocyanin (KLH), ovalbumin, bovine serum albumin (BSA), sheep albumin, thyroglobulin, and any modifications, derivatives, or analogues thereof. For instance, in one embodiment, X may be BSA or cationized BSA. In another embodiment, X may be KLH. In yet another embodiment, X may be thyroglobulin.

In another particular embodiment, X may be a bacterial toxin or toxoid. Non-limiting examples of suitable bacterial toxins or toxoids may include tetanus toxoid, diphtheria toxoid, non-toxic mutant diphtheria toxoid $CRM_{197}$, outer membrane protein complex (OMPC) from *Neisseria meningitidis*, the B subunit of heat-labile *Escherichia coli*, recombinant exoprotein A from *Pseudomonas aeruginosa* (rEPA), cholera toxin B-(CTB), pertussis toxin and filamentous hemagglutinin, shiga toxin, and the LTB family of bacterial toxins.

In yet another embodiment, X may be a lectin. Non-limiting examples of suitable lectins may include ricin-B subunit, abrin and sweet pea lectin.

In an alternative embodiment, X may be selected from the group comprising retrovirus nucleoprotein (retro NP), rabies ribonucleoprotein (rabies RNP), plant viruses (e.g. TMV, cow pea and cauliflower mosaic viruses), vesicular stomatitis virus-nucleocapsid protein (VSV-N), poxvirus subunits and Semliki forest virus subunits.

In another alternative embodiment, X may be an artificial molecular carrier. Non-limiting examples of an artificial molecular carrier include multiantigenic peptides (MAP) and microspheres. In an additional embodiment X may be yeast virus-like particles (VLPs). In another additional embodiment, X may be a malarial protein antigen.

Furthermore, X may be selected from the group comprising Diphtheria, Tetanus, and Pertussis vaccines or components thereof; poliovirus vaccines and components thereof; Rubella, Mumps, and Measles vaccines or components thereof; Hepatitis vaccines (A,B,C, and delta) and components thereof; *Haemophilus* (A and B) vaccines and components thereof; vaccinia and smallpox vaccines and components thereof; and varicella-zoster vaccines and components thereof.

In a preferred embodiment, X may be a pharmaceutically acceptable carrier for human subjects. In other words, X may be a carrier that safely elicits an antibody response in a subject. In this context, the term "safely" means that the carrier does not substantially elicit an immune response that cross-reacts with a self-protein, or a regularly ingested protein of the subject. Non-limiting examples of pharmaceutically acceptable carriers for use in human subjects include mutant diphtheria toxoid ($CRM_{197}$) and tetanus toxoid. In one preferred embodiment, X may be diphtheria toxoid $CRM_{197}$. In another preferred embodiment, X may be tetanus toxoid.

To increase the elicited immune response to a hapten compound of the invention, generally more than one hapten compound is conjugated to an individual carrier molecule, X, as expressed by n (i.e., the number of hapten compounds conjugated to X). Generally speaking, n is an integer greater than or equal to 3. In one embodiment, n may be 3, 4, or 5. In another embodiment, n may be 6, 7, 8, or 9. In yet another embodiment, n may be 10, 11, 12, or 13 or more. In an exemplary embodiment, n is greater than or equal to 5.

In an alternative embodiment, a hapten compound corresponding to formula (II) is conjugated via L to a carrier molecule, X, to form a compound having formula (VII):

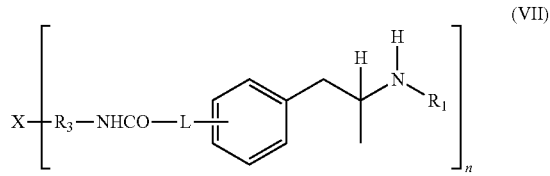

wherein:

$R_1$, L, n, and X are as described for compounds corresponding to formula (VI); and $R_3$ may be selected from the group comprising a direct bond, hydrocarbyl, and substituted hydrocarbyl.

In one alternative embodiment, $R_3$ may be a direct bond. In another alternative embodiment, $R_3$ may be a hydrocarbyl. In yet another alternative embodiment, $R_3$ may be a substituted hydrocarbyl. In an exemplary alternative of this embodiment, $R_3$ may be $(CH_2)_4$ or $(CH_2)_4NHCO(CH_2)_5$.

In another embodiment, a hapten compound corresponding to formula (III) is conjugated via L to a carrier molecule, X, to form a compound having formula (VIII):

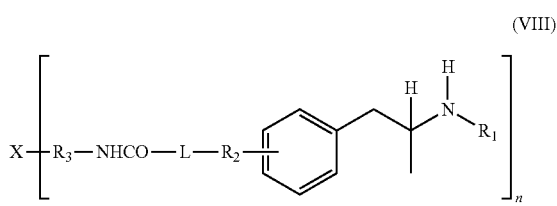

(VIII)

wherein:

$R_1$, L, n, and X are as described for compounds corresponding to formula (VI);

$R_2$ is as described for compounds corresponding to formula (III); and $R_3$ may be selected from the group comprising a direct bond, hydrocarbyl, and substituted hydrocarbyl. In an exemplary alternative of this embodiment, $R_3$ is $(CH_2)_4$ or $(CH_2)_4NHCO(CH_2)_5$.

In a further embodiment, a hapten compound corresponding to formula (IV) is conjugated via L to a carrier molecule, X, to form a compound having formula (IX):

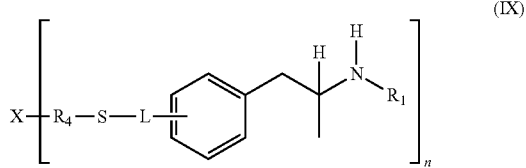

(IX)

wherein:

$R_1$, L, n, and X are as described for compounds corresponding to formula (VI); and $R_4$ may be selected from the group comprising a direct bond, hydrocarbyl, and substituted hydrocarbyl.

In one alternative of this embodiment, $R_4$ may be a direct bond. In another alternative of this embodiment, $R_4$ may be a hydrocarbyl. In yet another alternative of this embodiment, $R_4$ may be a substituted hydrocarbyl. In an exemplary alternative of this embodiment, $R_4$ may be [N-maleimidomethyl]cyclohexane-1-carboxylate.

In another embodiment, a hapten compound corresponding to formula (V) is conjugated via L to a carrier molecule, X, to form a compound having formula (X):

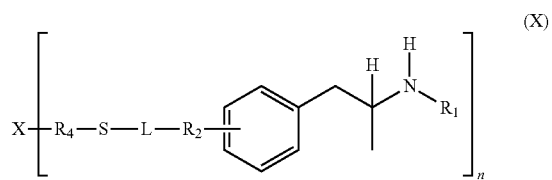

(X)

wherein:

$R_1$, $R_4$, L, n, and X are as described for compounds corresponding to formula (VIII) and (IX); and $R_2$ is as described for compounds corresponding to formula (III).

Exemplary compounds of the invention having formulas (VI), (VII), (VIII), (IX), and (X) are shown in Table B.

TABLE B

| L Group | Position on Ring | Carrier |
|---|---|---|
| —$(CH_2)_{11}$COOH | Para | KLH |
| —$(CH_2)_{11}$COOH | Para | Diptheria $CRM_{197}$ |
| —$(CH_2)_{11}$COOH | Para | Tetanus toxoid |
| —$(CH_2)_{11}$COOH | Meta | KLH |
| —$(CH_2)_{11}$COOH | Meta | Diptheria $CRM_{197}$ |
| —$(CH_2)_{11}$COOH | Meta | Tetanus toxoid |
| —$(CH_2)_{12}$COOH | Para | KLH |
| —$(CH_2)_{12}$COOH | Para | Diptheria $CRM_{197}$ |
| —$(CH_2)_{12}$COOH | Para | Tetanus toxoid |
| —$(CH_2)_{12}$COOH | Meta | KLH |
| —$(CH_2)_{12}$COOH | Meta | Diptheria $CRM_{197}$ |
| —$(CH_2)_{12}$COOH | Meta | Tetanus toxoid |
| —$(CH_2)_{13}$COOH | Para | KLH |
| —$(CH_2)_{13}$COOH | Para | Diptheria $CRM_{197}$ |
| —$(CH_2)_{13}$COOH | Para | Tetanus toxoid |
| —$(CH_2)_{13}$COOH | Meta | KLH |
| —$(CH_2)_{13}$COOH | Meta | Diptheria $CRM_{197}$ |
| —$(CH_2)_{13}$COOH | Meta | Tetanus toxoid |
| —$(CH_2)_{14}$COOH | Para | KLH |
| —$(CH_2)_{14}$COOH | Para | Diptheria $CRM_{197}$ |
| —$(CH_2)_{14}$COOH | Para | Tetanus toxoid |
| —$(CH_2)_{14}$COOH | Meta | KLH |
| —$(CH_2)_{14}$COOH | Meta | Diptheria $CRM_{197}$ |
| —$(CH_2)_{14}$COOH | Meta | Tetanus toxoid |
| —$(CH_2)_{15}$COOH | Para | KLH |
| —$(CH_2)_{15}$COOH | Para | Diptheria $CRM_{197}$ |
| —$(CH_2)_{15}$COOH | Para | Tetanus toxoid |
| —$(CH_2)_{15}$COOH | Meta | KLH |
| —$(CH_2)_{15}$COOH | Meta | Diptheria $CRM_{197}$ |
| —$(CH_2)_{15}$COOH | Meta | Tetanus toxoid |
| —$(CH_2)_{16}$COOH | Para | KLH |
| —$(CH_2)_{16}$COOH | Para | Diptheria $CRM_{197}$ |
| —$(CH_2)_{16}$COOH | Para | Tetanus toxoid |
| —$(CH_2)_{16}$COOH | Meta | KLH |
| —$(CH_2)_{16}$COOH | Meta | Diptheria $CRM_{197}$ |
| —$(CH_2)_{16}$COOH | Meta | Tetanus toxoid |
| —$(CH_2)_{17}$COOH | Para | KLH |
| —$(CH_2)_{17}$COOH | Para | Diptheria $CRM_{197}$ |
| —$(CH_2)_{17}$COOH | Para | Tetanus toxoid |
| —$(CH_2)_{17}$COOH | Meta | KLH |
| —$(CH_2)_{17}$COOH | Meta | Diptheria $CRM_{197}$ |
| —$(CH_2)_{17}$COOH | Meta | Tetanus toxoid |
| —$(CH_2)_{18}$COOH | Para | KLH |
| —$(CH_2)_{18}$COOH | Para | Diptheria $CRM_{197}$ |
| —$(CH_2)_{18}$COOH | Para | Tetanus toxoid |
| —$(CH_2)_{18}$COOH | Meta | KLH |
| —$(CH_2)_{18}$COOH | Meta | Diptheria $CRM_{197}$ |
| —$(CH_2)_{18}$COOH | Meta | Tetanus toxoid |
| —$(CH_2)_{19}$COOH | Para | KLH |
| —$(CH_2)_{19}$COOH | Para | Diptheria $CRM_{197}$ |
| —$(CH_2)_{19}$COOH | Para | Tetanus toxoid |
| —$(CH_2)_{19}$COOH | Meta | KLH |
| —$(CH_2)_{19}$COOH | Meta | Diptheria $CRM_{197}$ |
| —$(CH_2)_{19}$COOH | Meta | Tetanus toxoid |
| —$(CH_2)_{20}$COOH | Para | KLH |

TABLE B-continued

| L Group | Position on Ring | Carrier |
|---|---|---|
| —(CH$_2$)$_{20}$COOH | Para | Diptheria CRM$_{197}$ |
| —(CH$_2$)$_{20}$COOH | Para | Tetanus toxoid |
| —(CH$_2$)$_{20}$COOH | Meta | KLH |
| —(CH$_2$)$_{20}$COOH | Meta | Diptheria CRM$_{197}$ |
| —(CH$_2$)$_{20}$COOH | Meta | Tetanus toxoid |
| —(CH$_2$)$_{21}$COOH | Para | KLH |
| —(CH$_2$)$_{21}$COOH | Para | Diptheria CRM$_{197}$ |
| —(CH$_2$)$_{21}$COOH | Para | Tetanus toxoid |
| —(CH$_2$)$_{21}$COOH | Meta | KLH |
| —(CH$_2$)$_{21}$COOH | Meta | Diptheria CRM$_{197}$ |
| —(CH$_2$)$_{21}$COOH | Meta | Tetanus toxoid |
| —(CH$_2$)$_{22}$COOH | Para | KLH |
| —(CH$_2$)$_{22}$COOH | Para | Diptheria CRM$_{197}$ |
| —(CH$_2$)$_{22}$COOH | Para | Tetanus toxoid |
| —(CH$_2$)$_{22}$COOH | Meta | KLH |
| —(CH$_2$)$_{22}$COOH | Meta | Diptheria CRM$_{197}$ |
| —(CH$_2$)$_{22}$COOH | Meta | Tetanus toxoid |
| —(CH$_2$)$_{23}$COOH | Para | KLH |
| —(CH$_2$)$_{23}$COOH | Para | Diptheria CRM$_{197}$ |
| —(CH$_2$)$_{23}$COOH | Para | Tetanus toxoid |
| —(CH$_2$)$_{23}$COOH | Meta | KLH |
| —(CH$_2$)$_{23}$COOH | Meta | Diptheria CRM$_{197}$ |
| —(CH$_2$)$_{23}$COOH | Meta | Tetanus toxoid |
| —(CH$_2$)$_{24}$COOH | Para | KLH |
| —(CH$_2$)$_{24}$COOH | Para | Diptheria CRM$_{197}$ |
| —(CH$_2$)$_{24}$COOH | Para | Tetanus toxoid |
| —(CH$_2$)$_{24}$COOH | Meta | KLH |
| —(CH$_2$)$_{24}$COOH | Meta | Diptheria CRM$_{197}$ |
| —(CH$_2$)$_{24}$COOH | Meta | Tetanus toxoid |
| —(CH$_2$)$_{25}$COOH | Para | KLH |
| —(CH$_2$)$_{25}$COOH | Para | Diptheria CRM$_{197}$ |
| —(CH$_2$)$_{25}$COOH | Para | Tetanus toxoid |
| —(CH$_2$)$_{25}$COOH | Meta | KLH |
| —(CH$_2$)$_{25}$COOH | Meta | Diptheria CRM$_{197}$ |
| —(CH$_2$)$_{25}$COOH | Meta | Tetanus toxoid |
| —(CH$_2$)$_{26}$COOH | Para | KLH |
| —(CH$_2$)$_{26}$COOH | Para | Diptheria CRM$_{197}$ |
| —(CH$_2$)$_{26}$COOH | Para | Tetanus toxoid |
| —(CH$_2$)$_{26}$COOH | Meta | KLH |
| —(CH$_2$)$_{26}$COOH | Meta | Diptheria CRM$_{197}$ |
| —(CH$_2$)$_{26}$COOH | Meta | Tetanus toxoid |
| —(CH$_2$)$_{27}$COOH | Para | KLH |
| —(CH$_2$)$_{27}$COOH | Para | Diptheria CRM$_{197}$ |
| —(CH$_2$)$_{27}$COOH | Para | Tetanus toxoid |
| —(CH$_2$)$_{27}$COOH | Meta | KLH |
| —(CH$_2$)$_{27}$COOH | Meta | Diptheria CRM$_{197}$ |
| —(CH$_2$)$_{27}$COOH | Meta | Tetanus toxoid |
| —(CH$_2$)$_{28}$COOH | Para | KLH |
| —(CH$_2$)$_{28}$COOH | Para | Diptheria CRM$_{197}$ |
| —(CH$_2$)$_{28}$COOH | Para | Tetanus toxoid |
| —(CH$_2$)$_{28}$COOH | Meta | KLH |
| —(CH$_2$)$_{28}$COOH | Meta | Diptheria CRM$_{197}$ |
| —(CH$_2$)$_{28}$COOH | Meta | Tetanus toxoid |
| —(CH$_2$)$_{29}$COOH | Para | KLH |
| —(CH$_2$)$_{29}$COOH | Para | Diptheria CRM$_{197}$ |
| —(CH$_2$)$_{29}$COOH | Para | Tetanus toxoid |
| —(CH$_2$)$_{29}$COOH | Meta | KLH |
| —(CH$_2$)$_{29}$COOH | Meta | Diptheria CRM$_{197}$ |
| —(CH$_2$)$_{29}$COOH | Meta | Tetanus toxoid |
| —(CH$_2$)$_{30}$COOH | Para | KLH |
| —(CH$_2$)$_{30}$COOH | Para | Diptheria CRM$_{197}$ |
| —(CH$_2$)$_{30}$COOH | Para | Tetanus toxoid |
| —(CH$_2$)$_{30}$COOH | Meta | KLH |
| —(CH$_2$)$_{30}$COOH | Meta | Diptheria CRM$_{197}$ |
| —(CH$_2$)$_{30}$COOH | Meta | Tetanus toxoid |
| —(CH$_2$)$_7$SH | Para | KLH |
| —(CH$_2$)$_7$SH | Para | Diptheria CRM$_{197}$ |
| —(CH$_2$)$_7$SH | Para | Tetanus toxoid |
| —(CH$_2$)$_7$SH | Meta | KLH |
| —(CH$_2$)$_7$SH | Meta | Diptheria CRM$_{197}$ |
| —(CH$_2$)$_7$SH | Meta | Tetanus toxoid |
| —(CH$_2$)$_8$SH | Para | KLH |
| —(CH$_2$)$_8$SH | Para | Diptheria CRM$_{197}$ |
| —(CH$_2$)$_8$SH | Para | Tetanus toxoid |
| —(CH$_2$)$_8$SH | Meta | KLH |
| —(CH$_2$)$_8$SH | Meta | Diptheria CRM$_{197}$ |
| —(CH$_2$)$_8$SH | Meta | Tetanus toxoid |
| —(CH$_2$)$_9$SH | Para | KLH |
| —(CH$_2$)$_9$SH | Para | Diptheria CRM$_{197}$ |
| —(CH$_2$)$_9$SH | Para | Tetanus toxoid |
| —(CH$_2$)$_9$SH | Meta | KLH |
| —(CH$_2$)$_9$SH | Meta | Diptheria CRM$_{197}$ |
| —(CH$_2$)$_9$SH | Meta | Tetanus toxoid |
| —(CH$_2$)$_{10}$SH | Para | KLH |
| —(CH$_2$)$_{10}$SH | Para | Diptheria CRM$_{197}$ |
| —(CH$_2$)$_{10}$SH | Para | Tetanus toxoid |
| —(CH$_2$)$_{10}$SH | Meta | KLH |
| —(CH$_2$)$_{10}$SH | Meta | Diptheria CRM$_{197}$ |
| —(CH$_2$)$_{10}$SH | Meta | Tetanus toxoid |
| —(CH$_2$)$_{11}$SH | Para | KLH |
| —(CH$_2$)$_{11}$SH | Para | Diptheria CRM$_{197}$ |
| —(CH$_2$)$_{11}$SH | Para | Tetanus toxoid |
| —(CH$_2$)$_{11}$SH | Meta | KLH |
| —(CH$_2$)$_{11}$SH | Meta | Diptheria CRM$_{197}$ |
| —(CH$_2$)$_{11}$SH | Meta | Tetanus toxoid |
| —(CH$_2$)$_{12}$SH | Para | KLH |
| —(CH$_2$)$_{12}$SH | Para | Diptheria CRM$_{197}$ |
| —(CH$_2$)$_{12}$SH | Para | Tetanus toxoid |
| —(CH$_2$)$_{12}$SH | Meta | KLH |
| —(CH$_2$)$_{12}$SH | Meta | Diptheria CRM$_{197}$ |
| —(CH$_2$)$_{12}$SH | Meta | Tetanus toxoid |
| —(CH$_2$)$_{13}$SH | Para | KLH |
| —(CH$_2$)$_{13}$SH | Para | Diptheria CRM$_{197}$ |
| —(CH$_2$)$_{13}$SH | Para | Tetanus toxoid |
| —(CH$_2$)$_{13}$SH | Meta | KLH |
| —(CH$_2$)$_{13}$SH | Meta | Diptheria CRM$_{197}$ |
| —(CH$_2$)$_{13}$SH | Meta | Tetanus toxoid |
| —(CH$_2$)$_{14}$SH | Para | KLH |
| —(CH$_2$)$_{14}$SH | Para | Diptheria CRM$_{197}$ |
| —(CH$_2$)$_{14}$SH | Para | Tetanus toxoid |
| —(CH$_2$)$_{14}$SH | Meta | KLH |
| —(CH$_2$)$_{14}$SH | Meta | Diptheria CRM$_{197}$ |
| —(CH$_2$)$_{14}$SH | Meta | Tetanus toxoid |
| —(CH$_2$)$_{15}$SH | Para | KLH |
| —(CH$_2$)$_{15}$SH | Para | Diptheria CRM$_{197}$ |
| —(CH$_2$)$_{15}$SH | Para | Tetanus toxoid |
| —(CH$_2$)$_{15}$SH | Meta | KLH |
| —(CH$_2$)$_{15}$SH | Meta | Diptheria CRM$_{197}$ |
| —(CH$_2$)$_{15}$SH | Meta | Tetanus toxoid |
| —(CH$_2$)$_{16}$SH | Para | KLH |
| —(CH$_2$)$_{16}$SH | Para | Diptheria CRM$_{197}$ |
| —(CH$_2$)$_{16}$SH | Para | Tetanus toxoid |
| —(CH$_2$)$_{16}$SH | Meta | KLH |
| —(CH$_2$)$_{16}$SH | Meta | Diptheria CRM$_{197}$ |
| —(CH$_2$)$_{16}$SH | Meta | Tetanus toxoid |
| —(CH$_2$)$_{17}$SH | Para | KLH |
| —(CH$_2$)$_{17}$SH | Para | Diptheria CRM$_{197}$ |
| —(CH$_2$)$_{17}$SH | Para | Tetanus toxoid |
| —(CH$_2$)$_{17}$SH | Meta | KLH |
| —(CH$_2$)$_{17}$SH | Meta | Diptheria CRM$_{197}$ |
| —(CH$_2$)$_{17}$SH | Meta | Tetanus toxoid |
| —(CH$_2$)$_{18}$SH | Para | KLH |
| —(CH$_2$)$_{18}$SH | Para | Diptheria CRM$_{197}$ |
| —(CH$_2$)$_{18}$SH | Para | Tetanus toxoid |
| —(CH$_2$)$_{18}$SH | Meta | KLH |
| —(CH$_2$)$_{18}$SH | Meta | Diptheria CRM$_{197}$ |
| —(CH$_2$)$_{18}$SH | Meta | Tetanus toxoid |
| —(CH$_2$)$_{19}$SH | Para | KLH |
| —(CH$_2$)$_{19}$SH | Para | Diptheria CRM$_{197}$ |
| —(CH$_2$)$_{19}$SH | Para | Tetanus toxoid |
| —(CH$_2$)$_{19}$SH | Meta | KLH |
| —(CH$_2$)$_{19}$SH | Meta | Diptheria CRM$_{197}$ |
| —(CH$_2$)$_{19}$SH | Meta | Tetanus toxoid |
| —(CH$_2$)$_{20}$SH | Para | KLH |
| —(CH$_2$)$_{20}$SH | Para | Diptheria CRM$_{197}$ |
| —(CH$_2$)$_{20}$SH | Para | Tetanus toxoid |
| —(CH$_2$)$_{20}$SH | Meta | KLH |
| —(CH$_2$)$_{20}$SH | Meta | Diptheria CRM$_{197}$ |
| —(CH$_2$)$_{20}$SH | Meta | Tetanus toxoid |
| —(CH$_2$)$_{21}$SH | Para | KLH |
| —(CH$_2$)$_{21}$SH | Para | Diptheria CRM$_{197}$ |
| —(CH$_2$)$_{21}$SH | Para | Tetanus toxoid |
| —(CH$_2$)$_{21}$SH | Meta | KLH |
| —(CH$_2$)$_{21}$SH | Meta | Diptheria CRM$_{197}$ |

TABLE B-continued

| L Group | Position on Ring | Carrier |
|---|---|---|
| —(CH$_2$)$_{21}$SH | Meta | Tetanus toxoid |
| —(CH$_2$)$_{22}$SH | Para | KLH |
| —(CH$_2$)$_{22}$SH | Para | Diptheria CRM$_{197}$ |
| —(CH$_2$)$_{22}$SH | Para | Tetanus toxoid |
| —(CH$_2$)$_{22}$SH | Meta | KLH |
| —(CH$_2$)$_{22}$SH | Meta | Diptheria CRM$_{197}$ |
| —(CH$_2$)$_{22}$SH | Meta | Tetanus toxoid |
| —(CH$_2$)$_{23}$SH | Para | KLH |
| —(CH$_2$)$_{23}$SH | Para | Diptheria CRM$_{197}$ |
| —(CH$_2$)$_{23}$SH | Para | Tetanus toxoid |
| —(CH$_2$)$_{23}$SH | Meta | KLH |
| —(CH$_2$)$_{23}$SH | Meta | Diptheria CRM$_{197}$ |
| —(CH$_2$)$_{23}$SH | Meta | Tetanus toxoid |
| —(CH$_2$)$_{24}$SH | Para | KLH |
| —(CH$_2$)$_{24}$SH | Para | Diptheria CRM$_{197}$ |
| —(CH$_2$)$_{24}$SH | Para | Tetanus toxoid |
| —(CH$_2$)$_{24}$SH | Meta | KLH |
| —(CH$_2$)$_{24}$SH | Meta | Diptheria CRM$_{197}$ |
| —(CH$_2$)$_{24}$SH | Meta | Tetanus toxoid |
| —(CH$_2$)$_{25}$SH | Para | KLH |
| —(CH$_2$)$_{25}$SH | Para | Diptheria CRM$_{197}$ |
| —(CH$_2$)$_{25}$SH | Para | Tetanus toxoid |
| —(CH$_2$)$_{25}$SH | Meta | KLH |
| —(CH$_2$)$_{25}$SH | Meta | Diptheria CRM$_{197}$ |
| —(CH$_2$)$_{25}$SH | Meta | Tetanus toxoid |
| —(CH$_2$)$_{26}$SH | Para | KLH |
| —(CH$_2$)$_{26}$SH | Para | Diptheria CRM$_{197}$ |
| —(CH$_2$)$_{26}$SH | Para | Tetanus toxoid |
| —(CH$_2$)$_{26}$SH | Meta | KLH |
| —(CH$_2$)$_{26}$SH | Meta | Diptheria CRM$_{197}$ |
| —(CH$_2$)$_{26}$SH | Meta | Tetanus toxoid |
| —(CH$_2$)$_{27}$SH | Para | KLH |
| —(CH$_2$)$_{27}$SH | Para | Diptheria CRM$_{197}$ |
| —(CH$_2$)$_{27}$SH | Para | Tetanus toxoid |
| —(CH$_2$)$_{27}$SH | Meta | KLH |
| —(CH$_2$)$_{27}$SH | Meta | Diptheria CRM$_{197}$ |
| —(CH$_2$)$_{27}$SH | Meta | Tetanus toxoid |
| —(CH$_2$)$_{28}$SH | Para | KLH |
| —(CH$_2$)$_{28}$SH | Para | Diptheria CRM$_{197}$ |
| —(CH$_2$)$_{28}$SH | Para | Tetanus toxoid |
| —(CH$_2$)$_{28}$SH | Meta | KLH |
| —(CH$_2$)$_{28}$SH | Meta | Diptheria CRM$_{197}$ |
| —(CH$_2$)$_{28}$SH | Meta | Tetanus toxoid |
| —(CH$_2$)$_{29}$SH | Para | KLH |
| —(CH$_2$)$_{29}$SH | Para | Diptheria CRM$_{197}$ |
| —(CH$_2$)$_{29}$SH | Para | Tetanus toxoid |
| —(CH$_2$)$_{29}$SH | Meta | KLH |
| —(CH$_2$)$_{29}$SH | Meta | Diptheria CRM$_{197}$ |
| —(CH$_2$)$_{29}$SH | Meta | Tetanus toxoid |
| —(CH$_2$)$_{30}$SH | Para | KLH |
| —(CH$_2$)$_{30}$SH | Para | Diptheria CRM$_{197}$ |
| —(CH$_2$)$_{30}$SH | Para | Tetanus toxoid |
| —(CH$_2$)$_{30}$SH | Meta | KLH |
| —(CH$_2$)$_{30}$SH | Meta | Diptheria CRM$_{197}$ |
| —(CH$_2$)$_{30}$SH | Meta | Tetanus toxoid |
| —O(CH$_2$)$_{10}$COOH | Para | KLH |
| —O(CH$_2$)$_{10}$COOH | Para | Diptheria CRM$_{197}$ |
| —O(CH$_2$)$_{10}$COOH | Para | Tetanus toxoid |
| —O(CH$_2$)$_{10}$COOH | Meta | KLH |
| —O(CH$_2$)$_{10}$COOH | Meta | Diptheria CRM$_{197}$ |
| —O(CH$_2$)$_{10}$COOH | Meta | Tetanus toxoid |
| —O(CH$_2$)$_{11}$COOH | Para | KLH |
| —O(CH$_2$)$_{11}$COOH | Para | Diptheria CRM$_{197}$ |
| —O(CH$_2$)$_{11}$COOH | Para | Tetanus toxoid |
| —O(CH$_2$)$_{11}$COOH | Meta | KLH |
| —O(CH$_2$)$_{11}$COOH | Meta | Diptheria CRM$_{197}$ |
| —O(CH$_2$)$_{11}$COOH | Meta | Tetanus toxoid |
| —O(CH$_2$)$_{12}$COOH | Para | KLH |
| —O(CH$_2$)$_{12}$COOH | Para | Diptheria CRM$_{197}$ |
| —O(CH$_2$)$_{12}$COOH | Para | Tetanus toxoid |
| —O(CH$_2$)$_{12}$COOH | Meta | KLH |
| —O(CH$_2$)$_{12}$COOH | Meta | Diptheria CRM$_{197}$ |
| —O(CH$_2$)$_{12}$COOH | Meta | Tetanus toxoid |
| —O(CH$_2$)$_{13}$COOH | Para | KLH |
| —O(CH$_2$)$_{13}$COOH | Para | Diptheria CRM$_{197}$ |
| —O(CH$_2$)$_{13}$COOH | Para | Tetanus toxoid |
| —O(CH$_2$)$_{13}$COOH | Meta | KLH |
| —O(CH$_2$)$_{13}$COOH | Meta | Diptheria CRM$_{197}$ |
| —O(CH$_2$)$_{13}$COOH | Meta | Tetanus toxoid |
| —O(CH$_2$)$_{14}$COOH | Para | KLH |
| —O(CH$_2$)$_{14}$COOH | Para | Diptheria CRM$_{197}$ |
| —O(CH$_2$)$_{14}$COOH | Para | Tetanus toxoid |
| —O(CH$_2$)$_{14}$COOH | Meta | KLH |
| —O(CH$_2$)$_{14}$COOH | Meta | Diptheria CRM$_{197}$ |
| —O(CH$_2$)$_{14}$COOH | Meta | Tetanus toxoid |
| —O(CH$_2$)$_{15}$COOH | Para | KLH |
| —O(CH$_2$)$_{15}$COOH | Para | Diptheria CRM$_{197}$ |
| —O(CH$_2$)$_{15}$COOH | Para | Tetanus toxoid |
| —O(CH$_2$)$_{15}$COOH | Meta | KLH |
| —O(CH$_2$)$_{15}$COOH | Meta | Diptheria CRM$_{197}$ |
| —O(CH$_2$)$_{15}$COOH | Meta | Tetanus toxoid |
| —O(CH$_2$)$_{16}$COOH | Para | KLH |
| —O(CH$_2$)$_{16}$COOH | Para | Diptheria CRM$_{197}$ |
| —O(CH$_2$)$_{16}$COOH | Para | Tetanus toxoid |
| —O(CH$_2$)$_{16}$COOH | Meta | KLH |
| —O(CH$_2$)$_{16}$COOH | Meta | Diptheria CRM$_{197}$ |
| —O(CH$_2$)$_{16}$COOH | Meta | Tetanus toxoid |
| —O(CH$_2$)$_{17}$COOH | Para | KLH |
| —O(CH$_2$)$_{17}$COOH | Para | Diptheria CRM$_{197}$ |
| —O(CH$_2$)$_{17}$COOH | Para | Tetanus toxoid |
| —O(CH$_2$)$_{17}$COOH | Meta | KLH |
| —O(CH$_2$)$_{17}$COOH | Meta | Diptheria CRM$_{197}$ |
| —O(CH$_2$)$_{17}$COOH | Meta | Tetanus toxoid |
| —O(CH$_2$)$_{18}$COOH | Para | KLH |
| —O(CH$_2$)$_{18}$COOH | Para | Diptheria CRM$_{197}$ |
| —O(CH$_2$)$_{18}$COOH | Para | Tetanus toxoid |
| —O(CH$_2$)$_{18}$COOH | Meta | KLH |
| —O(CH$_2$)$_{18}$COOH | Meta | Diptheria CRM$_{197}$ |
| —O(CH$_2$)$_{18}$COOH | Meta | Tetanus toxoid |
| —O(CH$_2$)$_{19}$COOH | Para | KLH |
| —O(CH$_2$)$_{19}$COOH | Para | Diptheria CRM$_{197}$ |
| —O(CH$_2$)$_{19}$COOH | Para | Tetanus toxoid |
| —O(CH$_2$)$_{19}$COOH | Meta | KLH |
| —O(CH$_2$)$_{19}$COOH | Meta | Diptheria CRM$_{197}$ |
| —O(CH$_2$)$_{19}$COOH | Meta | Tetanus toxoid |
| —O(CH$_2$)$_{20}$COOH | Para | KLH |
| —O(CH$_2$)$_{20}$COOH | Para | Diptheria CRM$_{197}$ |
| —O(CH$_2$)$_{20}$COOH | Para | Tetanus toxoid |
| —O(CH$_2$)$_{20}$COOH | Meta | KLH |
| —O(CH$_2$)$_{20}$COOH | Meta | Diptheria CRM$_{197}$ |
| —O(CH$_2$)$_{20}$COOH | Meta | Tetanus toxoid |
| —O(CH$_2$)$_{21}$COOH | Para | KLH |
| —O(CH$_2$)$_{21}$COOH | Para | Diptheria CRM$_{197}$ |
| —O(CH$_2$)$_{21}$COOH | Para | Tetanus toxoid |
| —O(CH$_2$)$_{21}$COOH | Meta | KLH |
| —O(CH$_2$)$_{21}$COOH | Meta | Diptheria CRM$_{197}$ |
| —O(CH$_2$)$_{21}$COOH | Meta | Tetanus toxoid |
| —O(CH$_2$)$_{22}$COOH | Para | KLH |
| —O(CH$_2$)$_{22}$COOH | Para | Diptheria CRM$_{197}$ |
| —O(CH$_2$)$_{22}$COOH | Para | Tetanus toxoid |
| —O(CH$_2$)$_{22}$COOH | Meta | KLH |
| —O(CH$_2$)$_{22}$COOH | Meta | Diptheria CRM$_{197}$ |
| —O(CH$_2$)$_{22}$COOH | Meta | Tetanus toxoid |
| —O(CH$_2$)$_{23}$COOH | Para | KLH |
| —O(CH$_2$)$_{23}$COOH | Para | Diptheria CRM$_{197}$ |
| —O(CH$_2$)$_{23}$COOH | Para | Tetanus toxoid |
| —O(CH$_2$)$_{23}$COOH | Meta | KLH |
| —O(CH$_2$)$_{23}$COOH | Meta | Diptheria CRM$_{197}$ |
| —O(CH$_2$)$_{23}$COOH | Meta | Tetanus toxoid |
| —O(CH$_2$)$_{24}$COOH | Para | KLH |
| —O(CH$_2$)$_{24}$COOH | Para | Diptheria CRM$_{197}$ |
| —O(CH$_2$)$_{24}$COOH | Para | Tetanus toxoid |
| —O(CH$_2$)$_{24}$COOH | Meta | KLH |
| —O(CH$_2$)$_{24}$COOH | Meta | Diptheria CRM$_{197}$ |
| —O(CH$_2$)$_{24}$COOH | Meta | Tetanus toxoid |
| —O(CH$_2$)$_{25}$COOH | Para | KLH |
| —O(CH$_2$)$_{25}$COOH | Para | Diptheria CRM$_{197}$ |
| —O(CH$_2$)$_{25}$COOH | Para | Tetanus toxoid |
| —O(CH$_2$)$_{25}$COOH | Meta | KLH |
| —O(CH$_2$)$_{25}$COOH | Meta | Diptheria CRM$_{197}$ |
| —O(CH$_2$)$_{25}$COOH | Meta | Tetanus toxoid |
| —O(CH$_2$)$_{26}$COOH | Para | KLH |
| —O(CH$_2$)$_{26}$COOH | Para | Diptheria CRM$_{197}$ |
| —O(CH$_2$)$_{26}$COOH | Para | Tetanus toxoid |

TABLE B-continued

| L Group | Position on Ring | Carrier |
|---|---|---|
| —O(CH$_2$)$_{26}$COOH | Meta | KLH |
| —O(CH$_2$)$_{26}$COOH | Meta | Diptheria CRM$_{197}$ |
| —O(CH$_2$)$_{26}$COOH | Meta | Tetanus toxoid |
| —O(CH$_2$)$_{27}$COOH | Para | KLH |
| —O(CH$_2$)$_{27}$COOH | Para | Diptheria CRM$_{197}$ |
| —O(CH$_2$)$_{27}$COOH | Para | Tetanus toxoid |
| —O(CH$_2$)$_{27}$COOH | Meta | KLH |
| —O(CH$_2$)$_{27}$COOH | Meta | Diptheria CRM$_{197}$ |
| —O(CH$_2$)$_{27}$COOH | Meta | Tetanus toxoid |
| —O(CH$_2$)$_{28}$COOH | Para | KLH |
| —O(CH$_2$)$_{28}$COOH | Para | Diptheria CRM$_{197}$ |
| —O(CH$_2$)$_{28}$COOH | Para | Tetanus toxoid |
| —O(CH$_2$)$_{28}$COOH | Meta | KLH |
| —O(CH$_2$)$_{28}$COOH | Meta | Diptheria CRM$_{197}$ |
| —O(CH$_2$)$_{28}$COOH | Meta | Tetanus toxoid |
| —O(CH$_2$)$_{29}$COOH | Para | KLH |
| —O(CH$_2$)$_{29}$COOH | Para | Diptheria CRM$_{197}$ |
| —O(CH$_2$)$_{29}$COOH | Para | Tetanus toxoid |
| —O(CH$_2$)$_{29}$COOH | Meta | KLH |
| —O(CH$_2$)$_{29}$COOH | Meta | Diptheria CRM$_{197}$ |
| —O(CH$_2$)$_{29}$COOH | Meta | Tetanus toxoid |
| —O(CH$_2$)$_{30}$COOH | Para | KLH |
| —O(CH$_2$)$_{30}$COOH | Para | Diptheria CRM$_{197}$ |
| —O(CH$_2$)$_{30}$COOH | Para | Tetanus toxoid |
| —O(CH$_2$)$_{30}$COOH | Meta | KLH |
| —O(CH$_2$)$_{30}$COOH | Meta | Diptheria CRM$_{197}$ |
| —O(CH$_2$)$_{30}$COOH | Meta | Tetanus toxoid |
| —O(CH$_2$)$_6$SH | Para | KLH |
| —O(CH$_2$)$_6$SH | Para | Diptheria CRM$_{197}$ |
| —O(CH$_2$)$_6$SH | Para | Tetanus toxoid |
| —O(CH$_2$)$_6$SH | Meta | KLH |
| —O(CH$_2$)$_6$SH | Meta | Diptheria CRM$_{197}$ |
| —O(CH$_2$)$_6$SH | Meta | Tetanus toxoid |
| —O(CH$_2$)$_7$SH | Para | KLH |
| —O(CH$_2$)$_7$SH | Para | Diptheria CRM$_{197}$ |
| —O(CH$_2$)$_7$SH | Para | Tetanus toxoid |
| —O(CH$_2$)$_7$SH | Meta | KLH |
| —O(CH$_2$)$_7$SH | Meta | Diptheria CRM$_{197}$ |
| —O(CH$_2$)$_7$SH | Meta | Tetanus toxoid |
| —O(CH$_2$)$_8$SH | Para | KLH |
| —O(CH$_2$)$_8$SH | Para | Diptheria CRM$_{197}$ |
| —O(CH$_2$)$_8$SH | Para | Tetanus toxoid |
| —O(CH$_2$)$_8$SH | Meta | KLH |
| —O(CH$_2$)$_8$SH | Meta | Diptheria CRM$_{197}$ |
| —O(CH$_2$)$_8$SH | Meta | Tetanus toxoid |
| —O(CH$_2$)$_9$SH | Para | KLH |
| —O(CH$_2$)$_9$SH | Para | Diptheria CRM$_{197}$ |
| —O(CH$_2$)$_9$SH | Para | Tetanus toxoid |
| —O(CH$_2$)$_9$SH | Meta | KLH |
| —O(CH$_2$)$_9$SH | Meta | Diptheria CRM$_{197}$ |
| —O(CH$_2$)$_9$SH | Meta | Tetanus toxoid |
| —O(CH$_2$)$_{10}$SH | Para | KLH |
| —O(CH$_2$)$_{10}$SH | Para | Diptheria CRM$_{197}$ |
| —O(CH$_2$)$_{10}$SH | Para | Tetanus toxoid |
| —O(CH$_2$)$_{10}$SH | Meta | KLH |
| —O(CH$_2$)$_{10}$SH | Meta | Diptheria CRM$_{197}$ |
| —O(CH$_2$)$_{10}$SH | Meta | Tetanus toxoid |
| —O(CH$_2$)$_{11}$SH | Para | KLH |
| —O(CH$_2$)$_{11}$SH | Para | Diptheria CRM$_{197}$ |
| —O(CH$_2$)$_{11}$SH | Para | Tetanus toxoid |
| —O(CH$_2$)$_{11}$SH | Meta | KLH |
| —O(CH$_2$)$_{11}$SH | Meta | Diptheria CRM$_{197}$ |
| —O(CH$_2$)$_{11}$SH | Meta | Tetanus toxoid |
| —O(CH$_2$)$_{12}$SH | Para | KLH |
| —O(CH$_2$)$_{12}$SH | Para | Diptheria CRM$_{197}$ |
| —O(CH$_2$)$_{12}$SH | Para | Tetanus toxoid |
| —O(CH$_2$)$_{12}$SH | Meta | KLH |
| —O(CH$_2$)$_{12}$SH | Meta | Diptheria CRM$_{197}$ |
| —O(CH$_2$)$_{12}$SH | Meta | Tetanus toxoid |
| —O(CH$_2$)$_{13}$SH | Para | KLH |
| —O(CH$_2$)$_{13}$SH | Para | Diptheria CRM$_{197}$ |
| —O(CH$_2$)$_{13}$SH | Para | Tetanus toxoid |
| —O(CH$_2$)$_{13}$SH | Meta | KLH |
| —O(CH$_2$)$_{13}$SH | Meta | Diptheria CRM$_{197}$ |
| —O(CH$_2$)$_{13}$SH | Meta | Tetanus toxoid |
| —O(CH$_2$)$_{14}$SH | Para | KLH |
| —O(CH$_2$)$_{14}$SH | Para | Diptheria CRM$_{197}$ |
| —O(CH$_2$)$_{14}$SH | Para | Tetanus toxoid |
| —O(CH$_2$)$_{14}$SH | Meta | KLH |
| —O(CH$_2$)$_{14}$SH | Meta | Diptheria CRM$_{197}$ |
| —O(CH$_2$)$_{14}$SH | Meta | Tetanus toxoid |
| —O(CH$_2$)$_{15}$SH | Para | KLH |
| —O(CH$_2$)$_{15}$SH | Para | Diptheria CRM$_{197}$ |
| —O(CH$_2$)$_{15}$SH | Para | Tetanus toxoid |
| —O(CH$_2$)$_{15}$SH | Meta | KLH |
| —O(CH$_2$)$_{15}$SH | Meta | Diptheria CRM$_{197}$ |
| —O(CH$_2$)$_{15}$SH | Meta | Tetanus toxoid |
| —O(CH$_2$)$_{16}$SH | Para | KLH |
| —O(CH$_2$)$_{16}$SH | Para | Diptheria CRM$_{197}$ |
| —O(CH$_2$)$_{16}$SH | Para | Tetanus toxoid |
| —O(CH$_2$)$_{16}$SH | Meta | KLH |
| —O(CH$_2$)$_{16}$SH | Meta | Diptheria CRM$_{197}$ |
| —O(CH$_2$)$_{16}$SH | Meta | Tetanus toxoid |
| —O(CH$_2$)$_{17}$SH | Para | KLH |
| —O(CH$_2$)$_{17}$SH | Para | Diptheria CRM$_{197}$ |
| —O(CH$_2$)$_{17}$SH | Para | Tetanus toxoid |
| —O(CH$_2$)$_{17}$SH | Meta | KLH |
| —O(CH$_2$)$_{17}$SH | Meta | Diptheria CRM$_{197}$ |
| —O(CH$_2$)$_{17}$SH | Meta | Tetanus toxoid |
| —O(CH$_2$)$_{18}$SH | Para | KLH |
| —O(CH$_2$)$_{18}$SH | Para | Diptheria CRM$_{197}$ |
| —O(CH$_2$)$_{18}$SH | Para | Tetanus toxoid |
| —O(CH$_2$)$_{18}$SH | Meta | KLH |
| —O(CH$_2$)$_{18}$SH | Meta | Diptheria CRM$_{197}$ |
| —O(CH$_2$)$_{18}$SH | Meta | Tetanus toxoid |
| —O(CH$_2$)$_{19}$SH | Para | KLH |
| —O(CH$_2$)$_{19}$SH | Para | Diptheria CRM$_{197}$ |
| —O(CH$_2$)$_{19}$SH | Para | Tetanus toxoid |
| —O(CH$_2$)$_{19}$SH | Meta | KLH |
| —O(CH$_2$)$_{19}$SH | Meta | Diptheria CRM$_{197}$ |
| —O(CH$_2$)$_{19}$SH | Meta | Tetanus toxoid |
| —O(CH$_2$)$_{20}$SH | Para | KLH |
| —O(CH$_2$)$_{20}$SH | Para | Diptheria CRM$_{197}$ |
| —O(CH$_2$)$_{20}$SH | Para | Tetanus toxoid |
| —O(CH$_2$)$_{20}$SH | Meta | KLH |
| —O(CH$_2$)$_{20}$SH | Meta | Diptheria CRM$_{197}$ |
| —O(CH$_2$)$_{20}$SH | Meta | Tetanus toxoid |
| —O(CH$_2$)$_{21}$SH | Para | KLH |
| —O(CH$_2$)$_{21}$SH | Para | Diptheria CRM$_{197}$ |
| —O(CH$_2$)$_{21}$SH | Para | Tetanus toxoid |
| —O(CH$_2$)$_{21}$SH | Meta | KLH |
| —O(CH$_2$)$_{21}$SH | Meta | Diptheria CRM$_{197}$ |
| —O(CH$_2$)$_{21}$SH | Meta | Tetanus toxoid |
| —O(CH$_2$)$_{22}$SH | Para | KLH |
| —O(CH$_2$)$_{22}$SH | Para | Diptheria CRM$_{197}$ |
| —O(CH$_2$)$_{22}$SH | Para | Tetanus toxoid |
| —O(CH$_2$)$_{22}$SH | Meta | KLH |
| —O(CH$_2$)$_{22}$SH | Meta | Diptheria CRM$_{197}$ |
| —O(CH$_2$)$_{22}$SH | Meta | Tetanus toxoid |
| —O(CH$_2$)$_{23}$SH | Para | KLH |
| —O(CH$_2$)$_{23}$SH | Para | Diptheria CRM$_{197}$ |
| —O(CH$_2$)$_{23}$SH | Para | Tetanus toxoid |
| —O(CH$_2$)$_{23}$SH | Meta | KLH |
| —O(CH$_2$)$_{23}$SH | Meta | Diptheria CRM$_{197}$ |
| —O(CH$_2$)$_{23}$SH | Meta | Tetanus toxoid |
| —O(CH$_2$)$_{24}$SH | Para | KLH |
| —O(CH$_2$)$_{24}$SH | Para | Diptheria CRM$_{197}$ |
| —O(CH$_2$)$_{24}$SH | Para | Tetanus toxoid |
| —O(CH$_2$)$_{24}$SH | Meta | KLH |
| —O(CH$_2$)$_{24}$SH | Meta | Diptheria CRM$_{197}$ |
| —O(CH$_2$)$_{24}$SH | Meta | Tetanus toxoid |
| —O(CH$_2$)$_{25}$SH | Para | KLH |
| —O(CH$_2$)$_{25}$SH | Para | Diptheria CRM$_{197}$ |
| —O(CH$_2$)$_{25}$SH | Para | Tetanus toxoid |
| —O(CH$_2$)$_{25}$SH | Meta | KLH |
| —O(CH$_2$)$_{25}$SH | Meta | Diptheria CRM$_{197}$ |
| —O(CH$_2$)$_{25}$SH | Meta | Tetanus toxoid |
| —O(CH$_2$)$_{26}$SH | Para | KLH |
| —O(CH$_2$)$_{26}$SH | Para | Diptheria CRM$_{197}$ |
| —O(CH$_2$)$_{26}$SH | Para | Tetanus toxoid |
| —O(CH$_2$)$_{26}$SH | Meta | KLH |
| —O(CH$_2$)$_{26}$SH | Meta | Diptheria CRM$_{197}$ |
| —O(CH$_2$)$_{26}$SH | Meta | Tetanus toxoid |
| —O(CH$_2$)$_{27}$SH | Para | KLH |

TABLE B-continued

| L Group | Position on Ring | Carrier |
|---|---|---|
| —O(CH$_2$)$_{27}$SH | Para | KLH |
| —O(CH$_2$)$_{27}$SH | Para | Diptheria CRM$_{197}$ |
| —O(CH$_2$)$_{27}$SH | Para | Tetanus toxoid |
| —O(CH$_2$)$_{27}$SH | Meta | KLH |
| —O(CH$_2$)$_{27}$SH | Meta | Diptheria CRM$_{197}$ |
| —O(CH$_2$)$_{27}$SH | Meta | Tetanus toxoid |
| —O(CH$_2$)$_{28}$SH | Para | KLH |
| —O(CH$_2$)$_{28}$SH | Para | Diptheria CRM$_{197}$ |
| —O(CH$_2$)$_{28}$SH | Para | Tetanus toxoid |
| —O(CH$_2$)$_{28}$SH | Meta | KLH |
| —O(CH$_2$)$_{28}$SH | Meta | Diptheria CRM$_{197}$ |
| —O(CH$_2$)$_{28}$SH | Meta | Tetanus toxoid |
| —O(CH$_2$)$_{29}$SH | Para | KLH |
| —O(CH$_2$)$_{29}$SH | Para | Diptheria CRM$_{197}$ |
| —O(CH$_2$)$_{29}$SH | Para | Tetanus toxoid |
| —O(CH$_2$)$_{29}$SH | Meta | KLH |
| —O(CH$_2$)$_{29}$SH | Meta | Diptheria CRM$_{197}$ |
| —O(CH$_2$)$_{29}$SH | Meta | Tetanus toxoid |
| —O(CH$_2$)$_{30}$SH | Para | KLH |
| —O(CH$_2$)$_{30}$SH | Para | Diptheria CRM$_{197}$ |
| —O(CH$_2$)$_{30}$SH | Para | Tetanus toxoid |
| —O(CH$_2$)$_{30}$SH | Meta | KLH |
| —O(CH$_2$)$_{30}$SH | Meta | Diptheria CRM$_{197}$ |
| —O(CH$_2$)$_{30}$SH | Meta | Tetanus toxoid |
| ‡—X$_{11}$COOH | Para | KLH |
| ‡—X$_{11}$COOH | Para | Diptheria CRM$_{197}$ |
| ‡—X$_{11}$COOH | Para | Tetanus toxoid |
| ‡—X$_{11}$COOH | Meta | KLH |
| ‡—X$_{11}$COOH | Meta | Diptheria CRM$_{197}$ |
| ‡—X$_{11}$COOH | Meta | Tetanus toxoid |
| ‡—X$_{12}$COOH | Para | KLH |
| ‡—X$_{12}$COOH | Para | Diptheria CRM$_{197}$ |
| ‡—X$_{12}$COOH | Para | Tetanus toxoid |
| ‡—X$_{12}$COOH | Meta | KLH |
| ‡—X$_{12}$COOH | Meta | Diptheria CRM$_{197}$ |
| ‡—X$_{12}$COOH | Meta | Tetanus toxoid |
| ‡—X$_{13}$COOH | Para | KLH |
| ‡—X$_{13}$COOH | Para | Diptheria CRM$_{197}$ |
| ‡—X$_{13}$COOH | Para | Tetanus toxoid |
| ‡—X$_{13}$COOH | Meta | KLH |
| ‡—X$_{13}$COOH | Meta | Diptheria CRM$_{197}$ |
| ‡—X$_{13}$COOH | Meta | Tetanus toxoid |
| ‡—X$_{14}$COOH | Para | KLH |
| ‡—X$_{14}$COOH | Para | Diptheria CRM$_{197}$ |
| ‡—X$_{14}$COOH | Para | Tetanus toxoid |
| ‡—X$_{14}$COOH | Meta | KLH |
| ‡—X$_{14}$COOH | Meta | Diptheria CRM$_{197}$ |
| ‡—X$_{14}$COOH | Meta | Tetanus toxoid |
| ‡—X$_{15}$COOH | Para | KLH |
| ‡—X$_{15}$COOH | Para | Diptheria CRM$_{197}$ |
| ‡—X$_{15}$COOH | Para | Tetanus toxoid |
| ‡—X$_{15}$COOH | Meta | KLH |
| ‡—X$_{15}$COOH | Meta | Diptheria CRM$_{197}$ |
| ‡—X$_{15}$COOH | Meta | Tetanus toxoid |
| ‡—X$_{16}$COOH | Para | KLH |
| ‡—X$_{16}$COOH | Para | Diptheria CRM$_{197}$ |
| ‡—X$_{16}$COOH | Para | Tetanus toxoid |
| ‡—X$_{16}$COOH | Meta | KLH |
| ‡—X$_{16}$COOH | Meta | Diptheria CRM$_{197}$ |
| ‡—X$_{16}$COOH | Meta | Tetanus toxoid |
| ‡—X$_{17}$COOH | Para | KLH |
| ‡—X$_{17}$COOH | Para | Diptheria CRM$_{197}$ |
| ‡—X$_{17}$COOH | Para | Tetanus toxoid |
| ‡—X$_{17}$COOH | Meta | KLH |
| ‡—X$_{17}$COOH | Meta | Diptheria CRM$_{197}$ |
| ‡—X$_{17}$COOH | Meta | Tetanus toxoid |
| ‡—X$_{18}$COOH | Para | KLH |
| ‡—X$_{18}$COOH | Para | Diptheria CRM$_{197}$ |
| ‡—X$_{18}$COOH | Para | Tetanus toxoid |
| ‡—X$_{18}$COOH | Meta | KLH |
| ‡—X$_{18}$COOH | Meta | Diptheria CRM$_{197}$ |
| ‡—X$_{18}$COOH | Meta | Tetanus toxoid |
| ‡—X$_{19}$COOH | Para | KLH |
| ‡—X$_{19}$COOH | Para | Diptheria CRM$_{197}$ |
| ‡—X$_{19}$COOH | Para | Tetanus toxoid |
| ‡—X$_{19}$COOH | Meta | KLH |
| ‡—X$_{19}$COOH | Meta | Diptheria CRM$_{197}$ |
| ‡—X$_{19}$COOH | Meta | Tetanus toxoid |
| ‡—X$_{20}$COOH | Para | KLH |
| ‡—X$_{20}$COOH | Para | Diptheria CRM$_{197}$ |
| ‡—X$_{20}$COOH | Para | Tetanus toxoid |
| ‡—X$_{20}$COOH | Meta | KLH |
| ‡—X$_{20}$COOH | Meta | Diptheria CRM$_{197}$ |
| ‡—X$_{20}$COOH | Meta | Tetanus toxoid |
| ‡—X$_{21}$COOH | Para | KLH |
| ‡—X$_{21}$COOH | Para | Diptheria CRM$_{197}$ |
| ‡—X$_{21}$COOH | Para | Tetanus toxoid |
| ‡—X$_{21}$COOH | Meta | KLH |
| ‡—X$_{21}$COOH | Meta | Diptheria CRM$_{197}$ |
| ‡—X$_{21}$COOH | Meta | Tetanus toxoid |
| ‡—X$_{22}$COOH | Para | KLH |
| ‡—X$_{22}$COOH | Para | Diptheria CRM$_{197}$ |
| ‡—X$_{22}$COOH | Para | Tetanus toxoid |
| ‡—X$_{22}$COOH | Meta | KLH |
| ‡—X$_{22}$COOH | Meta | Diptheria CRM$_{197}$ |
| ‡—X$_{22}$COOH | Meta | Tetanus toxoid |
| ‡—X$_{23}$COOH | Para | KLH |
| ‡—X$_{23}$COOH | Para | Diptheria CRM$_{197}$ |
| ‡—X$_{23}$COOH | Para | Tetanus toxoid |
| ‡—X$_{23}$COOH | Meta | KLH |
| ‡—X$_{23}$COOH | Meta | Diptheria CRM$_{197}$ |
| ‡—X$_{23}$COOH | Meta | Tetanus toxoid |
| ‡—X$_{24}$COOH | Para | KLH |
| ‡—X$_{24}$COOH | Para | Diptheria CRM$_{197}$ |
| ‡—X$_{24}$COOH | Para | Tetanus toxoid |
| ‡—X$_{24}$COOH | Meta | KLH |
| ‡—X$_{24}$COOH | Meta | Diptheria CRM$_{197}$ |
| ‡—X$_{24}$COOH | Meta | Tetanus toxoid |
| ‡—X$_{25}$COOH | Para | KLH |
| ‡—X$_{25}$COOH | Para | Diptheria CRM$_{197}$ |
| ‡—X$_{25}$COOH | Para | Tetanus toxoid |
| ‡—X$_{25}$COOH | Meta | KLH |
| ‡—X$_{25}$COOH | Meta | Diptheria CRM$_{197}$ |
| ‡—X$_{25}$COOH | Meta | Tetanus toxoid |
| ‡—X$_{27}$COOH | Para | KLH |
| ‡—X$_{27}$COOH | Para | Diptheria CRM$_{197}$ |
| ‡—X$_{27}$COOH | Para | Tetanus toxoid |
| ‡—X$_{27}$COOH | Meta | KLH |
| ‡—X$_{27}$COOH | Meta | Diptheria CRM$_{197}$ |
| ‡—X$_{27}$COOH | Meta | Tetanus toxoid |
| ‡—X$_{28}$COOH | Para | KLH |
| ‡—X$_{28}$COOH | Para | Diptheria CRM$_{197}$ |
| ‡—X$_{28}$COOH | Para | Tetanus toxoid |
| ‡—X$_{28}$COOH | Meta | KLH |
| ‡—X$_{28}$COOH | Meta | Diptheria CRM$_{197}$ |
| ‡—X$_{28}$COOH | Meta | Tetanus toxoid |
| ‡—X$_{29}$COOH | Para | KLH |
| ‡—X$_{29}$COOH | Para | Diptheria CRM$_{197}$ |
| ‡—X$_{29}$COOH | Para | Tetanus toxoid |
| ‡—X$_{29}$COOH | Meta | KLH |
| ‡—X$_{29}$COOH | Meta | Diptheria CRM$_{197}$ |
| ‡—X$_{29}$COOH | Meta | Tetanus toxoid |
| ‡—X$_{30}$COOH | Para | KLH |
| ‡—X$_{30}$COOH | Para | Diptheria CRM$_{197}$ |
| ‡—X$_{30}$COOH | Para | Tetanus toxoid |
| ‡—X$_{30}$COOH | Meta | KLH |
| ‡—X$_{30}$COOH | Meta | Diptheria CRM$_{197}$ |
| ‡—X$_{30}$COOH | Meta | Tetanus toxoid |
| ‡—X$_7$SH | Para | KLH |
| ‡—X$_7$SH | Para | Diptheria CRM$_{197}$ |
| ‡—X$_7$SH | Para | Tetanus toxoid |
| ‡—X$_7$SH | Meta | KLH |
| ‡—X$_7$SH | Meta | Diptheria CRM$_{197}$ |
| ‡—X$_7$SH | Meta | Tetanus toxoid |
| ‡—X$_8$SH | Para | KLH |
| ‡—X$_8$SH | Para | Diptheria CRM$_{197}$ |
| ‡—X$_8$SH | Para | Tetanus toxoid |
| ‡—X$_8$SH | Meta | KLH |
| ‡—X$_8$SH | Meta | Diptheria CRM$_{197}$ |
| ‡—X$_8$SH | Meta | Tetanus toxoid |
| ‡—X$_9$SH | Para | KLH |
| ‡—X$_9$SH | Para | Diptheria CRM$_{197}$ |
| ‡—X$_9$SH | Para | Tetanus toxoid |
| ‡—X$_9$SH | Meta | KLH |
| ‡—X$_9$SH | Meta | Diptheria CRM$_{197}$ |

TABLE B-continued

| L Group | Position on Ring | Carrier |
|---|---|---|
| ‡—$X_9$SH | Meta | Tetanus toxoid |
| ‡—$X_{10}$SH | Para | KLH |
| ‡—$X_{10}$SH | Para | Diptheria $CRM_{197}$ |
| ‡—$X_{10}$SH | Para | Tetanus toxoid |
| ‡—$X_{10}$SH | Meta | KLH |
| ‡—$X_{10}$SH | Meta | Diptheria $CRM_{197}$ |
| ‡—$X_{10}$SH | Meta | Tetanus toxoid |
| ‡—$X_{11}$SH | Para | KLH |
| ‡—$X_{11}$SH | Para | Diptheria $CRM_{197}$ |
| ‡—$X_{11}$SH | Para | Tetanus toxoid |
| ‡—$X_{11}$SH | Meta | KLH |
| ‡—$X_{11}$SH | Meta | Diptheria $CRM_{197}$ |
| ‡—$X_{11}$SH | Meta | Tetanus toxoid |
| ‡—$X_{12}$SH | Para | KLH |
| ‡—$X_{12}$SH | Para | Diptheria $CRM_{197}$ |
| ‡—$X_{12}$SH | Para | Tetanus toxoid |
| ‡—$X_{12}$SH | Meta | KLH |
| ‡—$X_{12}$SH | Meta | Diptheria $CRM_{197}$ |
| ‡—$X_{12}$SH | Meta | Tetanus toxoid |
| ‡—$X_{13}$SH | Para | KLH |
| ‡—$X_{13}$SH | Para | Diptheria $CRM_{197}$ |
| ‡—$X_{13}$SH | Para | Tetanus toxoid |
| ‡—$X_{13}$SH | Meta | KLH |
| ‡—$X_{13}$SH | Meta | Diptheria $CRM_{197}$ |
| ‡—$X_{13}$SH | Meta | Tetanus toxoid |
| ‡—$X_{14}$SH | Para | KLH |
| ‡—$X_{14}$SH | Para | Diptheria $CRM_{197}$ |
| ‡—$X_{14}$SH | Para | Tetanus toxoid |
| ‡—$X_{14}$SH | Meta | KLH |
| ‡—$X_{14}$SH | Meta | Diptheria $CRM_{197}$ |
| ‡—$X_{14}$SH | Meta | Tetanus toxoid |
| ‡—$X_{15}$SH | Para | KLH |
| ‡—$X_{15}$SH | Para | Diptheria $CRM_{197}$ |
| ‡—$X_{15}$SH | Para | Tetanus toxoid |
| ‡—$X_{15}$SH | Meta | KLH |
| ‡—$X_{15}$SH | Meta | Diptheria $CRM_{197}$ |
| ‡—$X_{15}$SH | Meta | Tetanus toxoid |
| ‡—$X_{16}$SH | Para | KLH |
| ‡—$X_{16}$SH | Para | Diptheria $CRM_{197}$ |
| ‡—$X_{16}$SH | Para | Tetanus toxoid |
| ‡—$X_{16}$SH | Meta | KLH |
| ‡—$X_{16}$SH | Meta | Diptheria $CRM_{197}$ |
| ‡—$X_{16}$SH | Meta | Tetanus toxoid |
| ‡—$X_{17}$SH | Para | KLH |
| ‡—$X_{17}$SH | Para | Diptheria $CRM_{197}$ |
| ‡—$X_{17}$SH | Para | Tetanus toxoid |
| ‡—$X_{17}$SH | Meta | KLH |
| ‡—$X_{17}$SH | Meta | Diptheria $CRM_{197}$ |
| ‡—$X_{17}$SH | Meta | Tetanus toxoid |
| ‡—$X_{18}$SH | Para | KLH |
| ‡—$X_{18}$SH | Para | Diptheria $CRM_{197}$ |
| ‡—$X_{18}$SH | Para | Tetanus toxoid |
| ‡—$X_{18}$SH | Meta | KLH |
| ‡—$X_{18}$SH | Meta | Diptheria $CRM_{197}$ |
| ‡—$X_{18}$SH | Meta | Tetanus toxoid |
| ‡—$X_{19}$SH | Para | KLH |
| ‡—$X_{19}$SH | Para | Diptheria $CRM_{197}$ |
| ‡—$X_{19}$SH | Para | Tetanus toxoid |
| ‡—$X_{19}$SH | Meta | KLH |
| ‡—$X_{19}$SH | Meta | Diptheria $CRM_{197}$ |
| ‡—$X_{19}$SH | Meta | Tetanus toxoid |
| ‡—$X_{20}$SH | Para | KLH |
| ‡—$X_{20}$SH | Para | Diptheria $CRM_{197}$ |
| ‡—$X_{20}$SH | Para | Tetanus toxoid |
| ‡—$X_{20}$SH | Meta | KLH |
| ‡—$X_{20}$SH | Meta | Diptheria $CRM_{197}$ |
| ‡—$X_{20}$SH | Meta | Tetanus toxoid |
| ‡—$X_{21}$SH | Para | KLH |
| ‡—$X_{21}$SH | Para | Diptheria $CRM_{197}$ |
| ‡—$X_{21}$SH | Para | Tetanus toxoid |
| ‡—$X_{21}$SH | Meta | KLH |
| ‡—$X_{21}$SH | Meta | Diptheria $CRM_{197}$ |
| ‡—$X_{21}$SH | Meta | Tetanus toxoid |
| ‡—$X_{22}$SH | Para | KLH |
| ‡—$X_{22}$SH | Para | Diptheria $CRM_{197}$ |
| ‡—$X_{22}$SH | Para | Tetanus toxoid |
| ‡—$X_{22}$SH | Meta | KLH |
| ‡—$X_{22}$SH | Meta | Diptheria $CRM_{197}$ |
| ‡—$X_{22}$SH | Meta | Tetanus toxoid |
| ‡—$X_{23}$SH | Para | KLH |
| ‡—$X_{23}$SH | Para | Diptheria $CRM_{197}$ |
| ‡—$X_{23}$SH | Para | Tetanus toxoid |
| ‡—$X_{23}$SH | Meta | KLH |
| ‡—$X_{23}$SH | Meta | Diptheria $CRM_{197}$ |
| ‡—$X_{23}$SH | Meta | Tetanus toxoid |
| ‡—$X_{24}$SH | Para | KLH |
| ‡—$X_{24}$SH | Para | Diptheria $CRM_{197}$ |
| ‡—$X_{24}$SH | Para | Tetanus toxoid |
| ‡—$X_{24}$SH | Meta | KLH |
| ‡—$X_{24}$SH | Meta | Diptheria $CRM_{197}$ |
| ‡—$X_{24}$SH | Meta | Tetanus toxoid |
| ‡—$X_{25}$SH | Para | KLH |
| ‡—$X_{25}$SH | Para | Diptheria $CRM_{197}$ |
| ‡—$X_{25}$SH | Para | Tetanus toxoid |
| ‡—$X_{25}$SH | Meta | KLH |
| ‡—$X_{25}$SH | Meta | Diptheria $CRM_{197}$ |
| ‡—$X_{25}$SH | Meta | Tetanus toxoid |
| ‡—$X_{26}$SH | Para | KLH |
| ‡—$X_{26}$SH | Para | Diptheria $CRM_{197}$ |
| ‡—$X_{26}$SH | Para | Tetanus toxoid |
| ‡—$X_{26}$SH | Meta | KLH |
| ‡—$X_{26}$SH | Meta | Diptheria $CRM_{197}$ |
| ‡—$X_{26}$SH | Meta | Tetanus toxoid |
| ‡—$X_{27}$SH | Para | KLH |
| ‡—$X_{27}$SH | Para | Diptheria $CRM_{197}$ |
| ‡—$X_{27}$SH | Para | Tetanus toxoid |
| ‡—$X_{27}$SH | Meta | KLH |
| ‡—$X_{27}$SH | Meta | Diptheria $CRM_{197}$ |
| ‡—$X_{27}$SH | Meta | Tetanus toxoid |
| ‡—$X_{28}$SH | Para | KLH |
| ‡—$X_{28}$SH | Para | Diptheria $CRM_{197}$ |
| ‡—$X_{28}$SH | Para | Tetanus toxoid |
| ‡—$X_{28}$SH | Meta | KLH |
| ‡—$X_{28}$SH | Meta | Diptheria $CRM_{197}$ |
| ‡—$X_{28}$SH | Meta | Tetanus toxoid |
| ‡—$X_{29}$SH | Para | KLH |
| ‡—$X_{29}$SH | Para | Diptheria $CRM_{197}$ |
| ‡—$X_{29}$SH | Para | Tetanus toxoid |
| ‡—$X_{29}$SH | Meta | KLH |
| ‡—$X_{29}$SH | Meta | Diptheria $CRM_{197}$ |
| ‡—$X_{29}$SH | Meta | Tetanus toxoid |
| ‡—$X_{30}$SH | Para | KLH |
| ‡—$X_{30}$SH | Para | Diptheria $CRM_{197}$ |
| ‡—$X_{30}$SH | Para | Tetanus toxoid |
| ‡—$X_{30}$SH | Meta | KLH |
| ‡—$X_{30}$SH | Meta | Diptheria $CRM_{197}$ |
| ‡—$X_{30}$SH | Meta | Tetanus toxoid |

‡wherein X may be any atom selected from the group comprising C, O, N, P and S; including the appropriate number of hydrogens to balance charge.

III. Conjugation Chemistry

The compounds detailed in part (II) corresponding to formulas (VI), (VII), (VIII), (IX), and (X) may be made by a variety of methods generally known in the art or as described herein. Irrespective of the process utilized for conjugation of a hapten compound to a carrier molecule (X) via a linker (L), the process selected will typically result in a compound having a relatively high epitope density, i.e., the number of hapten compounds conjugated to a single carrier molecule, (X), as expressed above as n. The conjugation method used will depend upon the chemistry of coupling a particular hapten compound to a molecular carrier. In general, a reactive site on a first compound is linked to a reactive site on a second compound, using a coupling agent or catalyst. Two exemplary processes are described below in more detail.

Figure 9:
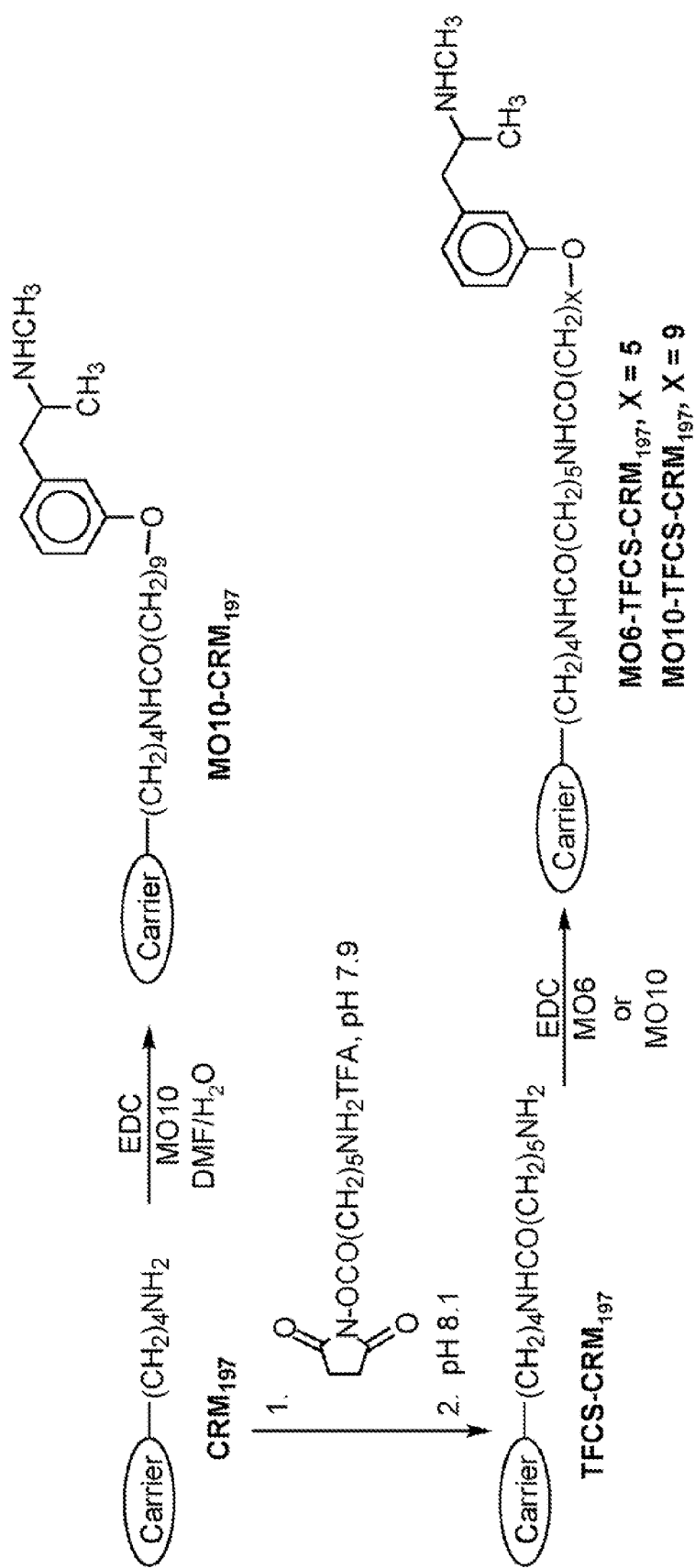
FIG. 9 presents a diagram illustrating a method of preparing a hapten conjugate with an amide-connection. The method comprises coupling of MO10 directly to $CRM_{197}$ using 1-ethyl-3-[3-dimethylaminopropyl]carbodiimide hydrochloride (EDC), or, to provide conjugates with different linkers, the conversion of $CRM_{197}$ to TFCS-$CRM_{197}$ by N-(ε-trifluoracetylcaproloxy)succinimide ester (TFCS), then coupling to MO6 and MO10 using EDC to give MO6-TFCS-$CRM_{197}$ or MO10-TFCS-$CRM_{197}$.

Referring to FIG. 9, in an exemplary embodiment to form compounds having formula (VII) or (VIII) the hapten compound may be conjugated via the linker (L) to a carrier molecule (X) by formation of an amide bond. Generally speaking, the carboxyl group of the linker is reacted with an amide group on the carrier molecule. However, in certain embodiments, the carboxyl group of the linker may be reacted with a second linker that is reacted with an amide group on the carrier molecule. Such second linkers may be homobifunctional or heterobifunctional linkers, and are well known in the art. Suitable coupling agents may include EDC, Carbodiimide-HCL, glutaraldehyde and other similar agents. In one embodiment, L of formula (II) or (III) may be conjugated to X by reaction with EDC (1-ethyl-3-[3-dimethylaminopropyl] carbodiimide hydrochloride) (see FIG. 9). Alternatively, X may be reacted with TFCS, and then reacted with EDC to form an amide bond with L of formula (II) or (III) (see FIG. 9).

Typically, in a conjugation reaction, i.e. a synthesis reaction, that is based on an amide bond, the ratio of carrier molecule to hapten compound may be between about 1:25 and about 1:100. In one embodiment, the ratio may be between about 1:25 and about 1:50. In another embodiment, the ratio may be between about 1:50 and about 1:75. In yet another embodiment, the ratio may be between about 1:75 and about 1:100. In still another embodiment, the ratio may be between about 1:30 and about 1:90.

Generally speaking, the ratio of carrier molecule to hapten compound for a conjugation reaction should be determined to maximize the number of hapten compounds conjugated to the molecular carrier (i.e. n, as described in formulas (VI), (VII), and (VIII). Generally, n is an integer greater than or equal to 3. In one embodiment, n may be 3, 4, or 5. In another embodiment, n may be 6, 7, 8, or 9. In yet another embodiment, n may be 10, 11, 12, or 13 or more. In an exemplary embodiment, n is greater than or equal to 5. The ratio of carrier molecule to hapten compound may be determined by MALDI MS.

Figure 10:
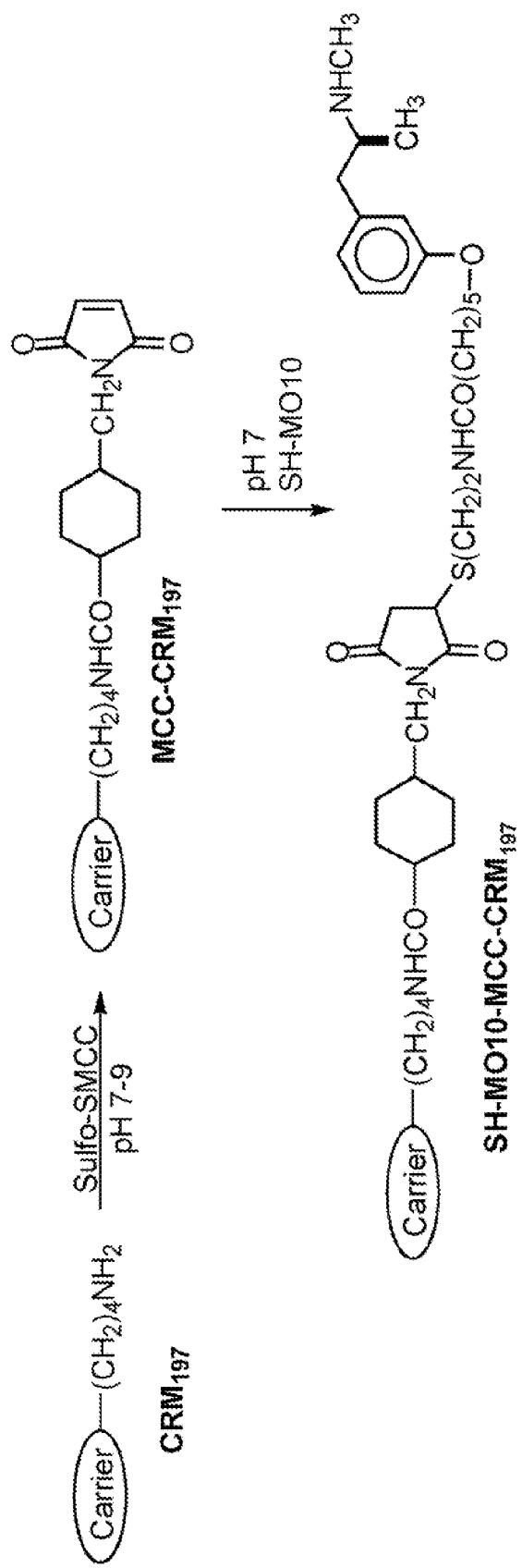
FIG. 10 presents a diagram illustrating a method of preparing a hapten conjugate with a sulfide-connection. The method comprises reacting $CRM_{197}$ with sulfosuccinimidyl 4-[N-maleimidomethyl]cyclohexane-1 carboxylate (Sulfo-SMCC) at pH 7-9 to provide the stable maleimide-activated MCC-$CRM_{197}$. Addition of SH-MO10 to MCC-$CRM_{197}$ at pH7 will provide the conjugate SH-MO10-MCC-$CRM_{197}$.

Referring to FIG. 10, in an exemplary embodiment to form compounds having formula (IX) or (X) the hapten compound may be conjugated via the linker (L) to a carrier molecule (X) by formation of a sulfide bond. Generally speaking, the sulfide group of the linker is reacted with an active group on the carrier molecule. However, in certain embodiments, the sulfide group of the linker may be reacted with a second linker that is reacted with an active group on the carrier molecule. Such second linkers may be homobifunctional or heterobifunctional linkers, and are well known in the art. An example of an exemplary active group on the carrier molecule is maleimide. In one embodiment, X may be activated with Sulfo-SMCC, and then reacted with a compound of formula (IV) or (V) to form a sulfide bond (see FIG. 9).

Typically, in a conjugation reaction, i.e. a synthesis reaction, that is based on a sulfide bond, the ratio of carrier molecule to hapten compound may be between about 1:25 and about 1:100. In one embodiment, the ratio may be between about 1:25 and about 1:50. In another embodiment, the ratio may be between about 1:50 and about 1:75. In yet another embodiment, the ratio may be between about 1:75 and about 1:100. In still another embodiment, the ratio may be between about 1:30 and about 1:90.

The ratio of carrier molecule to hapten compound should be selected to maximize the number of hapten compounds conjugated to the molecular carrier (i.e. n, as described in formulas (VI), (IX), and (X)). Generally, n is an integer greater than or equal to 3. In one embodiment, n may be 3, 4, or 5. In another embodiment, n may be 6, 7, 8, or 9. In yet another embodiment, n may be 10, 11, 12, or 13 or more. In an exemplary embodiment, n is greater than or equal to 5. The ratio of carrier molecule to hapten compound may be determined by MALDI MS.

IV. Immunogenic Compositions Comprising Hapten Compounds

An additional aspect of the invention encompasses an immunogenic composition comprising a hapten compound. In some embodiments, the immunogenic composition may comprise a compound selected from the group consisting of a compound of formula (I), a compound of formula (II), a compound of formula (III), a compound of formula (IV), a compound of formula (V), a compound of formula (VI), a compound of formula (VII), a compound of formula (VIII), a compound of formula (IX), and a compound of formula (X). In one embodiment, the immunogenic composition may comprise a compound of formula (I). In another embodiment, the immunogenic composition may comprise a compound of formula (II). In yet another embodiment, the immunogenic composition may comprise a compound of formula (III). In still another embodiment, the immunogenic composition may comprise a compound of formula (IV). In yet still another embodiment, the immunogenic composition may comprise a compound of formula (V). In an additional embodiment, the immunogenic composition may comprise a compound of formula (VI). In another additional embodiment, the immunogenic composition may comprise a compound of formula (VII). In still another additional embodiment, the immunogenic composition may comprise a compound of formula (VIII). In yet another additional embodiment, the immunogenic composition may comprise a compound of formula (IX). In yet still another additional embodiment, the immunogenic composition may comprise a compound of formula (X).

In certain embodiments, an immunogenic composition comprising a hapten compound of the invention may further comprise an adjuvant. Generally speaking, an adjuvant may be used to increase the immune response to a hapten compound of the invention. For instance, an adjuvant may be used to increase antibody affinity, antibody titer, and the duration of the immune response in a subject. Non-limiting examples of adjuvants may include alum, TiterMax Gold, Ribi, ASO4, Freund's complete adjuvant, and Freund's incomplete adjuvant. In one embodiment, the adjuvant may be alum. In another embodiment, the adjuvant may be TiterMax Gold. In yet another embodiment, the adjuvant may be Ribi. In still another embodiment, the adjuvant may be ASO4. In still yet another embodiment, the adjuvant may be Freund's complete adjuvant. In an additional embodiment, the adjuvant may be Freund's incomplete adjuvant. In an exemplary embodiment, the adjuvant is pharmaceutically acceptable for use in a human subject. Generally speaking, a pharmaceutically acceptable adjuvant is pyrogen free and will not induce anaphylactic shock in a subject. Non-limiting examples of pharmaceutically acceptable adjuvants for use in humans include alum and ASO4.

In some embodiments, an immunogenic composition comprising a hapten compound may further comprise a pharmaceutically acceptable carrier, as described in section II above. Briefly, a pharmaceutically acceptable carrier safely elicits an antibody response in a subject. In this context, safely means that the carrier does not substantially elicit an immune response that cross-reacts with a self-protein, or a regularly ingested protein of the subject. In one embodiment, the pharmaceutically acceptable carrier may be a bacterial toxin or a bacterial toxoid. In another embodiment, the pharmaceutically acceptable carrier may be a mutant diphtheria toxoid, for instance, $CRM_{197}$. In yet another embodiment, the pharmaceutically acceptable carrier may be tetanus toxoid.

In certain embodiments, it is envisioned that a particular molecular carrier may be conjugated to more than one type of hapten compound. For instance, a particular molecular carrier may be conjugated to a hapten compound of formula (II) and formula (IV). Alternatively, a particular molecular carrier may be conjugated to at least two hapten compounds listed in Table A.

In further embodiments, an immunogenic composition comprising a hapten compound may further comprise an adjuvant and a pharmaceutically acceptable carrier. In some embodiments, an immunogenic composition of the invention may comprise a combination of an adjuvant and carrier listed in Table C.

TABLE C

| Adjuvant | Carrier |
|---|---|
| alum | Diptheria $CRM_{197}$ |
| alum | Tetanus Toxoid |
| alum | KLH |
| Titermax gold | Diptheria $CRM_{197}$ |
| Titermax gold | Tetanus Toxoid |
| Titermax gold | KLH |
| ASO4 | Diptheria $CRM_{197}$ |
| ASO4 | Tetanus Toxoid |
| ASO4 | KLH |
| Ribi | Diptheria $CRM_{197}$ |
| Ribi | Tetanus Toxoid |
| Ribi | KLH |
| Freund's complete adjuvant | Diptheria $CRM_{197}$ |
| Freund's complete adjuvant | Tetanus Toxoid |
| Freund's complete adjuvant | KLH |
| Freund's incomplete adjuvant | Diptheria $CRM_{197}$ |
| Freund's incomplete adjuvant | Tetanus Toxoid |
| Freund's incomplete adjuvant | KLH |

In an alternative embodiment, an immunogenic composition comprising a hapten compound may further comprise a pharmaceutically acceptable excipient. Non-limiting examples of pharmaceutically acceptable excipients include sterile water, salt solutions such as saline, sodium phosphate, sodium chloride, alcohol, gum arabic, vegetable oils, benzyl alcohols, polyethylene glycol, gelatine, mannitol, carbohydrates, magnesium stearate, viscous paraffin, fatty acid esters, hydroxy methyl cellulose, and buffer. Other suitable excipients may be used by those skilled in that art.

V. Eliciting an Immune Response

Another additional aspect of the invention encompasses administering a hapten compound to a subject to elicit an immune response in the subject. Typically, such an immune response will generate specific antibodies that recognize one or more of (+)methamphetamine, (+)amphetamine, and (+)MDMA. In one embodiment, the specific antibodies may recognize two compounds from the group consisting of (+)methamphetamine, (+)amphetamine, and (+)MDMA. In an exemplary embodiment, the specific antibodies may recognize all three compounds of the group consisting of (+)methamphetamine, (+)amphetamine, and (+)MDMA. In another exemplary embodiment, the specific antibodies may recognize all three compounds of the group consisting of (+)methamphetamine, (+)amphetamine, and (+)MDMA, and not substantially cross-react with (−)methamphetamine, (−)amphetamine, and (−)MDMA. In still another exemplary embodiment, the specific antibodies may recognize all three compounds of the group consisting of (+)methamphetamine, (+)amphetamine, and (+)MDMA, and not substantially cross-react with over the counter medications.

In one embodiment, the elicited immune response may generate antibodies specific for a compound administered to a subject. In certain embodiments, a method for generating specific antibodies for a compound selected from the group consisting of a compound of formula (I), a compound of formula (II), a compound of formula (III), a compound of formula (IV), a compound of formula (V), a compound of formula (VI), a compound of formula (VII), a compound of formula (VIII), a compound of formula (IX), and a compound of formula (X) may comprise administering the compound to a subject. In another embodiment, the elicited immune response may generate antibodies specific for more than one hapten compound of the invention administered to a subject. For instance, a compound of formula (II) and a compound of formula (IV) may be administered to a subject simultaneously, contemporaneously, or sequentially. Alternatively, more than one compound listed in Table A may be administered to a subject simultaneously, contemporaneously, or sequentially.

As used herein, subject refers to any vertebrate capable of mounting an immune response. In one embodiment, a subject may be a rodent. Non-limiting examples of rodents include mice and rats. In another embodiment, a subject may be a livestock animal. Non-limiting examples of livestock animals include cows, pigs, sheep, goats, llamas, and poultry. In still another embodiment, a subject may be a companion animal. Non-limiting examples of companion animals include dogs, cats, rabbits, and horses. In an additional embodiment, a subject may be a primate. Non-limiting examples of primates include lemurs, monkeys, apes, and humans. In a further embodiment, a subject may be a non-human primate. In an alternative embodiment, a subject may be human.

In each of the above embodiments, the subjects may be subjects using (+)methamphetamine, (+)amphetamine, and/or (+)MDMA (and/or ecstasy). Alternatively, the subjects may be at risk for using (+)methamphetamine, (+)amphetamine, and/or (+)MDMA (and/or ecstasy). In another alternative, the subjects may be recovering from using (+) methamphetamine, (+)amphetamine, and/or (+)MDMA (and/or ecstasy). In yet another alternative, the subjects may be trying to stop using (+)methamphetamine, (+)amphetamine, and/or (+)MDMA (and/or ecstasy) under medical supervision.

One skilled in the art will appreciate that a hapten compound of the invention may be administered in a variety of ways to elicit an immune response. (See generally, Herbert and Fristensen (1986) and Poole (1987).) Generally speaking, the method of administration will depend on the volume of the composition administered, the solubility of the composition, and on the speed of the immune response desired. Moreover, the method of administration may be limited by the subject involved. Typically, a method of administration should be chosen that provides increased antibody titer, affinity, and duration of antibody response. Non-limiting examples of possible administration methods include subcutaneous administration, intraperitoneal administration, intravenous administration, intramuscular administration and intradermal administration. In one embodiment, a composition comprising a hapten compound of the invention may be administered subcutaneously. In another embodiment, a composition may be administered intraperitoneally. In yet another embodiment, a composition may be administered intravenously. In still another embodiment, a composition may be administered intramuscularly. In still yet another embodiment, a composition may be administered intradermally.

The dosage of hapten compound administered will typically vary with the subject involved. Generally speaking, in formulating a dosage to be administered, one skilled in the art should consider the weight of the subject and the method of administration. Moreover, the dosage may be chosen to increase antibody titer, antibody affinity, and/or duration of antibody response. For instance, a high dosage may lead to higher titer antibodies, but lower affinity antibodies. In one embodiment, the dosage used may be the lowest dosage possible to generate an antibody response in at least 70% of the subjects involved. In another embodiment, the dosage used may be the lowest dosage possible to generate an antibody response in at least 75%, 80%, 85%, or 90% of the subjects involved. In yet another embodiment, the dosage used may be the lowest dosage possible to generate an antibody response in at least 91%, 92%, 93%, 94%, 95%, 96%, 97%, 98%, or 99% of the subjects involved. In still yet another embodiment, the dosage used may be the lowest dosage possible to generate an antibody response in 100% of the subjects involved. Non-limiting examples of specific dosages for various subjects may be found in the examples.

The schedule of administration should also, generally speaking, be chosen to increase antibody titer, antibody affinity, and the duration of immune response. For instance, a subject might be initially administered a hapten compound of the invention, and then receive booster administrations thereafter. The frequency and number of booster administrations can and will vary with the subject involved. Frequent administrations may increase titer, but not affinity. Alternatively, less frequent administrations may result in increased affinity. For instance, in humans, a schedule may include booster administrations for one or more years following the initial administration. Non-limiting examples of booster schedules may be found in the examples.

VI. Uses for the Specific Antibodies

A further aspect of the invention encompasses both therapeutic and non-therapeutic uses for the specific antibodies generated using the methods of section V above.

In certain embodiments, the specific antibodies may be used in non-therapeutic assays, such as immunostaining, immunoprecipitation, immunoblotting, immunoaffinity purification, and ELISAs. In one embodiment, the specific antibodies may be used for immunostaining. In another embodiment, the specific antibodies may be used for immunoprecipitation. In yet another embodiment, the specific antibodies may be used for immunoblotting. In still another embodiment, the specific antibodies may be used for immunoaffinity purification. In still yet another embodiment, the specific antibodies may be used for ELISAs. Protocols for each of the above non-therapeutic uses are well known in the art, and may be found, for instance, in Harlow and Lane, *Antibodies*, Cold Spring Harbor, 1988, Chapters 9-14.

Additionally, the specific antibodies may be used for therapeutic purposes. Generally speaking, the specific antibodies may be used to antagonize the effects of (+)methamphetamine, (+)amphetamine, and/or (+)MDMA in a subject. In certain embodiments, the subjects may be using (+)methamphetamine, (+)amphetamine, and/or (+)MDMA. For instance, in one embodiment, the specific antibodies may antagonize the effects of (+)methamphetamine, (+)amphetamine, and/or (+)MDMA in a subject by decreasing the concentration of (+)methamphetamine, (+)amphetamine, or (+)MDMA in the brain of a subject. In another embodiment, the specific antibodies may be used to decrease drug-seeking behavior in a subject. In yet another embodiment, the specific antibodies may be used to decrease self-dosing behavior in a subject.

In each of the above embodiments, the specific antibodies may be administered passively, actively, or in a combination of passive and active administration. Active administration typically refers to administering a hapten compound of the invention to a subject so as the subject generates antibodies in vivo. Passive administration typically refers to administering at least one specific antibody, generated by a first subject or produced via ex vivo methods, into a second subject.

In one embodiment, the invention may encompass a method of treating drug use. The method may comprise eliciting an immune response in a drug-using subject by administering a hapten composition to a subject, wherein the immune response decreases the concentration of (+)methamphetamine, (+)amphetamine, or (+)MDMA in the brain of the subject.

DEFINITIONS

To facilitate understanding of the invention, a number of terms are defined below:

As used herein "(d)" stands for dextrorotatory and (l) stands for levorotatory, and refers to the direction in which an enantiomer rotates the plane of polarized light. Herein, (d) is used interchangeably with (+), and (l) is used interchangeably with (−).

Unless otherwise indicated, the alkyl groups described herein are preferably lower alkyl containing from one to eight carbon atoms in the principal chain and up to 30 carbon atoms or more. They may be straight or branched chain or cyclic and include methyl, ethyl, propyl, isopropyl, butyl, hexyl and the like. Unless otherwise indicated, the alkenyl groups described herein are preferably lower alkenyl containing from two to eight carbon atoms in the principal chain and up to 30 carbon atoms or more. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 30 carbon atoms or more. They may be straight or branched chain and include ethynyl, propynyl, butynyl, isobutynyl, hexynyl, and the like.

As used herein, antibody generally means a polypeptide or protein that recognizes and can bind to an epitope of an antigen. An antibody, as used herein, may be a complete antibody as understood in the art, i.e., consisting of two heavy chains and two light chains, or be selected from a group comprising polyclonal antibodies, ascites, Fab fragments, Fab' fragments, monoclonal antibodies, chimeric antibodies, human antibodies, humanized antibodies, and a peptide comprising a hypervariable and/or framework region of an antibody.

As used herein, antibody affinity refers to the attraction between an antibody and a target epitope. Affinity may be measured by calculating a $K_D$ value for a particular antibody and a particular epitope. Typically, affinity can be equated with $(1/K_D)$. "$K_D$" as used herein, refers to disassociation constant. Methods of calculating $K_D$ values are well known in the art.

As used herein, antibody titer refers to the concentration of antibodies present in the highest dilution of a serum sample that inhibits the binding of target ligands by 50%. Titer may be measured using an ELISA or RIA assay, by methods commonly known in the art.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "conjugate" refers to a substance formed from the joining together of two parts. Representative conjugates in accordance with the present invention include those formed by the joining together of a small molecule and a large molecule, such as a protein. Methamphetamine attached to a carrier protein via a linker is an example of conjugation.

The term "contiguous" is used herein to describe the number of atoms forming a linker. The number of atoms in a linking group or linker is determined by counting the contiguous atoms other than hydrogen. In this context, "contiguous" is the number of atoms in a chain within a linking group determined by counting the number of atoms other than hydrogen along the shortest route between the substructures being connected.

The phrase "decreasing the concentration of (+)methamphetamine, (+)amphetamine, or (+)MDMA in the brain" may refer to either decreasing the amount of (+)methamphetamine, (+)amphetamine, or (+)MDMA in the brain, or changing the rate of entry of (+)methamphetamine, (+)amphetamine, or (+)MDMA into the brain.

The term "derivative" refers to a chemical compound or molecule made from a parent compound by one or more chemical reactions.

The term "hapten" refers to a partial or incomplete antigen. Haptens are protein-free substances that generally are not capable of stimulating antibody formation, but may react with antibodies. Amphetamine, methamphetamine, and their derivatives are haptens.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring.

The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo groups include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl.

As used herein, a "linking group" or "linker" refers to a portion of a chemical structure that connects two or more substructures such as haptens, carriers, immunogens, labels, tracers or other linkers. A linking group has at least 1 uninterrupted chain of atoms other than hydrogen (or other monovalent atoms) extending between the substructures. The atoms of a linking group and the atoms of a chain within a linking group are themselves connected by chemical bonds. Linkers may be straight or branched, saturated or unsaturated, hydrocarbyl or substituted hydrocarbyl chains.

The term "recognize," when referring to an antibody, refers to the affinity of the antibody. Generally speaking, in order for an antibody to "recognize" multiple targets, the affinity of the antibody for each recognized target is at least within 8 fold of the antibody's affinity for each other recognized target. In an exemplary embodiment, the affinity of the antibody for each recognized target is between about 3 and about 4 fold of the antibody's affinity for each other recognized target.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents may include one or more of the following groups: halogen, carbocycle, carboxy, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various embodiments of the invention.

Example 1

Hapten Design and Antibody Selection

When generating monoclonal antibodies (mAb, plural and singular) against small molecules, the chemical composition and molecular orientation of the drug-like hapten on the antigen is a crucial determinant. This is especially important when attempting to discover therapeutic mAb against the drugs of abuse (+)-methamphetamine ((+)METH), (+)-amphetamine ((+)AMP) and the related compound (+)-3,4-methylenedioxymethamphetamine ((+)MDMA, the plus isomer in the racemic mixture known as MDMA or ecstasy). The goal of these studies was to design and synthesize (+)METH-like haptens with structural attributes that would make them effective for generating monoclonal antibodies for treating medical problems associated with these stimulant drugs of abuse.

For these studies, hapten spacers between (+)METH and the carrier protein were progressively lengthened from 4 to 10 atoms to increase the potential for greater interaction of the hapten with the antibody binding site and/or to increase flexibility of the spacer between the (+)METH backbone structure and the carrier. It was hypothesized that a progressive lengthening and flexibility of the spacer arm would lead to increased affinity and specificity due to increased access to the entire (+)METH-like structure. As a secondary strategy, the location of the linker attachment to the (+)METH structure (e.g., para and meta attachments) was varied in an attempt to elicit antibodies with different conformational selectivity for (+)METH-like compounds.

Chemicals and Drugs.

All chemicals and protein antigens were purchased from Sigma (St. Louis, Mo.), unless otherwise noted. Enzymes and E. coli strains were purchased from Invitrogen (Carlsbad, Calif.). (+)-2',6'-$^3$H(n)] methamphetamine ([$^3$H]-(+)METH; 23.5 Ci/mmol) and (±)-[2,6-$^3$H$_2$(n)]-amphetamine ([$^3$H]-(±) AMP; 45 Ci/mmol) were obtained from the National Institute on Drug Abuse (Bethesda, Md.) after synthesis at the Research Triangle Institute (Research Triangle Park, N.C.). Other METH-like drugs used in this study were also obtained from the National Institute on Drug Abuse.

[$^3$H]-(+)METH was used as sent, but the [$^3$H]-(±)AMP was chromatographically separated to obtain [$^3$H]-(+)AMP for use in our studies of (+)AMP specificity. The separation was performed on a 150×4 mm (i.d.) 5 μm CrownPak CR(+) column (Chiral Technologies Inc., Exton, Pa.). The mobile phase consisted of 0.1 M perchloric acid (Fisher Scientific) containing 10% (v/v) methanol. The column temperature was maintained at 15° C. The flow rate was 1.0 ml/min and the injection volume was 50 μL. Chromatographic peaks were detected using ultraviolet absorption detection at a wavelength of 210 nm. The retention times for [$^3$H]-(+)AMP and [$^3$H]-(−)AMP were 20.1 min and 24.4 min, respectively.

Haptens and Hapten-Protein Conjugation.

Five different stereospecific (+)-isomer (+)METH-like haptens were synthesized. All haptens were synthesized as HCl salts to aid in solubility, and stored as solids or powders until used. The chemical structures are shown in Table 1. The complete synthesis of one of the haptens ((+)METH P6) was previously reported (Byrnes-Blake et al., 2001, Int Immunopharmacol 1:329-338). Synthesis of an 8 carbon molecule spacer hapten was also attempted, but synthesis of this molecule proved more difficult than expected, so it was postponed. The chemical names and abbreviations of the five haptens are:

(S)-(+)-4-(3-carboxypropyl)methamphetamine, (+)METH P4

(S)-(+)-4-(5-carboxypentyl)methamphetamine, (+)METH P6

(S)-(+)-4-(5-carboxypentyloxy)methamphetamine, (+)METH P06

(S)-(+)-3-(5-carboxypentyloxy)methamphetamine, (+)METH MO6

(S)-(+)-3-(9-carboxynonyloxy)methamphetamine, (+)METH MO10

Each hapten was initially covalently bound to at least 2-3 different protein antigens and used for immunization of mice to test for anti-METH IgG response. The individual mouse and hapten-protein antigen combination that yielded the highest anti-(+)METH IgG titers was chosen for production of monoclonal antibodies (see details below). The following is a list of the hapten-protein conjugates that produced the mAb listed in table 1: (+)METH P4 and (+)METH P6 conjugated to bovine serum albumin; (+)METH PO6 and (+)METH MO6 conjugated to Imject Supercarrier Immune Modulator (catonized BSA (cBSA), Pierce Biotech, Rockford, Ill.); (+)METH MO10 conjugated to ovalbumin (OVA).

All chemical reactions for covalent binding of the haptens to protein antigens followed the same general procedure. The haptens were first solubilized in either 0.1 M 2-[N-morpholino]ethanesulfonic acid buffer (pH 4.5) or dimethylformamide and then adjusted to pH 4.5 with HCl. All haptens were coupled to their respective protein antigens by a carbodiimide reaction using the cross-linker 1-ethyl-3-[3-dimethylaminopropyl]carbodiimide hydrochloride (Pierce Biotech). This chemical synthesis forms a peptide bond between the carboxyl group of the hapten linker arm and free amino groups of lysine side chains in the respective proteins. The reactions were conducted with continuous stirring under dark conditions at room temperature for 18 hrs. At the end of the reaction, all antigens were purified as described by Byrnes-Blake et al. (2003, Eur J Pharmacol 461:119-128). This purification involved dialysis against distilled water, phosphate-buffered saline (pH 7.4), and a final purification of the soluble fraction on a gel filtration column in phosphate-buffered saline (pH 7.4). Purified antigens were stored at −20° C. until needed.

Immunization, Screening, and Hybridoma Generation.

Female BALB/c mice (Charles River Laboratories, Wilmington, Mass.) were used for all immunizations. For production of the (+)METH P6 mAb, mice were immunized subcutaneously in the hindquarters with 100 μg of the (+)METH P6 antigen emulsified 1:1 (v/v) in TiterMax adjuvant (CytRx Corporation, Norcross, Ga.) and boosted monthly with 50 μg of the antigen until a favorable titer was reached. For all other antigen immunizations, the mice were initially immunized in the hindquarters subcutaneously with 20-100 μg of antigen emulsified in Freund's complete adjuvant. The initial immunization was followed by a boost with 20-50 μg of antigen emulsified in Freund's incomplete adjuvant three weeks later followed by three boosts at six week intervals, until a favorable titer level was reached. Serum samples were taken via tail bleed periodically to measure anti-(+)METH IgG. Titers were measured by ELISA (enzyme-linked immunosorbant assay) using 96-well microtiter plates coated with the original hapten conjugated to a different protein. For example, if the original antigen was (+)METH-MO6-cBSA, (+)METH-MO6 conjugated to thyroglobulin was used to avoid selecting carrier protein-reactive antibodies. The screening for anti-(+) METH IgG response was conducted by a [$^3$H]-(+)METH radioimmunoassay (RIA), using (+)METH and (+)AMP as the inhibitors. After sufficient anti-(+)METH IgG titers were achieved, conventional hybridoma technology was utilized as described previously (Valentine et al., 1994, J Pharmacol Exp Ther 269:1079-1085). The hybridoma fusion partner for mouse B cells was cell line P3X63Ag8.653 (American Type Culture Collection, Manassas, Va.). IgG isotype and light chain identity was determined with a mouse antibody isotyping kit (Boehringer Mannheim, Indianapolis, Ind.).

Production and Purification.

Monoclonal antibodies were produced in either a Cell-Pharm System 2500 hollow fiber bioreactor (Valentine et al., 1996, J Pharmacol Exp Ther 278:709-716); Unisyn Technologies, Inc., Hopkinton, Mass.) or in a Biostat B 10 liter bioreactor (Sartorius Corp, Edgewood, N.Y.). All antibodies were harvested and stored at −80° C. until purification. Monoclonal Ab were purified either by affinity chromatography using Protein-G Sepharose (Amersham Biosciences, Piscataway, N.J.), or ion exchange chromatography using SP Sepharose (Amersham Biosciences, Piscataway, N.J.) as described in Hardin et al. (1998, J Pharmacol Exp Ther 285: 1113-1122), or a combination of the two methods. Following purification, all antibodies were concentrated and buffer exchanged into 15 mM sodium phosphate containing 150 mM sodium chloride (pH 6.5-7.5) as described in McMillan et al. (2002, Behav Pharmacol 13:465-473).

Determination of Immunochemical Specificity.

The cross-reactivity profiles of each mAb for methamphetamine, and structurally related and unrelated compounds, was determined by RIA in a manner similar to that described by Owens et al. (1988, J Pharmacol Exp Ther 246:472-478). An IC50 value for inhibition of [$^3$H]-(+)METH (and [$^3$H]-(+)AMP for the mAb generated against the (+)METH MO10 hapten) was determined for each ligand after fitting a sigmoidal curve to the data points. $K_D$ values for mAb were determined by the method of Akera and Cheng (1977, Biochim Biophys Acta 470:412-423).

Results.

For these studies, the hapten spacers were progressively lengthened from 4-10 atoms to increase the potential for greater interaction of the METH-like structures with the antibody binding site and to increase the flexibility of the spacer. It was hypothesized that a progressive lengthening of the spacer arm would lead to increases in affinity due to improved access to the entire METH-like structure; and the different immobilized conformations would elicit antibodies having different conformational selectivity for (+)METH-like compounds.

The haptens were conjugated to the terminal amino groups of lysines in bovine serum albumin or ovalbumin by carbodiimide chemistry, which forms a peptide bond with the available carboxylic acid on the hapten. There were 59 lysines in bovine serum albumin, 20 in each of the four subunits of ovalbumin and even more conjugation sites were available on cationized bovine serum albumin (i.e., Imject Supercarrier Immune Modulator). However not all of the lysines or conjugation sites were available at the surface of the protein for coupling to the haptens. Preliminary optimization experiments showed that a ratio of hapten to protein of 30:1 to 90:1 yielded the best incorporation rates for the syntheses. While the hapten incorporation rate for the antigens could not be precisely determined, initial mass spectrophotometry studies indicated that an average of 4 haptens were conjugated to each molecule of protein.

Because the primary goal was to select for high-affinity mAb, the antigen dose was kept relatively low (e.g., 10-20 μg). While immunization with higher hapten-antigen doses (e.g., 50-100 μg) sometimes led to higher titers, the affinity for (+)METH was often too low. Thus a minimum dose of antigen was typically used. This strategy routinely led to immunological response in only 40-70% of animals. In more recent studies, it was discovered that a primary reason for <100% immunological response was the low incorporation rate of the hapten on protein antigens, which in part was overcome by judicious use of Freund's complete and incomplete adjuvants to boost and sustain immunological response.

Each mouse serum from each group of immunizations was routinely screened (typically 6-10 mice) after each boost to determine the maturity of the immune response and the relative immunochemical characteristics of the polyclonal serum (titer, affinity and specificity). For this, a [$^3$H]-(+)METH RIA was used. The screening assay always involved inhibitions of [$^3$H](+)METH binding with increasing doses of (+)METH and (+)AMP to determine the relative affinities for each ligand. The final choice of a specific mouse for use in generating hybridomas was based primarily on the animal with the highest titer and affinity for (+)METH. From this process of screening immune serum, 3-10 unique monoclonal antibodies were generally found from each fusion. Most importantly, a polyclonal antiserum that was positive for (+)AMP was not discovered until the MO10 hapten was used.

For producing the hybridomas, mice were chosen that had been immunized with Freund's complete adjuvant and boosted with Freund's incomplete adjuvant. The one exception was the immunizations with (+)METH P6, which used Titermax as the adjuvant. In preliminary optimization experiments, immunizations with alum precipitated antigens, Titermax adjuvant and Ribi's adjuvant were tried on several occasions. While these adjuvants generally produced high titers, it was found that the highest affinity antibodies were generated with Freund's adjuvants.

Example 2

MAP Cross Reactivity Studies

After screening over 25,000 potential hybridoma cell lines for mAb production, five mAb with the most favorable immunochemical characteristics were extensively studied for molecular properties and preclinical efficacy (see Table 1). The rest of the hybridoma cell lines were stored frozen in case of future need. The selection of a mAb for more extensive in vitro and in vivo testing was based on the desire to have a range of affinities, a range of drug specificities, and a high level of mAb production from the parent hybridoma cell line. This final criterion was needed to increase the feasibility of large scale mAb production for in vivo testing. In most cases there was one or more similar affinity or specificity mAb that were produced from the same fusion. For instance, the separate fusions that produced mAb6H4 and mAb4G9 (see Table 1) also produced mAb with virtually the same affinity and specificity, but slightly different amino acid sequences. These two particular antibodies were chosen because the parent hybridoma cell line produced significantly more mAb.

TABLE 1

Chemical Structure of Haptens, the Resulting mAb, and $K_D$ Values for Key Drugs

| Hapten Structure | Hapten Name | mAb Name (Isotype and light chain) | Key Psychostimulants | | |
| --- | --- | --- | --- | --- | --- |
| | | | (+)METH $K_D$ (nM) | (+)AMP $K_D$ (nM) | (+)MDMA $K_D$ (nM) |
| 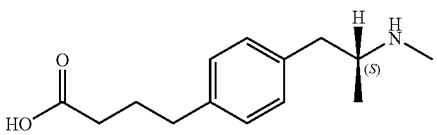 | (+)METH P4 | mAb6H8 (IgG$_1$ κ) | 250 | 41,000 | 106 |

TABLE 1-continued

Chemical Structure of Haptens, the Resulting mAb, and $K_D$ Values for Key Drugs

| Hapten Structure | Hapten Name | mAb Name (Isotype and light chain) | (+)METH $K_D$ (nM) | (+)AMP $K_D$ (nM) | (+)MDMA $K_D$ (nM) |
|---|---|---|---|---|---|
| | (+)METH P6 | mAb6H4 (IgG$_1$ κ) | 11 | 4000 | 4 |
| | (+)METH PO6 | mAb6H7 (IgG$_{2b}$ κ) | 95 | 47,000 | 87 |
| | (+)METH MO6 | mAb9B11 (IgG$_1$ λ) | 41 | 5000 | 123 |
| | (+)METH MO10 | mAb4G9 (IgG$_{2b}$ κ) | 34 | 120 (51 nM with [$^3$H]-(+)AMP) | 140 |

Results.

RIA was used to determine the relative affinity and cross-reactivity profile of each mAb (Tables 1 and 2). Only one of five haptens generated mAbs with the desired therapeutic potential. Immunization with the MO10 hapten resulted in production of mAb (mAb4G9) with high-affinity binding to (+)METH, (+)AMP, and (+)MDMA; little or no cross-reactivity with (−)METH-like isomers; and no significant cross-reactivity with endogenous compounds or structurally similar common medications (Tables 1 and 2). No other hapten/linker location yielded an antibody with high affinity for all three drugs of abuse.

TABLE 2

Characterization of the binding specificities of three important prototype anti-METH/MDMA or anti-METH/MDMA/AMP mAb.

| | Antibody Specificity (Relative Potency to METH)[a] | | |
|---|---|---|---|
| Drug | mAb6H4 (11 nM)[b] | mAb6H8 (250 nM)[b] | mAb4G9 (34 nM)[b] |
| (+)METH | 1.00 | 1.00 | 1.00 |
| (+)AMP | 0.001 | 0.023 | 0.34 |
| (+)MDMA | 1.25 | 3.40 | 0.29 |
| (−)METH | 0.030 | 0.011 | 0.102 |
| (−)AMP | <0.001 | 0.003 | 0.063 |
| (−)MDMA | 0.007 | 0.018 | 0.011 |
| (+)MDA | 0.001 | 0.024 | 0.090 |
| (−)MDA | <0.001 | <0.001 | 0.002 |
| 4-OH-METH | 0.588 | 0.294 | 0.106 |
| (+)pseudoephedrine | <0.001 | 0.018 | 0.004 |
| (+)norpseudoephedrine | <0.001 | <0.001 | <0.001 |
| l-phenylphrine | 0.001 | <0.001 | <0.001 |
| (+)ephedrine | <0.001 | <0.001 | <0.001 |
| (+)phenylpropanolamine | <0.001 | <0.001 | <0.001 |
| β-phenylethylamine | <0.001 | <0.001 | 0.001 |
| tyramine | <0.001 | <0.001 | <0.001 |
| dopamine | <0.001 | <0.001 | <0.001 |
| norepinepherine | <0.001 | <0.001 | <0.001 |
| serotonin | <0.001 | <0.001 | <0.001 |
| epinephrine | <0.001 | <0.001 | <0.001 |

[a]Relative potency to METH = (RIA IC50 value for METH/RIA IC50 value for test ligand). See Table 1 for the structures of the haptens used to generate these antibodies.
[b]IC50 value for METH binding from Table 1.

Since mAb4G9 was the only mAb to significantly cross-react with (+)AMP (Tables 1 and 2), its affinity for (+)AMP was examined in more detail. For this, a RIA analysis was conducted using [$^3$H]-(+)AMP (in addition to a RIA with [$^3$H]-(+)METH) and AMP as the inhibitor. These data showed the actual affinity for AMP was 51 nM (Table 1), demonstrating that this mAb has virtually the same $K_D$ value for AMP and METH. [$^3$H]-(+)MDMA was not available for determining a more accurate $K_D$ value for (+)MDMA binding, but it seems likely that the true $K_D$ value would be significantly lower than the value indicated by MDMA inhibition of [$^3$H]-(+)METH binding in the RIA.

Attaching the linker of the hapten distal to the chiral center of the molecule yielded a refined specificity for (+)-isomers (Table 2). The relatively short length of spacer arms of haptens (+)METH P4 and (+)METH P6 (4- and 6-carbon linkers, respectively), coupled with attachments at the para-carbon of the (+)METH phenyl ring (Table 1), hindered the flexibility of haptens. This likely forced the immune system to recognize the presence of the methyl group on the nitrogen molecule of (+)METH and (+)MDMA and its absence in (+)AMP. Thus, mAb affinity was high for (+)METH and (+)MDMA, but low for (+)AMP. The hapten (+)METH PO6, like (+)METH P6, was designed with a linker attached to the para-carbon of the phenyl ring, but an oxygen was included to influence localized charge and solubility and mimic the presence of one of two oxygen atoms at the para and meta positions of the methylenedioxy group of (+)MDMA (Table 1). An oxygen attached to the phenyl ring structure was included in two other haptens, (+)METH MO6 and (+)METH MO10, but linkers were attached to the meta-carbon of the phenyl ring of (+)METH. This strategy was designed to present the oxygen of the (+)MDMA-like structure along the same spatial plane as the (+)METH molecule's chiral center. The longer (+)METH MO10 spacer was used to allow more flexibility in the hapten on the protein in hopes of discovering mAb(s) with broader recognition of (+)METH-like structures. These combined strategies resulted in the best balance of affinity and specificity.

From these studies, it was learned that 1) linkers located distal to the chiral center of this very small molecule favor generation of stereospecific antibodies, 2) a longer flexible linker arm like (+)METH MO10 favors generation of antibodies with broader selectivity for (+)METH-like compounds, and 3) spacers ≥6 atoms produce higher affinity mAbs. Importantly, discovery of mAb4G9 was not an isolated event, as other MO10-derived mAbs with similar specificities for (+)METH and (+)AMP have since been discovered.

Example 3

Antibody Sequence Analysis

To gain a better molecular understanding of how the primary amino acid sequence affected mAb affinity for (+)METH, related and unrelated sequence features in each mAb variable region was analyzed. Three of the mAb were IgG1 subclass and two were IgG2 (Table 1). Except for anti-METH/MDMA mAb9B11 (λ light chain), all of the mAb possessed a κ light chain.

cDNA Cloning and Sequencing of mAb.

For these studies, five prototype anti-METH mAb ranging in METH affinities from 11 to 250 nM were analyzed (Table 1). A single prototype mAb resulting from each of the haptens was chosen for detailed studies. The light chain (LC, singular and plural) cDNA of the mAb were cloned by RT-PCR using Superscript II reverse transcriptase (Invitrogen) with an exact reverse primer matching C-terminus of the light chain named MLEND1.Not (5'-GGG GCG GCC GCG CGT CTC AGG ACC TTT GTC TCT AAC-3') (SEQ ID NO:1). The light chains of mAb6H4, mAb6H8, and mAb6H7 were amplified in the forward direction with the degenerate primer ML2, and the light chain of mAb4G9 was amplified in the 5' direction with the degenerate primer ML4 (Coloma et al., 1992). The light chain of mAb9B11 was amplified in the forward direction with the primer sequence 5'-ATGGCCTGGA(T/C)TTCACTTATACTCTCTCTCCTGGCTCTC-3' (SEQ ID NO:2). The resulting cDNA was blunt-ligated into the Sma I site of the cloning vector pGEM-3Z.

The heavy chain cDNA of all IgG1 (from (+)METH P4, (+)METH P6 and (+)METH MO6) mAb were amplified using RT-PCR as described above with an exact reverse primer to the C-terminus of the heavy chain, named MHEND.NotI 5' GGG GCG GCC GCA GGG CTC CAA GGA CAC TGG GAT CAT TT 3' (SEQ ID NO:3), and a mixture of three degenerate primers based on the MHALT primers from Coloma et al. (1992, J Immunol Methods 152: 89-104). The primers were modified from the originally published sequence only by the substitution of a Nhe I restriction site for the original restriction site. The IgG2 mAb (from (+)METH PO6 and (+)METH MO10) were amplified with the reverse primer 5-CTCCCGGTCTCCGGGTAAATGA-3' (SEQ ID NO:4).

Figure 1A:
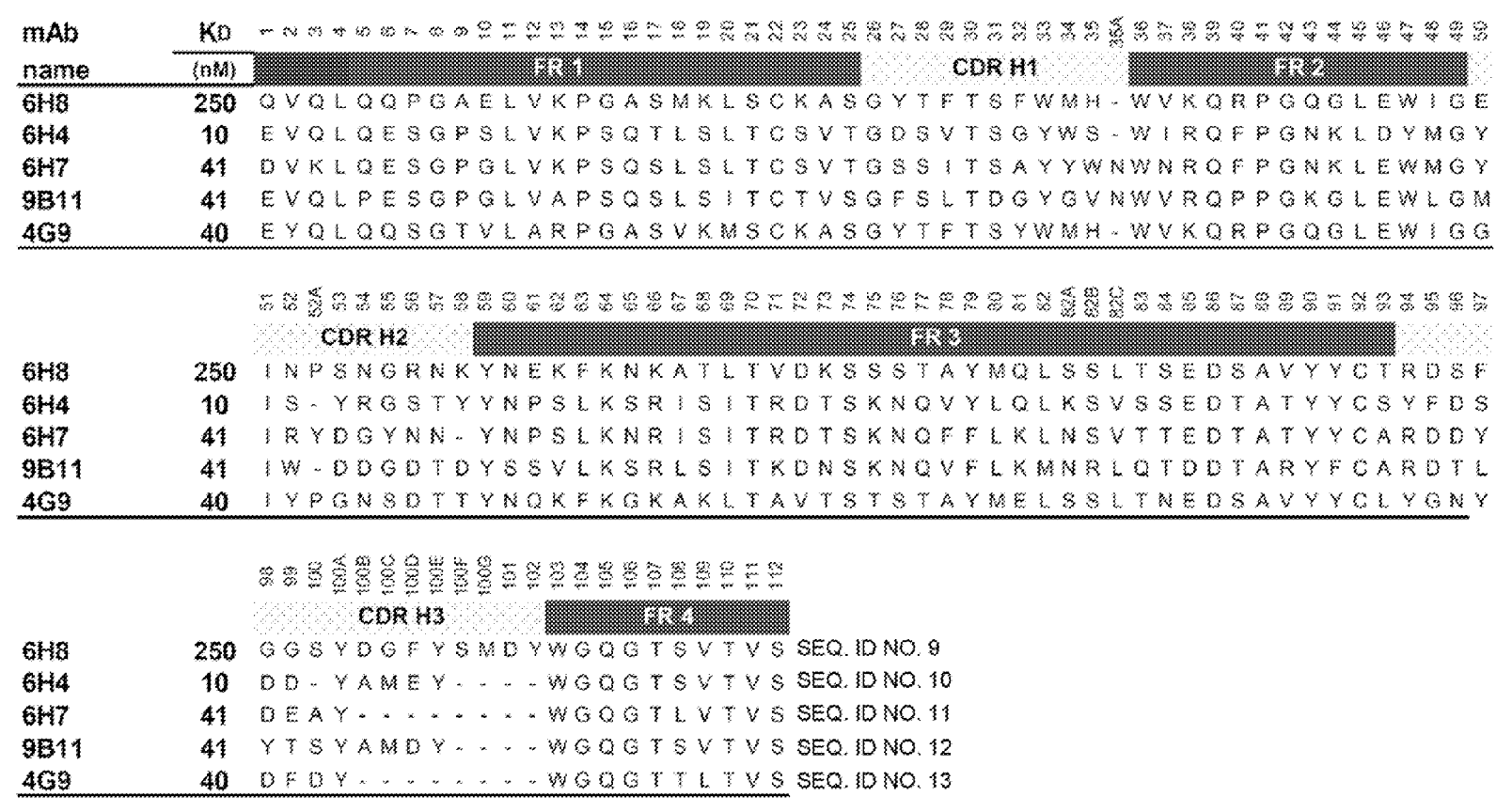

The forward sequence of the heavy chain of mAb6H8 was amplified with primer MHALT1 (Coloma et al., 1992, J Immunol Methods 152:89-104). The forward primers for mAb6H4, mAb6H7, mAb9B11, and mAb4G9 were designed from the results of N-terminal sequencing of the mature proteins (see FIGS. 1A and B for protein sequences). The primer sequences used were: 5'-GAGTGCAGCTTCAGGAGT-CAGGACCTAGC-3' (SEQ ID NO:5) for mAb6H4,5'-GAT-GTAAAACTTCAGGAGTCAGGACCTGGC-CTCGTGAAACCTTCTCAGTC-3' (SEQ ID NO:6) for mAb6H7,5'-GAGGTGCAGCTTCCGGAGTCAGGAC-CTAGC-3' (SEQ ID NO:7) for mAb9B11, and 5'-GAGTAC-CAGCTCCAGCAGTCTGGGAC-3' (SEQ ID NO:8) for mAb4G9. The cDNA was then blunt-ligated into the Sma I site of cloning vector pGEM-3Z. The resulting plasmids of all mAb cloning was transformed into *E. coli* strain DH5α and sequenced at University of Arkansas for Medical Sciences DNA Core Sequencing Facility.

All sequences were submitted to the GenBank database. The GenBank-assigned accession numbers of the light chains of mAb6H8, mAb6H4, mAb6H7, mAb9B11, and mAb4G9 are 774083, 786626, 877567, 881246, and 877579 respectively. The GenBank-assigned accession numbers of the heavy chains of mAb6H8, mAb6H4, mAb6H7, mAb9B11, and mAb4G9 are 774081, 774071, 881226, 877571, and 877573, respectively. The germ-line usage of the different mAb was determined by comparing the DNA sequences to those in the IMGT database using the web-based program V-QUEST tools (Internet address: http://imgt.cines.fr) and by visual examination of the sequences (Giudicelli et al., 2004, Nuc Acid Res 32:W435-440).

Results.

Figure 1B:
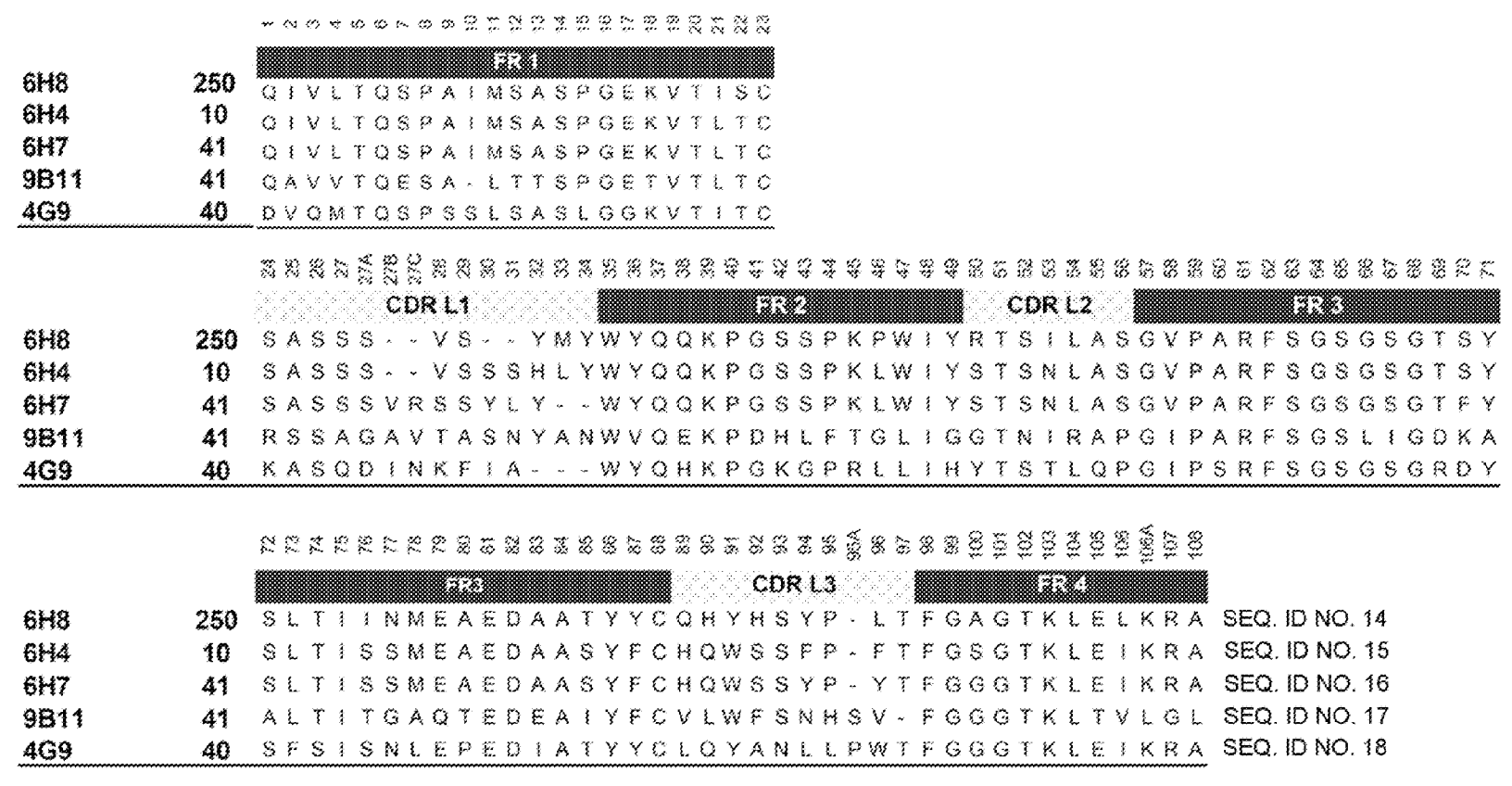

Alignments of the amino acid sequences of the variable region of the mAb is presented in FIG. 1. An analysis of complementary determining regions revealed a high degree of diversity in both composition and length. The first light chain CDRs (L1) varied in length from 10-14 residues, and with the exception of mAb4G9, possessed a large number of serine residues (FIG. 1B). The only conserved residue in CDR L1, or any of the light chain CDRs, was the serine at position L26. The L2 CDRs were 7 residues in length except for mAb6H7, which possessed only 5 amino acids. The L3 CDRs were all 9 residues in length except mAb4G9 which had 10 residues. The CDRs of the heavy chain regions (FIG. 1A) exhibited similar lengths in CDRs H1 and H2, but little homology. CDR H1 had a conserved threonine at position H30 and either a tryptophan or tyrosine at position H33. CDRH3 differed in length from 8-16 residues. Although not immediately apparent from the alignment, all H3 regions possessed two tyrosine residues spaced five residues apart, with the second tyrosine before the tryptophan at H103.

While comparisons of CDR sequences are important, differences in CDR can be attributed to differences in germ-line sequences of particular V-region genes, and to somatic mutation within the CDRs of these V-region genes. To better understand the relative importance of the germ-line and somatic mutations, the sequenced genes were analyzed using the IMGT database (Giudicelli et al., 2004, Nuc Acid Res 32:W435-440). The analysis showed that each antibody was unique and not clonal. That is, rather than coming from one germ-line gene arrangement early in B cell development, they resulted from unique V(D)J recombination events. These unique germ-line gene rearrangements then underwent somatic DNA mutations, that were often silent, but some resulted in amino acid changes that differed from the original germ-line gene. Thus, no clear pattern of response was found.

This sequence analysis elucidated unique sequence differences in the antibody CDRs. A common feature was a conserved proline at position 95 or 95a of all CDR L3 regions, except for mAb9B11 (FIG. 1B), which had a serine residue. Because of their ability to form "hinges," proline residues often lend flexibility in main chain protein sequences. This proline/serine was immediately followed by either a hydrophobic amino acid (i.e. leucine or valine as in mAb6H4 and mAb9B11, respectively) or an aromatic residue. It is possible that these residues could be important for interaction with the phenyl ring of (+)METH-like compounds via hydrophobic or pi-pi interactions, and the preceding proline could lend flexibility to adapt to different conformations.

Example 4

Molecular Modeling and Docking

Based on the results of the primary sequence alignment, three mAb (mAb6H4, mAb6H8 and mAb4G9) were chosen for structural modeling. Each CDR variable region was assigned and given a canonical classification (Al-Lazikani et al., 1997, J Mol Biol 273:927-948), except for the H3 CDRs, which do not possess canonical classes.

IgG Variable Region Structural Modeling and Analysis.

Molecular modeling of the three dimensional structure of the variable regions of three of the mAb was performed using the WAM antibody modeling algorithm (Whitelegg and Rees, 2000, Protein Eng 13:819-824). mAb6H4, mAb6H8, and mAb4G9 were chosen for more detailed analysis because they exhibited the full range of affinities for (+)METH and a broad range of ligand specificities for other important METH-like drugs. The primary amino acid sequences of the variable regions of the HC and LC were first submitted to the WAM antibody modeling site for alignment. The program aligned the sequences against known sequences in the database and searched for canonical classes of complementary determining regions (CDR). Based on these classifications; the program assigned a 3-dimensional structure to the framework and CDR regions by fitting the main chain to that of the closest known structures.

Ligand Docking.

For docking simulation, the FlexX (Tripos) program was used. First, a deep pocket was identified at the interface of the CDR regions from surface modeling and electrostatic calculations in Pymol (Delano Scientific, San Carlos, Calif.) and Sybyl (Tripos). To define this region as a putative active site, residues within an area 6 Å around F L94 (for mAb6H4) or Y L94 (for mAb4G9) were selected. The METH ligand was assigned formal charges by Sybyl and the molecule was allowed partial flexibility. The program was set to find the 30 best docking conformations and return these in a consensus scoring table.

Results.

The three-dimensional models exhibited classical antibody β-sheet fold conformation (FIG. 2). In general, all models showed conformity with geometrical constraints throughout the structures. The analysis indicated that less than 2% of residues had main chain ψ and φ angles in outlier regions. All three models appeared to conform reasonably well to known protein structural features and constraints, and they presented an appropriate foundation to conduct base docking analysis.

Figure 3:
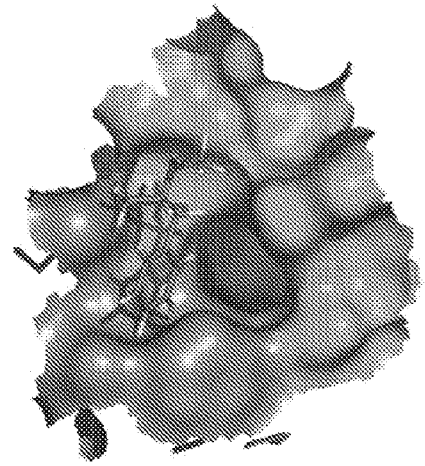
FIG. 3 illustrates modeled structures of the anti-(+)METH mAb variable chains. In this model, METH (magenta) has been computationally docked into a pocket at the interface of the VH and VL chains with FlexX software. Left panels: Surface rendering of deep pocket in mAb6H4 and mAb4G9. The VL chain domain is on the left side in blue and the VH chain domain is on the right in green. Right panels: Stick representation of mAb6H4 and mAb4G9. Only side chains within 8 angstroms of the METH molecule are shown for clarity. The view is oriented in a "top view" with the same color scheme as in left panel. The side chains are labeled and numbered in the Kabat scheme as in FIG. 1.
Figure 3:
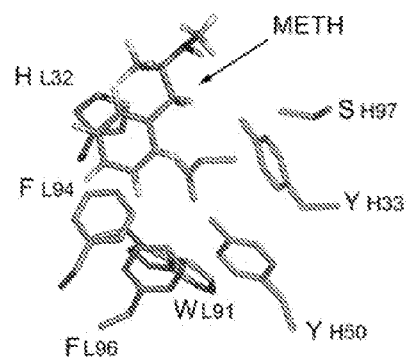
Figure 3:
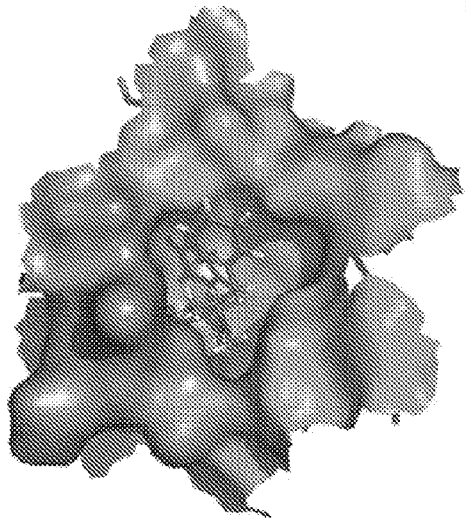
Figure 3:
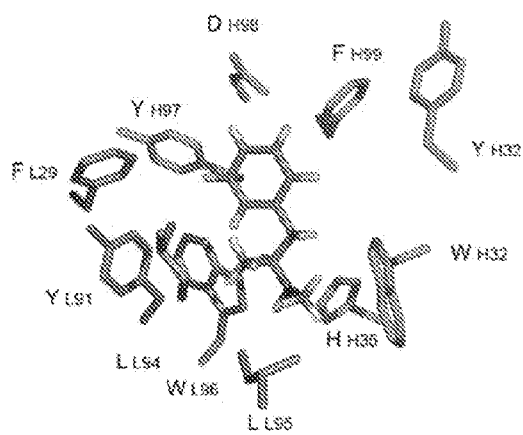

All CDRs fell within canonical classes except L3 of mAb4G9 and the H3 CDRs, which do not have canonical classes. The CDR H3 regions of all three antibodies were predicted to form a kinked or "hairpin," rather than extended conformation. Comparison of the models revealed conserved structural elements and some potentially important differences in the root mean square deviations (RMSD) of the CDR loop configurations (FIG. 3). The loop structure of mAb6H4 was arbitrarily chosen as a reference point to compare the differences from the other two antibodies, because it had the highest affinity for (+)METH. The L2 CDRs of all three antibodies occupied nearly the same spatial positions. The L3 regions of mAb6H4 and mAb6H8 were very similar, even though they differed in affinity for (+)METH by about 25-fold.

Based on the modeling results, docking simulation was performed with mAb6H4 and mAb4G9. According to the models (FIG. 3), a deep pocket was formed by the interaction of CDR loops H1, H2, L1 and L3 for both antibodies, with a wider pocket formed in the binding region of mAb4G9 due to a shorter $H_3$CDR. A theoretical docking of (+)METH was created into these mAb pockets and identified residues within 8 angstroms of the ligand as possible sites for ligand-mAb interaction (FIG. 3). The results of this FlexX-based docking indicated that the METH molecule was generally oriented with the hydrophobic phenyl group toward the interior of the pocket. In mAb6H4 and mAb4G9, the charged nitrogen of METH was in close proximity to a histidine at position L32 and H35 respectively.

Based on the molecular modeling analyses, the interface between (+)METH and the mAb was relatively small, (the surface area of (+)METH is 174 Å 2) with small shifts in protein conformation producing large changes in binding. As can be seen in FIG. 2, the most striking deviations appeared in the H3 CDR region, with over 6 Å and 7 Å RMSD in mAb6H8 and mAb4G9, respectively. The diversity in the positions of the CDR suggests that each of these antibodies exhibited a binding paradigm to (+)METH-like drugs that was somewhat independent of loop configuration. The surface rendering of the models exposed a deep pocket at the CDR interface of mAb6H4. This pocket appeared to be approximately the size of (+)METH and would likely accommodate docking of the ligand. By contrast, the potential binding pocket of mAb4G9 was wider and shallower. It is hypothesized that the longer linker arm of (+)METH MO10 combined with the changed dihedral angle of an oxygen at the meta position of the phenyl ring contributed to the formation of a larger pocket. Analysis indicated that only five of the six CDR loops, might be directly involved in binding of (+)METH-like drugs, with L2 showing little contact. The (+)METH docking simulation with FlexX indicated that the potential binding pockets were dominated by aromatic residues with some capable of making hydrogen bonds (i.e., histidine and tyrosine).

Example 5

Mercapto-Haptens

The linking group on a hapten was modified to determine whether the number of linkages per carrier could be increased. It was found that a hapten containing a sulfhydryl group rather than a carboxylic acid group had increased covalent coupling to a maleimide-activated carrier protein. The coupling efficiency was also highly reproducible and required low starting ratios of hapten to protein. This coupling strategy offers significant advantages over carbodiimide coupling while other critical features of the (+)METH-MO10 hapten are maintained. Thus, this new hapten (designated (+)METH-SH-MO10 for the sulfhydryl group at the end of the spacer arm) offers a significant improvement over carbodiimide coupling, which was often inefficient with poor chemical reaction reproducibility. As described above, carbodiimide coupling typically resulted in only about five (+)METH-like haptens per albumin molecule. This ratio was less than ideal because little to no immunological response was initiated when too few haptens (≤4) were incorporated on the carrier molecule, whereas the quality and quantity of immune response was greatly improved with greater hapten epitope densities (i.e., 8-12 haptens per albumin molecule (Owens, et al., 1988, J Pharmacol Exp Ther 246:472-478).

Although the relationship between incorporation rate and immune response is not known for (+)METH-like antigens, it is a critical factor in immune response optimization. Achieving high, reproducible incorporation rates with carboxylic acid haptens has always been a challenge, as has been, until recently, accurate measurement of hapten incorporation rates. The new mercapto-hapten will help alleviate the challenge of low incorporation rates.

Determination of Incorporation Rates from Conjugation Reactions.

Figure 4A:
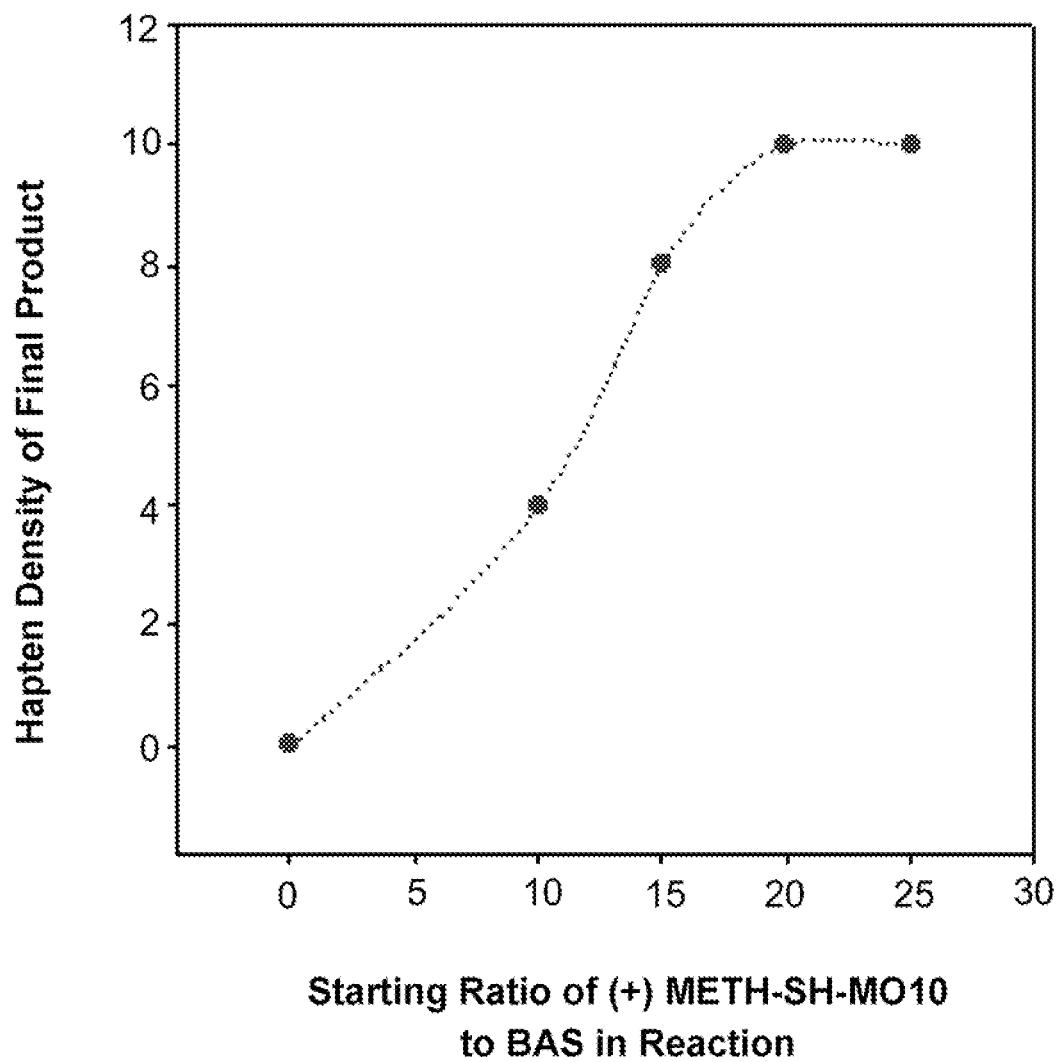
FIG. 4 illustrates coupling of mercapto-haptens to maleimide-activated carrier protein. (A) The mercapto-hapten, (+)METH-SH-MO10, is conjugated to carrier, BSA, in a linear fashion to a maximum of 10 haptens per BSA. Increasing amounts of hapten, (+)METH-SH-MO10 were added to solutions containing a constant amount of carrier, activated BSA. Epitope density, the number of hapten molecules attached to a single carrier protein, was analyzed by MALDI-TOF MS and plotted opposite the corresponding ratio in the conjugation reaction. (B) MALDI-TOF MS analysis of maleimide-activated ovalbumin (top panel), and the newly generated (+)METH-SH-MO10 hapten coupled to maleimide-activated ovalbumin (lower panel). (C) The mercapto-hapten, (+)METH-SH-MO10, conjugated to ovalbumin, generates monoclonal antibodies specific for (+)METH and (+)MDMA. Data from a representative mAb is shown. Radiolabeled (+)METH incubated with mAb is inhibited from binding using increasing amounts of unlabeled drug, i.e. (+)METH, (+)AMP, or (+)MDMA. Inhibition of binding to mAb is quantified and plotted opposite the amount of cold drug used as inhibitor. At the 50% inhibition value, the unlabeled drug concentration approximates the affinity of the mAb for that drug.

In experiments to determine the efficiency of coupling the new mercapto-haptens, increasing molar concentrations of the prototype (+)METH-SH-MO10 hapten were added to a fixed molar concentration of maleimide-activated bovine serum albumin purchased commercially (Pierce Chemical). The synthesis was conducted according to the manufacturer's instructions. The starting molar ratio of hapten to maleimide-activated bovine serum albumin was 0:1 (no hapten added), 10:1, 15:1, 20:1 and 25:1. After the reaction was complete MALDI TOF MS analysis of the samples showed the actual molar ratio of hapten to bovine serum albumin carrier protein was about 0:1 (no hapten added), 4:1, 8:1, 10:1 and 10:1, respectively. This indicated that the synthetic reaction was extremely efficient with approximately 1 mole of hapten being incorporating for each 2 moles of hapten added to the reaction. However, there appeared to be a maximum of 10 available maleimide-activated sites on the bovine serum albumin (see FIG. 4A).

In previous experiments with a carboxy-hapten ((+)METH MO10) using a 30:1 starting ratio of hapten to bovine serum albumin and a carbodiimide reaction, a maximum of 5:1 haptens per bovine serum albumin molecule was obtained. These data suggest the mercapto-haptens are more efficiently coupled to their protein carriers, thereby offering significantly less costly synthesis. In addition a much greater number of haptens can be incorporated to each protein (10:1 for the mercapto-hapten versus 5:1 for the carboxy-hapten).

Figure 4B:
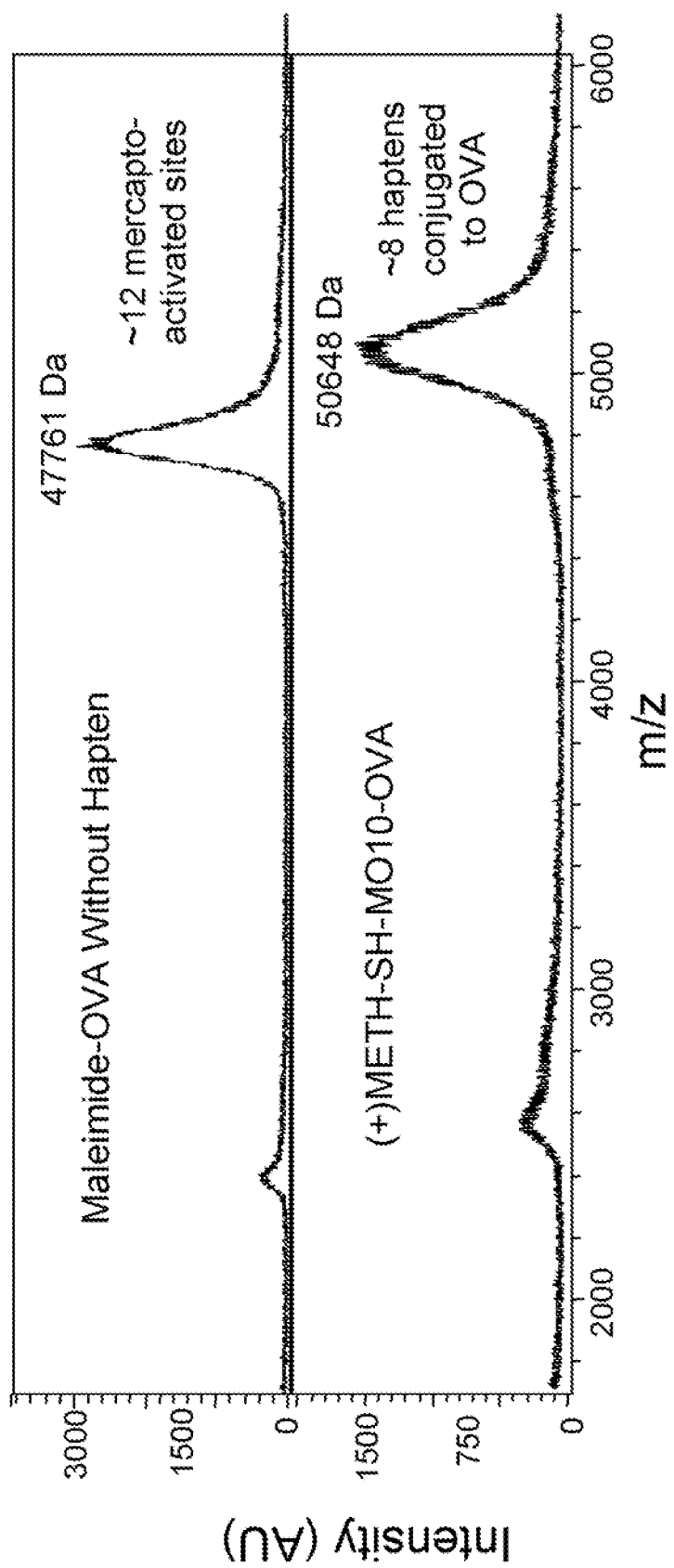

Similarly, mass spectrometric analysis of maleimide-activated ovalbumin with or without (+)METH-SH-MO10 haptens revealed that when 12 pre-activated maleimide sites were available on ovalbumin (upper panel, FIG. 4B), 8 (+)METH-SH-MO10 haptens were incorporated per ovalbumin molecule (lower panel, FIG. 4B). This was a 60% increase in the efficiency of coupling compared to the carbodiimide coupling of MO10 to ovalbumin (5 MO10 haptens per ovalbumin). Thus, new (+)METH mercapto-haptens, like (+)METH-SH-MO10, should result in higher epitope densities on the carrier protein and significantly increase titers and the probability of generating high-affinity polyclonal antiserum.

Immunization, Screening, and Hybridoma Generation.

Figure 4C:
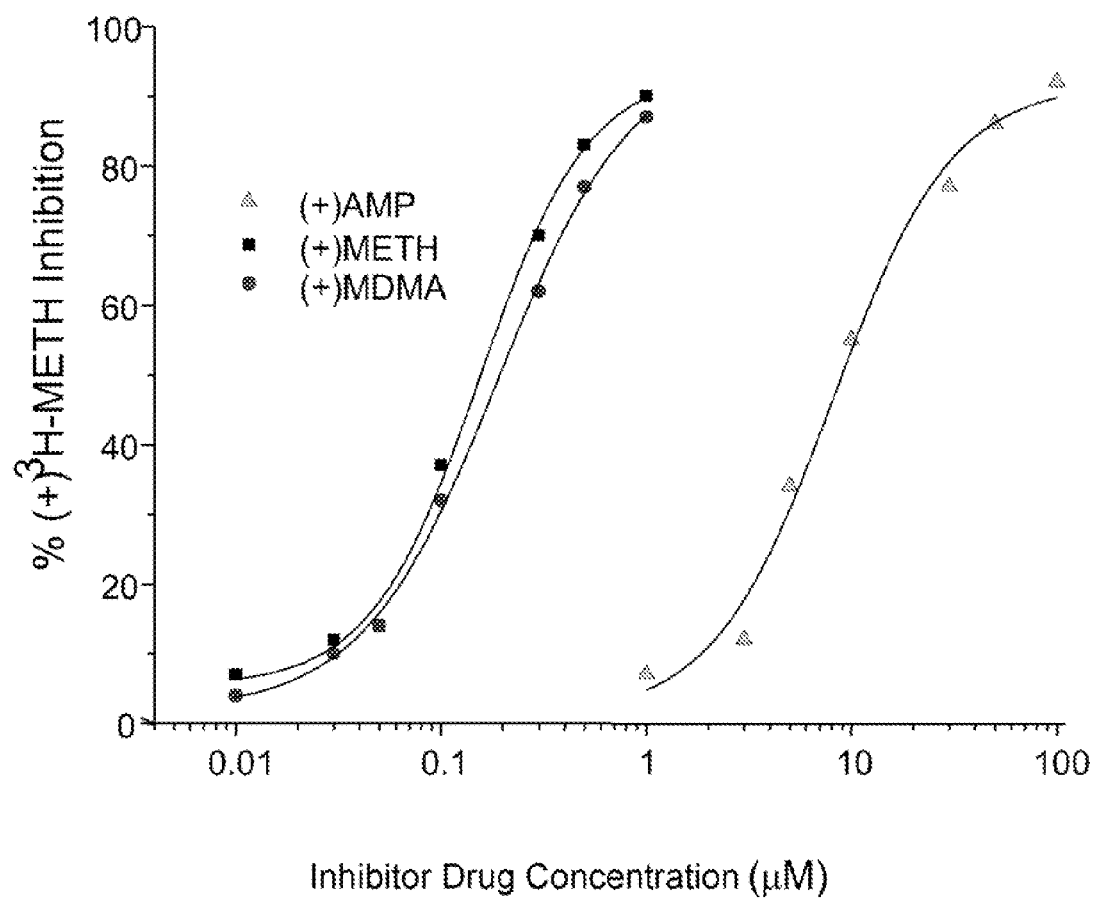

Female BALB/c mice (Charles River Laboratories, Wilmington, Mass.) were used for all immunizations. For production of the (+)METH-SH-MO10 mAb, mice were immunized subcutaneously in the hindquarters with 20 µg of the (+)METH-SH-MO10 antigen emulsified 1:1 (v/v) in Freund's complete adjuvant (FCA), (EMD Chemicals, Gibbstown, N.J.). The initial immunization was followed by a boost with 20 µg of antigen emulsified in Freund's complete adjuvant three weeks later followed by two boosts at three week intervals, until a favorable titer level was reached. Serum samples were taken via tail bleed periodically to measure anti-(+)METH IgG. Titers were measured by ELISA (enzyme-linked immunosorbant assay) using 96-well microtiter plates coated with the original hapten conjugated to a different protein. For example, if the original antigen was (+)METH-SH-MO10-Ovalbumin (OVA), (+)METH-MO10 conjugated to thyroglobulin was used to avoid selecting carrier protein-reactive antibodies. The screening for anti-(+)METH IgG response was conducted by a [$^3$H]-(+)METH radioimmunoassay (RIA), using (+)METH, (+)MDMA and (+)AMP as the inhibitors. After sufficient anti-(+)METH IgG titers were achieved, conventional hybridoma technology was utilized as described previously (Valentine et al., 1994, J Pharmacol Exp Ther 269:1079-1085). The hybridoma fusion partner for mouse B cells was cell line P3X63Ag8.653 (American Type Culture Collection, Manassas, Va.). IgG isotype and light chain identity was determined with a mouse antibody isotyping kit (Boehringer Mannheim, Indianapolis, Ind.). Crossreactivity data from a representative mAb is shown in FIG. 4C.

Example 6

Concurrent (+)METH Use and Immune Response

Immunization with (+)METH P6-KLH conjugate was examined in more detail to determine if active immunization would result in anti-(+)METH antibodies and if chronic (+)METH use would affect production of anti-(+)METH antibodies. These questions are important because generation of an antibody response is dependent on specific immune receptor recognition of (+)METH-conjugates, and patient use of (+)METH during immunization could block an immune response.

For these studies, male Sprague-Dawley rats were immunized with KLH (control group) or the (+)METH P6 hapten-KLH conjugate (see Table 1 for hapten structure). (+)METH P6-KLH animals were further divided into two immunized groups—one with no subsequent administration of (+)METH, the other repeatedly challenged with (+)METH (3 mg/kg ip; twice a week). Analysis of relative antibody affinities was accomplished in an ELISA by adding increasing concentrations of (+)METH to mouse immune serum in microtiter plate wells coated with a (+)METH P6-ovalbumin conjugate.

Figure 5:
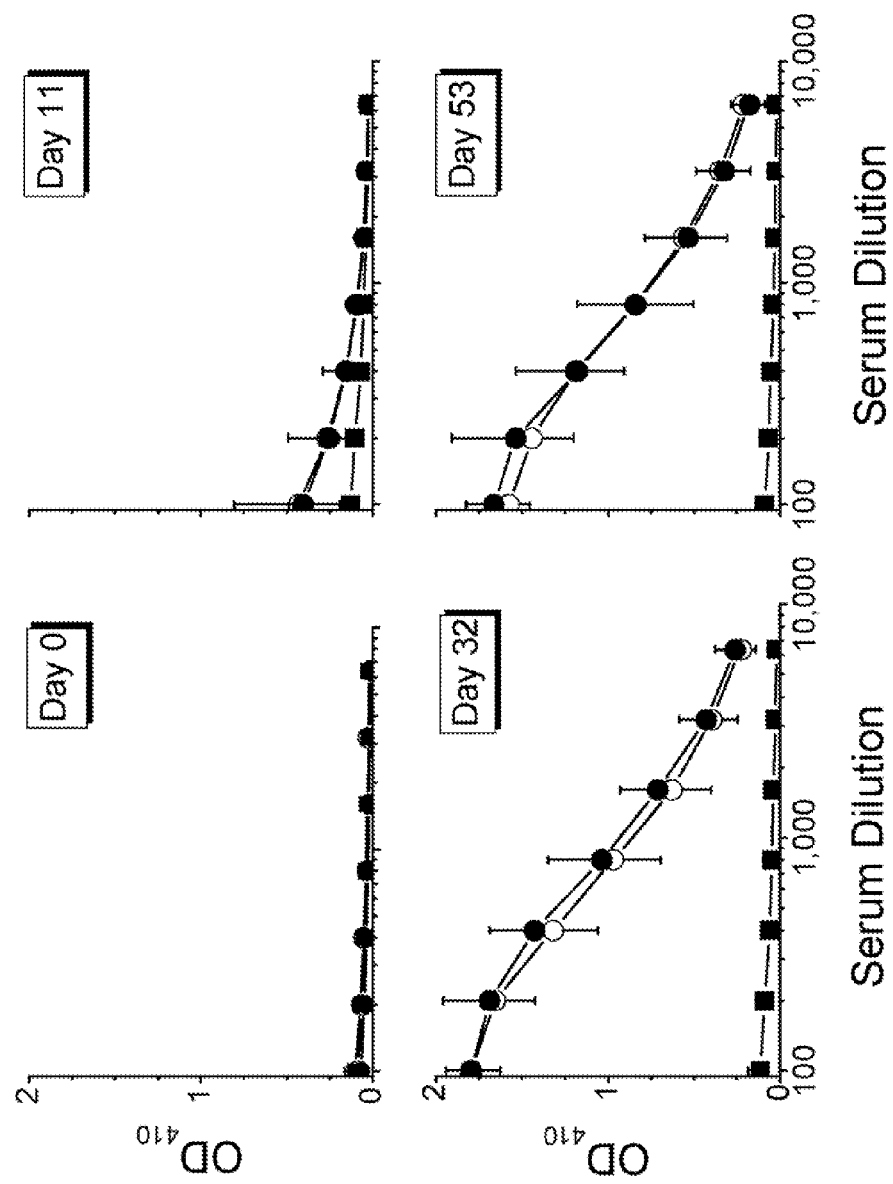
FIG. 5 illustrates immune responses to (+)METH P6 hapten-KLH conjugate. Comparison of rat anti-(+)METH antibody titers by ELISA. KLH immunized animals (■); (+)METH P6-KLH immunized animals (●); and (+)METH P6-KLH immunized animals with repeated 3 mg/kg, ip (+)METH challenges (○).
Figure 6:
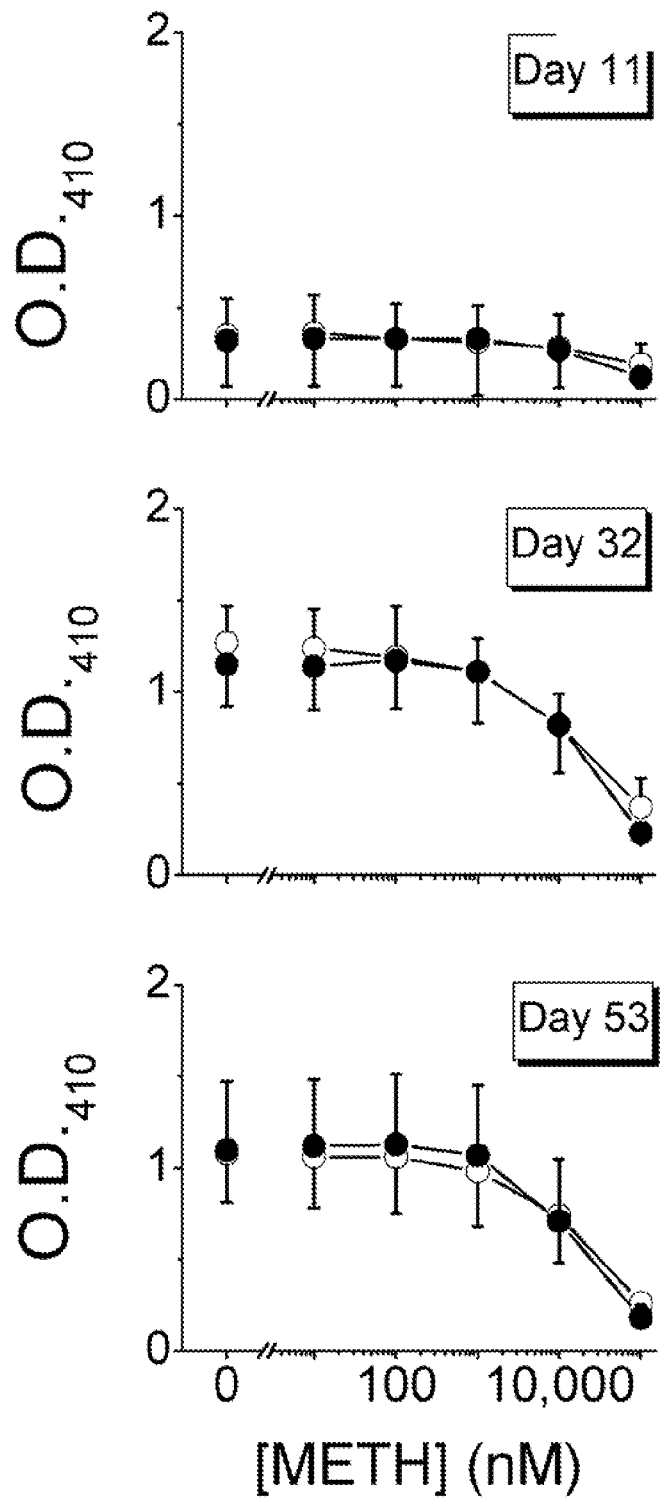
FIG. 6 presents rat serum antibody affinities for (+)METH as determined by ELISA. (+)METH P6-KLH immunized rats (●); (+)METH P6-KLH immunized rats with repeated (+)METH challenges (○).

By this measure, both groups of (+)METH P6-KLH immunized rats developed and maintained anti-(+)METH antibody titers throughout the 53-day immunization period (FIG. 5, open and closed circles) compared with control KLH-immunized rats, which had no response (squares). Repeated administration of (+)METH to immunized animals did not affect development or maintenance of anti-(+)METH titers (open circles), compared to immunized rats without a (+)METH challenge. In determining if there was a relative change in the serum antibody affinity for (+)METH in rats receiving repeated (+)METH administration, there was no difference in relative antibody affinity for (+)METH between non-challenged and (+)METH-challenged groups (FIG. 6).

Thus, challenging rats by repeated administration of (+)METH during the study did not affect antibody affinity constants for (+)METH or antibody serum titers. These studies demonstrate that chronic (+)METH use does not interfere with the quantity (titer) or quality (specificity, affinity) of the anti-(+)METH antibody response. These are important findings because many addicted patients will likely use (+)METH during their active immunization treatments.

Example 7

Anti-(+)METH mAb Alter (+)METH Pharmacokinetics in Rats

The ability of anti-(+)METH mAb6H4 (generated against (+)METH P6 hapten, see Table 1) to alter (+)METH brain concentrations was examined in two different models of (+)METH abuse (Byrnes-Blake et al., 2005, Eur J Pharmacol 521:86-94).

Figure 7:
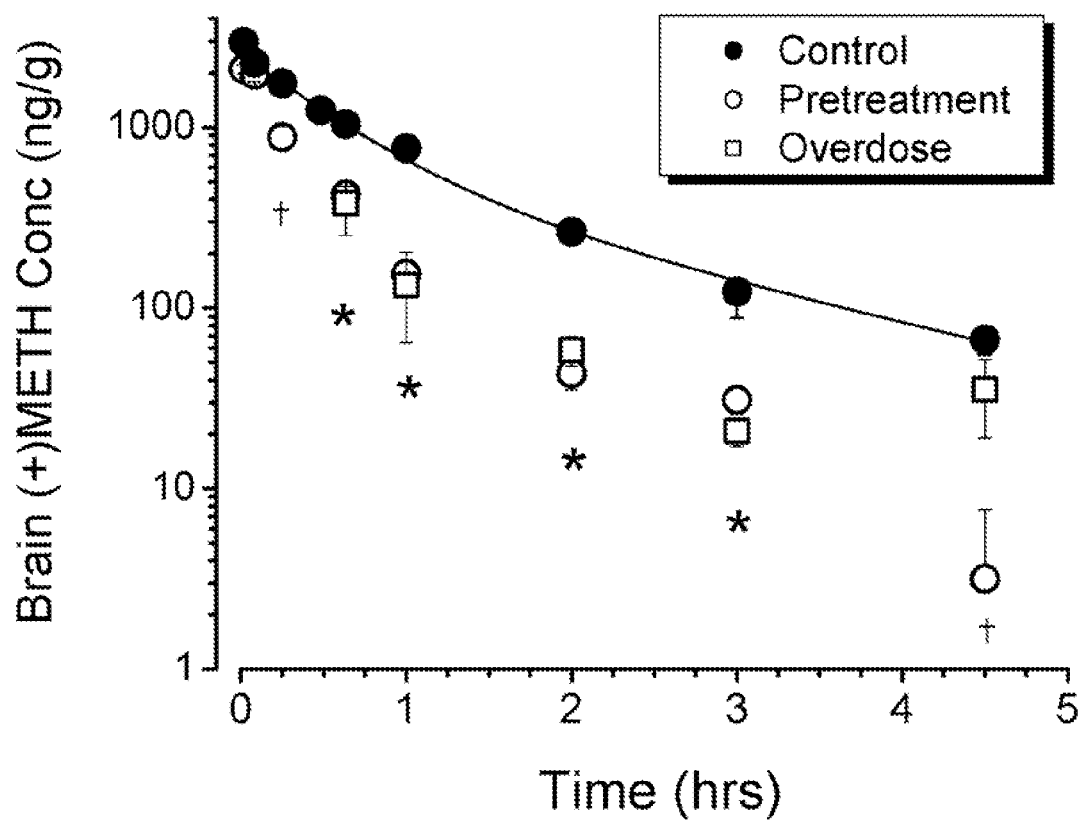
FIG. 7 illustrates clearance of brain (+)METH. Average concentration vs. time profiles for (+)METH in the brain without mAb6H4 (•), in an overdose (□), and in a pretreatment model (○). The * indicates that both the overdose and pretreatment points are statistically different from control ($P<0.05$). The † indicates that only the pretreatment time points are statistically different from the control ($P<0.05$).

The overdose model was designed to mimic a drug abuser taking a high iv (+)METH dose and treated with (+)METH mAb in the emergency room. In this model, rats received 1 mg/kg (+)METH (iv) followed 30 min later by an anti-(+) METH mAb dose. The mAb pretreatment model was designed to mimic an abuser in drug treatment administered an anti-(+)METH mAb medication at the start of behavioral modification therapy who relapses to (+)METH use. In this model, rats were pretreated with anti-(+)METH mAb6H4 and received a 1 mg/kg iv (+)METH dose the following day. This dose (without mAb) produced about 2.5 hrs of locomotor effects. Rats (3/time point) were sacrificed at varied times after (+)METH administration to determine (+)METH brain concentrations. As shown in FIG. 7, mAb6H4 decreased (+)METH brain concentrations in both models. Indeed, (+)METH brain concentrations in both models were virtually superimposable at comparable times after 30 min—the time of mAb administration in the overdose model. Both studies clearly show that antibodies against (+)METH can significantly reduce (+)METH brain concentrations over time.

Next, the "functional" half-life of each of the afore-mentioned anti-(+)METH mAbs (see Table 1) was determined. This "functional" assay compared (+)METH concentrations in the absence and presence of mAbs. By this measure, the best antibodies are those with the highest and longest increases in serum (+)METH and (+)AMP concentrations.

First, it was determined that the pharmacokinetic properties of the mAbs were not different. For instance, they all had a serum half-life of about 7-8 days, which ruled out the possibility that one or more of them were quickly cleared and thus inactivated through elimination. It also showed the potential to produce a long-acting anti-(+)METH therapy by passive or active immunization.

Figure 8:
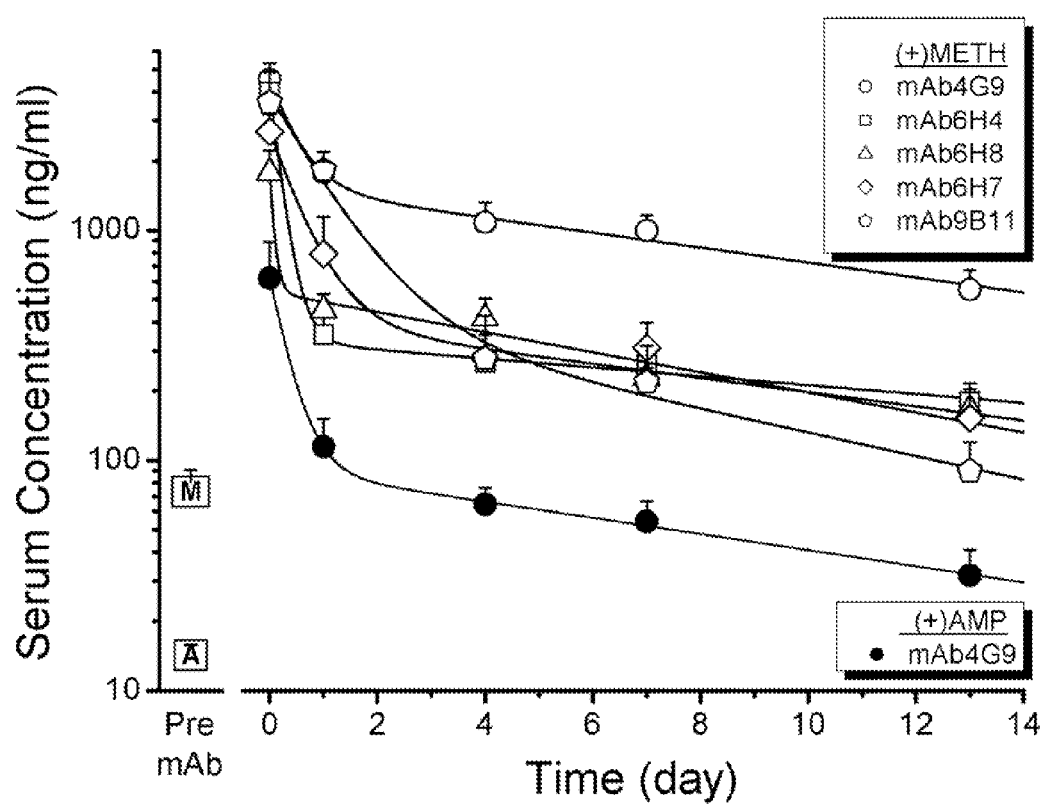
FIG. 8 presents serum concentration of (+)METH over time. (+)METH concentrations before (□ symbol with "M" inside) and after treatment (open symbols) with five different anti-(+)METH mAbs (n=3 rats/time point) and (+)AMP concentrations before (□ symbol with "A" inside) and after treatment (filled circles) with mAb4G9. (+)AMP concentrations (filled circles) are shown only for mAb4G9 because the other four mAbs did not produce long-term increases in (+)AMP concentrations. The best-fit line was determined using a weighted two-compartment pharmacokinetic model.

To conduct the "functional" studies, male rats (n=4/group) were given 14-day continuous (+)METH infusions at 5.6 mg/kg/day by sc osmotic minipumps. After achieving steady state (+)METH concentrations (at 24 hrs), each rat was treated with a dose of mAb that was equimolar in binding sites to the steady-state body burden of (+)METH. Only a single dose of mAb was administered at this time point, but (+)METH was continuously infused at a rate of 50% of the body burden per hour to maintain a (+)METH steady state. Serum samples were collected pre-mAb and at time points after mAb administration. All anti-(+)METH mAb caused significant acute increases in serum (+)METH concentrations compared with pre-mAb controls. However, there were substantial differences in serum (+)METH concentration vs. time curves for the five mAbs (FIG. 8, open symbols). Most anti-(+)METH mAbs appeared to be partially inactivated to differing degrees over time, as judged by their inability to maintain high concentrations of (+)METH in serum over time. This inactivation was particularly striking for the highest affinity mAb6H4 ($K_D$=11 nM). However, mAb4G9 ((+)METH and (+)AMP, $K_D$=34 and 51 nM, respectively) was still very effective after about 2 wks. It was also the only mAb that maintained significantly increased concentrations of (+)AMP (closed circles) and (+)METH (open circles) over time compared to pre-mAb concentrations (square symbols with "A" and "M" inside).

It was originally hypothesized that mAb affinity was the primary driving force for therapeutic efficacy. However, these studies revealed that the duration of action and function of the anti-(+)METH mAb in vivo was decreased based on predictions from known mAb pharmacokinetics, which was unanticipated. The first generation of haptens (e.g., (+)METH P6 and (+)METH P4) were purposely designed to produce mAbs specific for (+)METH, with virtually no cross reactivity with (+)AMP. When the second generation of haptens (e.g., (+)METH MO10) were produced with specificity for (+)METH and (+)AMP, it was discovered that the resulting mAb (mAb4G9) had the other advantages of increased duration of action and efficacy.

What is claimed is:

1. A compound comprising formula (IV):

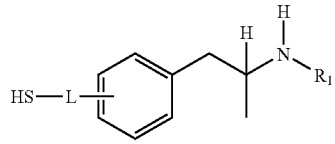

(IV)

wherein:
- $R_1$ is selected from the group consisting of hydrogen and methyl; and
- L comprises a linker of 7 to 10 contiguous atoms attached to the benzene ring at the meta position, the atoms being selected from the group consisting of a carbon atom of a hydrocarbyl group, a carbon atom of a substituted hydrocarbyl group, and a heteroatom.

2. A compound comprising formula (IX):

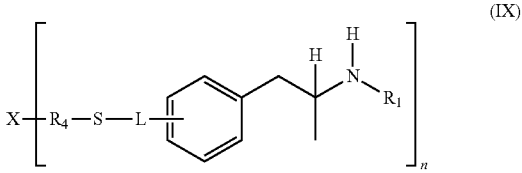

(IX)

wherein:
- $R_1$ is selected from the group consisting of hydrogen and methyl;
- n is an integer greater than or equal to 3;
- L comprises a linker of 7 to 10 contiguous atoms attached to the benzene ring at the meta position, the atoms being selected from the group consisting of a carbon atom of a hydrocarbyl group, a carbon atom of a substituted hydrocarbyl group, and a heteroatom;

X is a carrier molecule that elicits an immunogenic response; and $R_4$ is selected from the group consisting of a direct bond, hydrocarbyl, and substituted hydrocarbyl.

3. The compound of claim 2, wherein $R_4$ is [N-maleimidomethyl]cyclohexane-1-carboxylate.

4. A compound comprising formula (V):

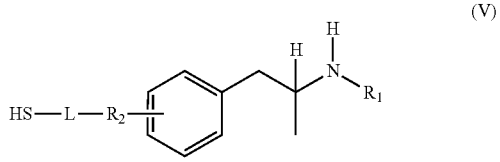

(V)

wherein:
$R_1$ is selected from the group consisting of hydrogen and methyl;
$R_2$ is a heteroatom; and
L comprises a linker of 6 to 9 contiguous atoms attached to the benzene ring at the meta position, the atoms being selected from the group consisting of a carbon atom of a hydrocarbyl group, a carbon atom of a substituted hydrocarbyl group, and a heteroatom.

5. The compound of claim 4, wherein $R_2$ is oxygen.

6. The compound of claim 5, wherein L is $^H(CH_2)_m$, wherein m is an integer between 6 and 9.

7. A compound comprising formula (X):

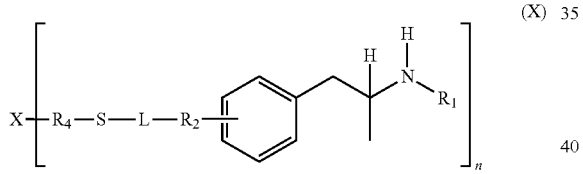

(X)

wherein:
$R_1$ is selected from the group consisting of hydrogen and methyl;

$R_2$ is a heteroatom;

L comprises a linker of 6 to 9 contiguous atoms attached to the benzene ring at the meta position, the atoms being selected from the group consisting of a carbon atom of a hydrocarbyl group, a carbon atom of a substituted hydrocarbyl group, and a heteroatom;

n is an integer greater than or equal to 3;

X is a carrier molecule that elicits an immunogenic response; and $R_4$ is selected from the group consisting of a direct bond, hydrocarbyl, and substituted hydrocarbyl.

8. The compound of claim 7, wherein $R_4$ is [N-maleimidomethyl]cyclohexane-1-carboxylate.

9. The compound of claim 1, wherein L is selected from the group consisting of $^H(CH_2)_m$, wherein m is an integer between 7 and 10, and $^H O(CH_2)_m$, wherein m is an integer between 6 and 9.

10. The compound of claim 1, wherein L is $^H O(CH_2)_5 CONH(CH_2)_2$.

11. The compound of claim 1, wherein L is $^H O(CH_2)_9$.

12. The compound of claim 2, wherein L is selected from the group consisting of $^H(CH_2)_m$, wherein m is an integer between 7 and 10, and $^H O(CH_2)_m$, wherein m is an integer between 6 and 9.

13. The compound of claim 2, wherein L is $^H O(CH_2)_5 CONH(CH_2)_2$.

14. The compound of claim 2, wherein L is $^H O(CH_2)_9$.

15. The compound of claim 5, wherein L is $^H(CH_2)_5 CONH(CH_2)_2$.

16. The compound of claim 5, wherein L is $^H(CH_2)_9$.

17. The compound of claim 7, wherein $R_2$ is oxygen.

18. The compound of claim 17, wherein L is $^H(CH_2)_m$, wherein m is an integer between 6 and 9.

19. The compound of claim 17, wherein L is $^H(CH_2)_5 CONH(CH_2)_2$.

20. The compound of claim 17, wherein L is $^H(CH_2)_9$.

* * * * *